US012558243B2

(12) United States Patent (10) Patent No.: US 12,558,243 B2
Haynes et al. (45) Date of Patent: Feb. 24, 2026

(54) SYSTEMS, DEVICES AND METHODS FOR DELIVERY SYSTEMS

(71) Applicant: Occam Labs LLC, Oakland, CA (US)

(72) Inventors: Evelyn N. Haynes, Los Gatos, CA (US); Peter W. Gregg, Santa Cruz, CA (US); Jeremy J. Boyette, Woodside, CA (US); Spencer C. Noe, San Miguel, CA (US); Daniel T. Wallace, Santa Cruz, CA (US)

(73) Assignee: Occam Labs LLC, Oakland, CA (US)

( * ) Notice: Subject to any disclaimer, the term of this patent is extended or adjusted under 35 U.S.C. 154(b) by 38 days.

(21) Appl. No.: 18/787,745

(22) Filed: Jul. 29, 2024

(65) Prior Publication Data

US 2024/0382329 A1 Nov. 21, 2024

Related U.S. Application Data

(63) Continuation of application No. 17/670,403, filed on Feb. 11, 2022, now Pat. No. 12,048,639, which is a
(Continued)

(51) Int. Cl.
*A61F 2/962* (2013.01)
*A61F 2/24* (2006.01)
(Continued)

(52) U.S. Cl.
CPC ............ *A61F 2/962* (2013.01); *A61F 2/2436* (2013.01); *A61M 25/0147* (2013.01);
(Continued)

(58) Field of Classification Search
CPC .................... A61F 2/962; A61F 2/2436; A61F 2230/0078; A61F 2230/008;
(Continued)

(56) References Cited

U.S. PATENT DOCUMENTS 4,477,930 A 10/1984 Totten et al.
5,476,510 A 12/1995 Eberhardt et al.
(Continued)

FOREIGN PATENT DOCUMENTS

EP 3383324 A4 7/2019
EP 2922592 B1 9/2022
(Continued)

OTHER PUBLICATIONS

Extended European Search Report issued in European Application No. 22753382.5, mailed on Dec. 6, 2024, 8 pages.
(Continued)

*Primary Examiner* — Andrew Restaino
(74) *Attorney, Agent, or Firm* — Dorsey & Whitney LLP

(57) ABSTRACT

Delivery systems for expandable and stented implants include adjustable tensioning members that control the expansion of the implant along the length of the implant. The tensioning members are wound onto one or more rotors located on the distal segment of the delivery system, which are rotated to unwind the tensioning members and incrementally expand the implant. Positioning mechanisms are also provided to adjust the position and orientation of the implant during delivery.

17 Claims, 41 Drawing Sheets

Related U.S. Application Data continuation of application No. 17/179,308, filed on Feb. 18, 2021, now Pat. No. 11,246,726.

(60) Provisional application No. 63/150,518, filed on Feb. 17, 2021, provisional application No. 63/148,124, filed on Feb. 10, 2021.

(51) Int. Cl.
*A61M 25/01* (2006.01)
*A61M 25/09* (2006.01)

(52) U.S. Cl.
CPC ..... *A61M 25/09* (2013.01); *A61F 2230/0078* (2013.01); *A61F 2230/008* (2013.01); *A61F 2250/0012* (2013.01); *A61M 2207/00* (2013.01)

(58) Field of Classification Search
CPC ............ A61F 2250/0012; A61F 2/9517; A61F 2/2439; A61M 25/0147; A61M 25/09; A61M 2207/00; A61M 25/0138
See application file for complete search history.

(56) References Cited

U.S. PATENT DOCUMENTS

| | | | |
|---|---|---|---|
| 5,904,667 A | 5/1999 | Falwell |
| 6,511,768 B1 | 1/2003 | Trapp et al. |
| 6,817,974 B2 | 11/2004 | Cooper et al. |
| 8,403,983 B2 | 3/2013 | Quadri et al. |
| 8,475,366 B2 | 7/2013 | Boulais et al. |
| 8,500,792 B2 | 8/2013 | Berra |
| 8,608,648 B2 | 12/2013 | Banik et al. |
| 8,622,894 B2 | 1/2014 | Banik et al. |
| 8,728,155 B2 | 5/2014 | Montorfano et al. |
| 8,870,948 B1 | 10/2014 | Erzberger et al. |
| 9,149,372 B2 | 10/2015 | Kasprzak et al. |
| 9,232,995 B2 | 1/2016 | Kovalsky et al. |
| 9,326,853 B2 | 5/2016 | Olson et al. |
| 9,339,379 B2 | 5/2016 | Quadri et al. |
| 9,421,071 B2 | 8/2016 | Smith et al. |
| 9,439,757 B2 | 9/2016 | Wallace et al. |
| 9,492,273 B2 | 11/2016 | Wallace et al. |
| 9,554,899 B2 | 1/2017 | Granada et al. |
| 9,561,103 B2 | 2/2017 | Granada et al. |
| 9,572,957 B2 | 2/2017 | Osypka et al. |
| 10,016,276 B2 | 7/2018 | Brunnett et al. |
| 10,028,826 B2 | 7/2018 | Yohanan et al. |
| 10,039,639 B2 | 8/2018 | Marchand et al. |
| 10,143,552 B2 | 12/2018 | Wallace et al. |
| 10,149,761 B2 | 12/2018 | Granada et al. |
| 10,154,906 B2 | 12/2018 | Granada et al. |
| 10,231,827 B2 | 3/2019 | Mulvihill |
| 10,368,990 B2 | 8/2019 | Noe et al. |
| 10,433,953 B2 | 10/2019 | Wallace et al. |
| 10,433,961 B2 | 10/2019 | Mclean |
| 10,456,255 B2 | 10/2019 | Montorfano et al. |
| 10,470,881 B2 | 11/2019 | Noe et al. |
| 10,485,660 B2 | 11/2019 | Quadri et al. |
| 10,500,047 B2 | 12/2019 | Olson et al. |
| 10,524,901 B2 | 1/2020 | Quadri et al. |
| 10,543,079 B2 | 1/2020 | Quill et al. |
| 10,548,721 B2 | 2/2020 | Wallace et al. |
| 10,555,808 B2 | 2/2020 | Wallace et al. |
| 10,555,825 B2 | 2/2020 | Gong et al. |
| 10,568,737 B2 | 2/2020 | Noe et al. |
| 10,583,000 B2 | 3/2020 | Ratz et al. |
| 10,583,007 B2 | 3/2020 | Chang et al. |
| 10,610,355 B2 | 4/2020 | Marchand et al. |
| 10,624,742 B2 | 4/2020 | Granada et al. |
| 10,631,981 B2 | 4/2020 | Von Oepen et al. |
| 10,639,146 B2 | 5/2020 | Quadri et al. |
| 10,639,151 B2 | 5/2020 | Von Oepen et al. |
| 10,646,689 B2 | 5/2020 | Von Oepen et al. |
| 10,661,052 B2 | 5/2020 | Mcniven et al. |
| 10,702,378 B2 | 7/2020 | Miyashiro |
| 10,743,992 B2 | 8/2020 | Krans et al. |
| 10,751,485 B2 | 8/2020 | Von Oepen et al. |
| 10,765,513 B2 | 9/2020 | Mendelson et al. |
| 10,772,727 B2 | 9/2020 | Vaughan |
| 10,772,749 B2 | 9/2020 | Gloss et al. |
| 10,792,151 B2 | 10/2020 | Mauch et al. |
| 10,828,153 B2 | 11/2020 | Noe et al. |
| 10,849,746 B2 | 12/2020 | Gregg et al. |
| 10,869,755 B2 | 12/2020 | Granada et al. |
| 10,869,757 B2 | 12/2020 | Kovalsky et al. |
| 10,874,512 B2 | 12/2020 | Von Oepen et al. |
| 10,925,728 B2 | 2/2021 | Anderson et al. |
| 10,933,216 B2 | 3/2021 | Von Oepen et al. |
| 10,945,835 B2 | 3/2021 | Morriss et al. |
| 10,974,027 B2 | 4/2021 | Mcniven et al. |
| 11,045,315 B2 | 6/2021 | Valencia et al. |
| 11,058,535 B2 | 7/2021 | Noe et al. |
| 11,083,577 B2 | 8/2021 | Zhang et al. |
| 11,083,583 B2 | 8/2021 | Kirk et al. |
| 11,090,158 B2 | 8/2021 | Noe et al. |
| 11,109,964 B2 | 9/2021 | Hacohen |
| 11,109,967 B2 | 9/2021 | Von Oepen et al. |
| 11,185,411 B2 | 11/2021 | Gregg et al. |
| 11,191,642 B2 | 12/2021 | Haynes et al. |
| 11,197,755 B1 | 12/2021 | Wallace et al. |
| 11,234,819 B2 | 2/2022 | Rabito et al. |
| 11,246,726 B1 | 2/2022 | Wallace et al. |
| 11,324,495 B2 | 5/2022 | Von Oepen et al. |
| 11,331,187 B2 | 5/2022 | Wallace et al. |
| 11,452,597 B2 | 9/2022 | Quadri et al. |
| 11,471,645 B2 | 10/2022 | Mcniven et al. |
| 11,484,408 B2 | 11/2022 | Von Oepen et al. |
| 11,491,309 B2 | 11/2022 | Caton et al. |
| 11,510,780 B2 | 11/2022 | Granada et al. |
| 11,617,646 B2 | 4/2023 | Wallace et al. |
| 11,633,278 B2 | 4/2023 | Noe et al. |
| 11,648,112 B2 | 5/2023 | Wallace et al. |
| 11,648,357 B2 | 5/2023 | Von Oepen et al. |
| 11,679,236 B2 | 6/2023 | Von Oepen et al. |
| 11,701,214 B2 | 7/2023 | Haynes et al. |
| 11,723,768 B2 | 8/2023 | Von Oepen et al. |
| 11,724,068 B2 | 8/2023 | Von Oepen et al. |
| 11,759,319 B2 | 9/2023 | Wallace et al. |
| 11,786,373 B2 | 10/2023 | Gregg et al. |
| 11,793,973 B2 | 10/2023 | Mcniven et al. |
| 11,826,251 B2 | 11/2023 | Gregg et al. |
| 12,029,646 B2 | 7/2024 | Hariton et al. |
| 12,048,639 B2 | 7/2024 | Wallace et al. |
| 12,064,345 B2 | 8/2024 | Marchand et al. |
| 2003/0236567 A1 | 12/2003 | Elliot |
| 2004/0034408 A1 | 2/2004 | Majercak et al. |
| 2005/0273151 A1 | 12/2005 | Fulkerson et al. |
| 2007/0142906 A1 | 6/2007 | Figulla et al. |
| 2009/0187240 A1 | 7/2009 | Clerc |
| 2010/0082094 A1 | 4/2010 | Quadri et al. |
| 2011/0022157 A1 | 1/2011 | Essinger et al. |
| 2011/0098802 A1 | 4/2011 | Braido et al. |
| 2011/0218619 A1 | 9/2011 | Benichou et al. |
| 2012/0078356 A1 | 3/2012 | Fish et al. |
| 2012/0191183 A1 | 7/2012 | Rzany et al. |
| 2013/0018458 A1 | 1/2013 | Yohanan et al. |
| 2013/0197629 A1 | 8/2013 | Gainor et al. |
| 2013/0204357 A1 | 8/2013 | Thill et al. |
| 2013/0204360 A1 | 8/2013 | Gainor |
| 2013/0274873 A1 | 10/2013 | Delaloye et al. |
| 2013/0304200 A1 | 11/2013 | Mclean et al. |
| 2013/0310928 A1 | 11/2013 | Morriss et al. |
| 2014/0005778 A1 | 1/2014 | Buchbinder et al. |
| 2014/0018915 A1 | 1/2014 | Biadillah et al. |
| 2014/0031924 A1 | 1/2014 | Bruchman et al. |
| 2014/0200649 A1 | 7/2014 | Essinger et al. |
| 2014/0243965 A1 | 8/2014 | Benson et al. |
| 2014/0277414 A1 | 9/2014 | Kheradvar |
| 2014/0303719 A1 | 10/2014 | Cox et al. |
| 2014/0330370 A1 | 11/2014 | Matheny et al. |
| 2014/0371844 A1 | 12/2014 | Dale et al. |
| 2015/0327996 A1 | 11/2015 | Fahim et al. |

(56)　　　　　References Cited

U.S. PATENT DOCUMENTS

| | | |
|---|---|---|
| 2015/0328002 A1 | 11/2015 | Mclean et al. |
| 2016/0030167 A1 | 2/2016 | Delaloye et al. |
| 2016/0030169 A1 | 2/2016 | Shahriari |
| 2016/0213826 A1 | 7/2016 | Tanner et al. |
| 2016/0235525 A1 | 8/2016 | Rothstein et al. |
| 2016/0331529 A1 | 11/2016 | Marchand et al. |
| 2017/0100236 A1 | 4/2017 | Robertson et al. |
| 2017/0128203 A1 | 5/2017 | Zhang et al. |
| 2017/0216027 A1 | 8/2017 | Marchand et al. |
| 2017/0231761 A1 | 8/2017 | Cohen-Tzemach et al. |
| 2017/0325945 A1 | 11/2017 | Dale et al. |
| 2017/0325948 A1 | 11/2017 | Wallace et al. |
| 2018/0021129 A1 | 1/2018 | Peterson et al. |
| 2018/0055629 A1 | 3/2018 | Oba et al. |
| 2018/0110622 A1 | 4/2018 | Gregg et al. |
| 2018/0116689 A1* | 5/2018 | Nakano ................... A61F 2/013 |
| 2018/0125642 A1 | 5/2018 | White et al. |
| 2018/0206983 A1 | 7/2018 | Noe et al. |
| 2018/0256241 A1 | 9/2018 | Cohen et al. |
| 2018/0256331 A1* | 9/2018 | Vaughan .............. A61F 2/2466 |
| 2018/0296335 A1 | 10/2018 | Miyashiro |
| 2018/0296341 A1 | 10/2018 | Noe et al. |
| 2018/0333259 A1 | 11/2018 | Dibie |
| 2019/0008636 A1 | 1/2019 | Francis et al. |
| 2019/0099267 A1 | 4/2019 | Tubishevitz et al. |
| 2019/0183629 A1 | 6/2019 | Karavany et al. |
| 2019/0183642 A1 | 6/2019 | Tegels et al. |
| 2019/0192289 A1 | 6/2019 | Levi et al. |
| 2019/0240013 A1 | 8/2019 | Kovalsky et al. |
| 2019/0247188 A1 | 8/2019 | Wallace et al. |
| 2019/0262129 A1 | 8/2019 | Cooper et al. |
| 2019/0321171 A1 | 10/2019 | Morriss et al. |
| 2019/0343625 A1 | 11/2019 | Gharib et al. |
| 2019/0365538 A1 | 12/2019 | Chambers et al. |
| 2019/0374342 A1 | 12/2019 | Gregg et al. |
| 2019/0380833 A1 | 12/2019 | Yohanan et al. |
| 2020/0054447 A1 | 2/2020 | Wallace et al. |
| 2020/0078167 A1 | 3/2020 | Quijano et al. |
| 2020/0113683 A1 | 4/2020 | Dale et al. |
| 2020/0113686 A1 | 4/2020 | Olson et al. |
| 2020/0129292 A1 | 4/2020 | Haynes et al. |
| 2020/0197175 A1 | 6/2020 | Chang et al. |
| 2020/0229920 A1 | 7/2020 | Wallace et al. |
| 2020/0229922 A1 | 7/2020 | Granada et al. |
| 2020/0237507 A1 | 7/2020 | Noe et al. |
| 2020/0246527 A1 | 8/2020 | Hildebrand et al. |
| 2020/0276014 A1 | 9/2020 | Burkart et al. |
| 2020/0323634 A1 | 10/2020 | Von Oepen et al. |
| 2020/0345493 A1 | 11/2020 | Gregg et al. |
| 2020/0352717 A1 | 11/2020 | Kheradvar et al. |
| 2020/0405926 A1 | 12/2020 | Alexander et al. |
| 2021/0000593 A1 | 1/2021 | Rahmig et al. |
| 2021/0038386 A1 | 2/2021 | Gregg et al. |
| 2021/0068950 A1 | 3/2021 | Quill et al. |
| 2021/0186693 A1 | 6/2021 | Vidlund et al. |
| 2021/0196459 A1 | 7/2021 | Marchand et al. |
| 2021/0205073 A1 | 7/2021 | Haynes |
| 2021/0220137 A1 | 7/2021 | Noe et al. |
| 2021/0267755 A1 | 9/2021 | Wallace |
| 2021/0275297 A1 | 9/2021 | Berndt et al. |
| 2021/0307943 A1 | 10/2021 | Gupta et al. |
| 2021/0315691 A1 | 10/2021 | Rahmig et al. |
| 2021/0338425 A1 | 11/2021 | Hyde |
| 2021/0346153 A1 | 11/2021 | Metmeier et al. |
| 2021/0361404 A1 | 11/2021 | Haynes et al. |
| 2021/0369257 A1 | 12/2021 | Huddleston |
| 2021/0386542 A1 | 12/2021 | Schankereli et al. |
| 2022/0015895 A1 | 1/2022 | Wallace et al. |
| 2022/0039949 A1 | 2/2022 | Haynes et al. |
| 2022/0071765 A1 | 3/2022 | Gregg et al. |
| 2022/0071766 A1 | 3/2022 | Olson et al. |
| 2022/0087814 A1 | 3/2022 | Vidlund |
| 2022/0175523 A1 | 6/2022 | Dibie et al. |
| 2022/0192824 A1 | 6/2022 | Vidlund et al. |
| 2022/0249265 A1 | 8/2022 | Wallace et al. |
| 2022/0313428 A1 | 10/2022 | Bergin |
| 2022/0323213 A1 | 10/2022 | Wallace et al. |
| 2022/0331103 A1 | 10/2022 | Von Oepen et al. |
| 2022/0354678 A1 | 11/2022 | Shelton et al. |
| 2023/0030110 A1 | 2/2023 | Hake et al. |
| 2023/0034126 A1 | 2/2023 | Granada et al. |
| 2023/0125281 A1 | 4/2023 | Alleleyn |
| 2023/0233320 A1 | 7/2023 | Uihlein |
| 2023/0240842 A1 | 8/2023 | Licht et al. |
| 2023/0277307 A1 | 9/2023 | Noe et al. |
| 2023/0364387 A1 | 11/2023 | Monteon et al. |
| 2023/0380967 A1 | 11/2023 | Shelton et al. |
| 2024/0358500 A1 | 10/2024 | Zhang et al. |
| 2025/0248807 A1 | 8/2025 | Noe et al. |

FOREIGN PATENT DOCUMENTS

| | | |
|---|---|---|
| KR | 20110038617 A | 4/2011 |
| KR | 20180023943 A | 3/2018 |
| WO | 2014081796 A1 | 5/2014 |
| WO | 2022094001 | 5/2022 |
| WO | 2022173997 A1 | 8/2022 |
| WO | WO2022/173997 | 8/2022 |

OTHER PUBLICATIONS

Extended European Search Report issued in European Patent Application No. 21887473.3, mailed on Sep. 10, 2024, 7 pages.
First Examination Report issued in Australian Patent Application No. 2021371160, mailed on Jan. 3, 2025, 3 pages.
Office Action issued in Korean Patent Application No. 10-2023-7017609, issued on Feb. 10, 2025, 6 pages including 3 pages of English translation.
International Preliminary Report on Patentability issued in International Application No. PCT/US2022/016042, mailed on Aug. 24, 2023, 13 pages.
International Preliminary Report on Patentability issued in International Application No. PCT/US2022/056915, mailed on May 11, 2023, 7 pages.
International Search Report and Written Opinion Issued in International Application No. PCT/US2022/016042 mailed on May 3, 2022, 17 pages.
International Search Report and Written Opinion received in PCT App. No. PCT/US2021/056915 dated Dec. 1, 2021.
First Examination Report issued in Canadian Application No. 3,199,747, mailed on May 7, 2025, 4 pages.
Notice of Allowance issued in Korean Patent Application No. 10-2023-7017609, mailed on Jun. 19, 2025, 10 pages including 5 pages of machine English translation.
Second Examination Report issued in Australian patent application No. 2021371160, mailed on Feb. 27, 2025, 2 pages.
First Examination Report issued in Australian Application No. 2025217374, mailed on Oct. 1, 2025, 3 pages.

* cited by examiner

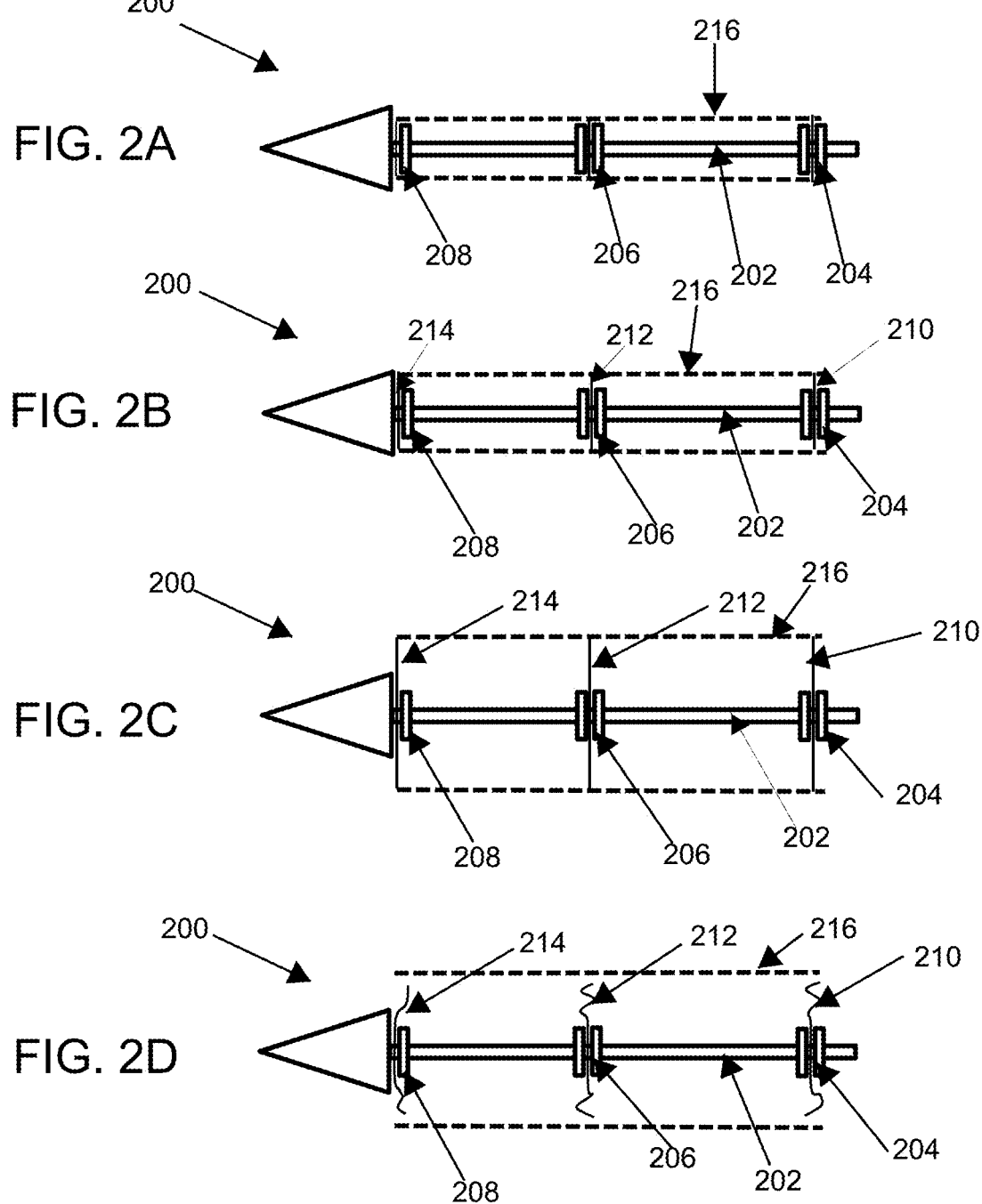

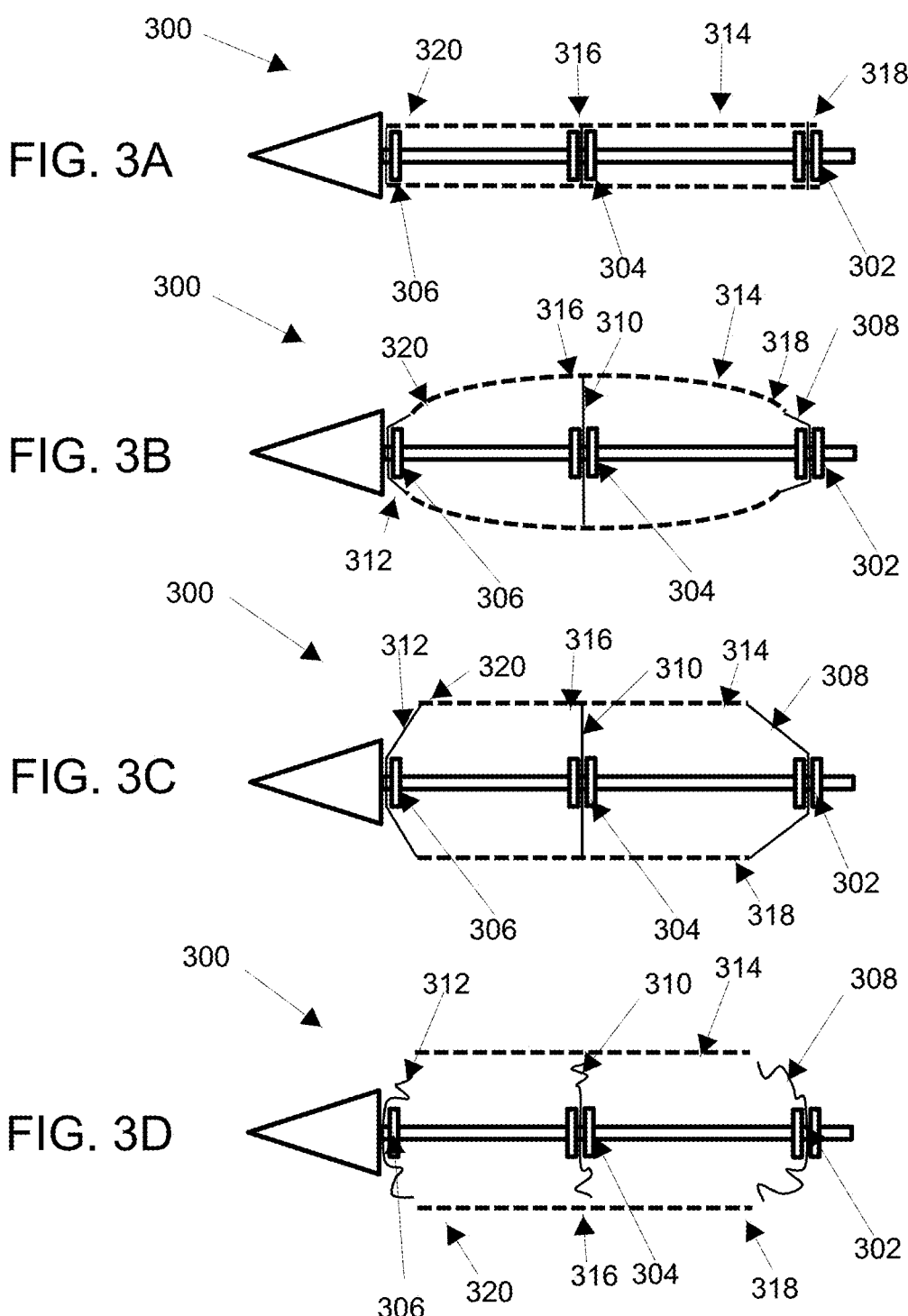

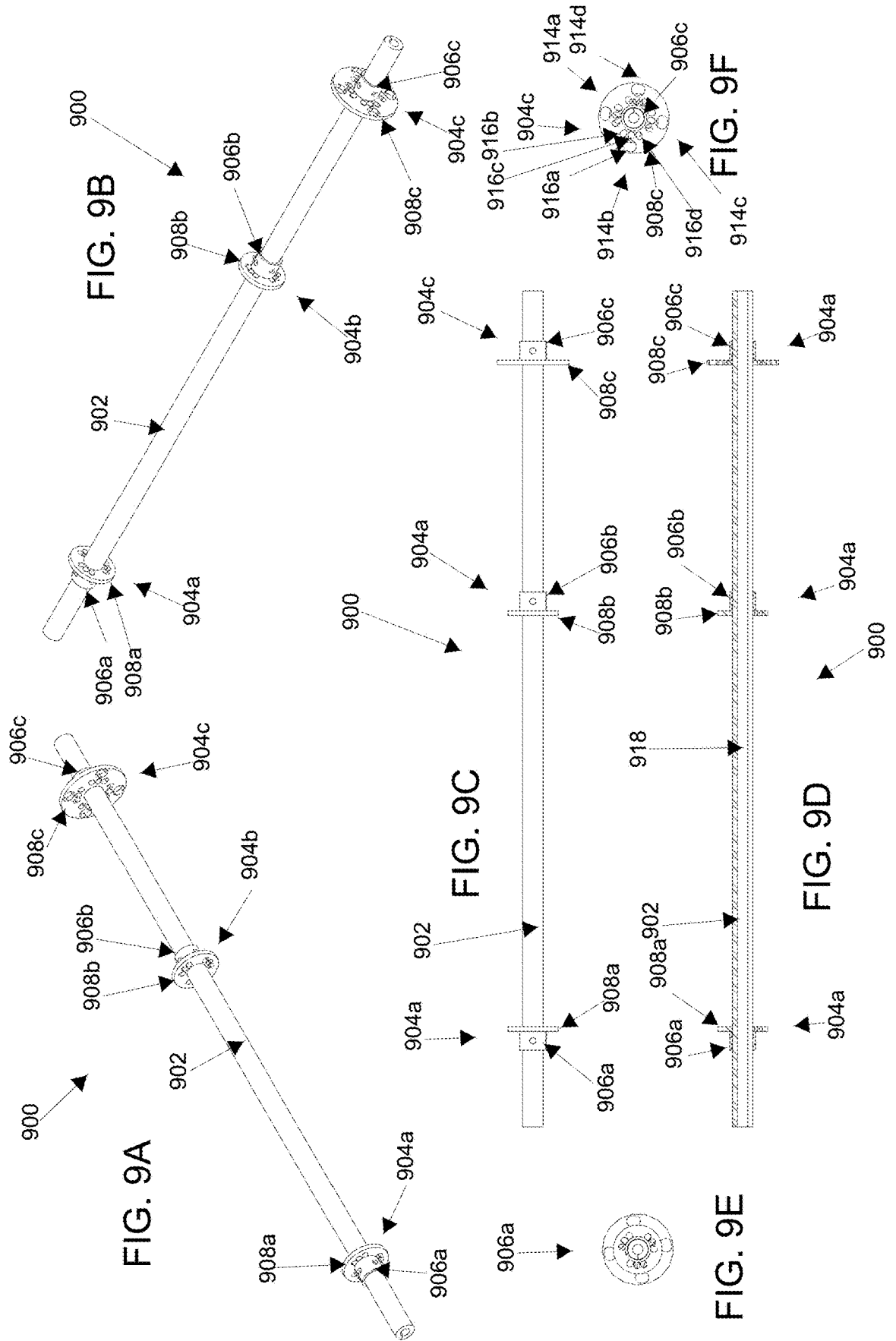

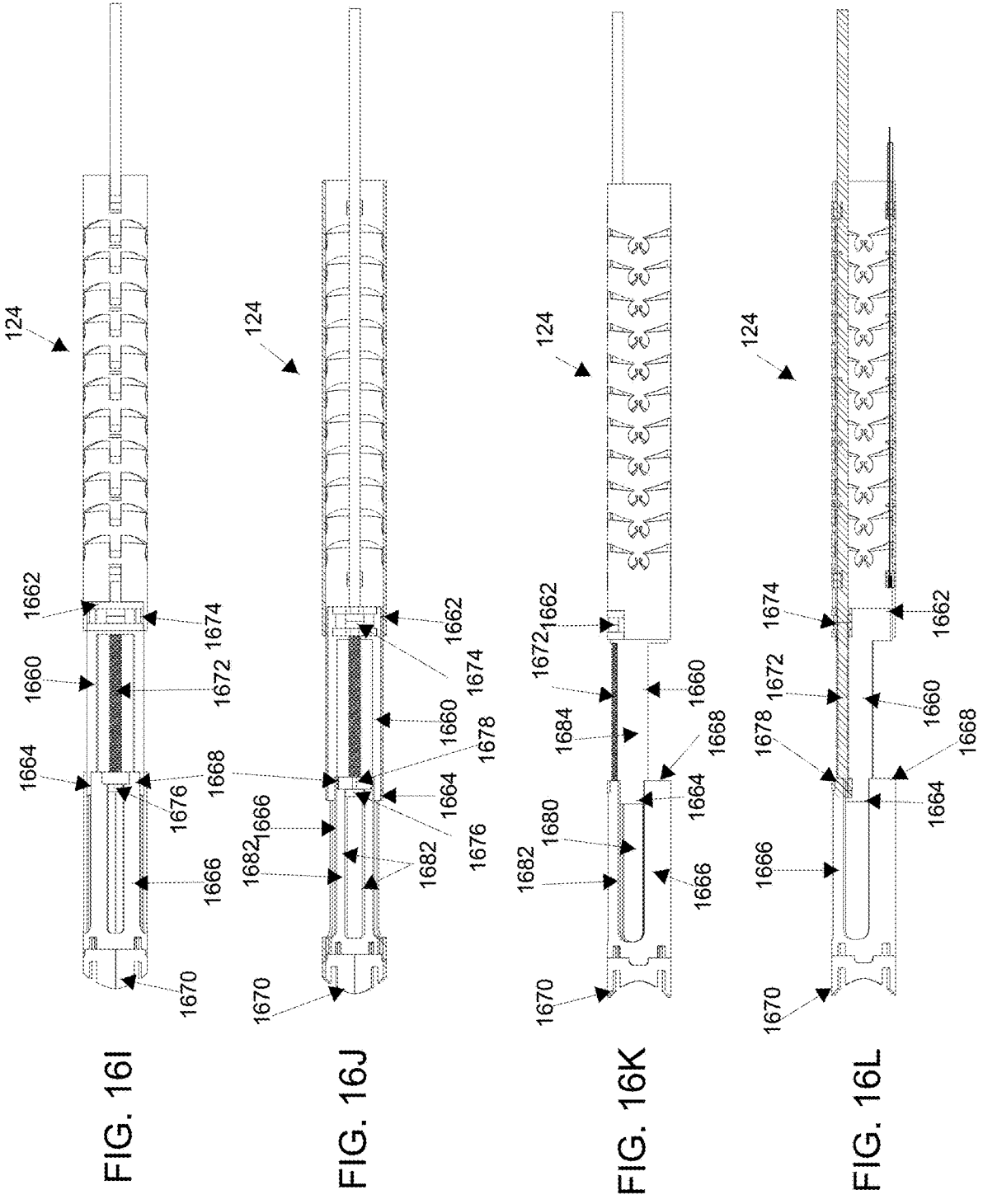

SYSTEMS, DEVICES AND METHODS FOR DELIVERY SYSTEMS

CROSS-REFERENCE TO RELATED APPLICATION(S)

This application is a continuation of U.S. application Ser. No. 17/670,403 filed Feb. 11, 2022, issued as U.S. Pat. No. 12,048,639 on Jul. 30, 2024, which is a continuation of U.S. application Ser. No. 17/179,308 filed Feb. 18, 2021, issued as U.S. Pat. No. 11,246,726 on Feb. 15, 2022, which claims priority to U.S. Provisional Application No. 63/150,518 filed Feb. 17, 2021 and U.S. Provisional Application No. 63/148,124 filed Feb. 10, 2021, which are incorporated herein by reference, in their entirety, for any purpose.

BACKGROUND

This patent application relates generally to the delivery of expandable and stented devices diseases, and more specifically to methods and apparatus for minimally invasive delivery of expandable or stented implants, such as into the cardiovascular system, such as heart valve replacement.

Valvular heart disease is a significant burden to patients and healthcare systems, with a prevalence of 2-3% worldwide, and with an increasing prevalence in aging populations. Valvular disease may result from a variety of etiologies, including autoimmune, infective and degenerative causes. The epidemiology of valvular disease also varies with the affected valve, with rheumatic heart disease being the cause worldwide of primary mitral regurgitation and mitral stenosis, but with secondary mitral disease from left ventricular dysfunction being more common in developed countries.

While surgical repair and valve replacement remains a mainstay of many mitral valve therapies in the current clinical guidelines by the American Heart Association and American College of Cardiology, transcatheter mitral repair is recommended for certain patient populations. In the 2017 Focused Update and the 2014 Guidelines for Management of Patients with Valvular Disease, the AHA/ACC recommended percutaneous mitral valve balloon commissurotomy for severe mitral valve stenosis, and transcatheter mitral valve repair in certain severely symptomatic patients with severe primary mitral regurgitation with a reasonable life expectancy who are non-surgical candidates due to comorbidities.

BRIEF SUMMARY

Further growth of transcatheter mitral valve therapies is challenged by the difficulty by mitral valve anatomy and physiology, compared to more established transcatheter aortic valve therapies. The tortuous anatomical pathways between the remote anatomical location and the target anatomical location often exerts stresses and strains on the delivery system that can affect the concordance between the controls on the proximal end of the delivery system and the effectors on the distal end of the device.

To facilitate the expansion and release at the target location, the delivery system may include an adjustable radial tensioning system that provides control of implant expansion via extension of the tensioning members. The tensioning members are contained within the distal region of the delivery system and therefore are not subject to stretching or slippage over the distances between the proximal control and distal region of the delivery system, or from spring-out effects of expandable heart valves maintained in a collapsed configuration solely by a retention sheath.

In some further embodiments, the delivery system may also comprise one or more steering or positioning mechanisms to facilitate final positioning and orientation of the implant at the target location, before and/or during expansion and release of the implant. The positioning mechanisms may include extension mechanisms which are configured to adjust the longitudinal position of a distal segment of the delivery system, without repositioning the entire delivery system relative to the patient's anatomy. Single axis and multi-axis steering mechanisms may also be included to facilitate the insertion and navigation of the delivery system through the anatomy, and to adjust the pose of distal segment of the delivery system and the implant during the delivery procedure.

In one embodiment, a delivery system is provided, comprising a proximal handle comprising a handle housing and a first actuator, a catheter body coupled to the handle, the catheter body comprising a distal section, a proximal section and a middle section therebetween, a rotatable drive shaft coupled to the first actuator and located in the catheter body, a first stator housing attached to the catheter body, the first stator housing comprising an internal opening and an external opening, a first rotor attached to the rotatable drive shaft and located in the first stator housing, the first rotor comprising at least one tension line attachment site, and a movable sheath located over the catheter body. The delivery system may further comprise a self-expanding implant, the implant comprising a contracted configuration and an expanded configuration, and a first tensioning member releasably coupled to the self-expanding implant and fixedly coupled to the attachment site of the first rotor. The first tensioning member may be further wound around the first rotor, and may be wound around the first rotor at least three times. The delivery system may also further comprise a second stator housing attached to the catheter body and spaced apart from the first stator housing, the second stator housing comprising an internal opening and an external opening, a second rotor attached to the rotatable drive shaft and located in the second stator housing, the second rotor comprising at least one tension line attachment site. The delivery system may also further comprise a third stator housing attached to the catheter body and spaced apart from the first and second stator housings, the third stator housing comprising an internal opening and an external opening, a third rotor attached to the rotatable drive shaft and located in the third stator housing, the third rotor comprising at least one tension line attachment site. The first stator housing may be larger than the second stator housing and the first rotor is larger than the second rotor. The first stator housing may be larger than both the second and third stator housings and the first rotor is larger than the second and third rotors. The proximal handle may further comprise a first actuator lock, wherein the first actuator lock comprises locked and unlocked configurations and is biased to the lock configuration. The delivery system may further comprise a catheter extension assembly configured to reversibly adjust a longitudinal spacing between the distal section and the middle section of the catheter body. The catheter extension assembly may comprise a proximal housing with a proximal threaded lumen, a distal housing and a threaded extension shaft located in the proximal threaded lumen and coupled to the distal housing. The proximal housing and distal housing may comprise a slotted interface therebetween to resist rotational displacement therebetween. The proximal handle may further comprises a second actuator coupled to the threaded extension shaft. The delivery system may further comprise a first steering assembly comprising a first segmented tubular body and a first plurality of elongate steering wires. The first steering assembly may be located proximal to the catheter extension assembly. The first segmented tubular body may comprise a laser-cut tubular body. The delivery system may further comprise a second steering assembly comprising a second segmented tubular body and a second plurality of steering wires. The second steering assembly may be located distal to the catheter extension assembly. The first steering assembly and second steering assembly may comprise different bending configurations. For example, the first steering assembly may comprise a two-way steering assembly and the second steering assembly may comprise a four-way steering assembly. The first segmented tubular body may comprise segments attached by living hinges. The second segmented tubular body may comprise a plurality of discrete segments. Each of the plurality of discrete segments may comprise one or two non-planar end openings. The non-planar end openings comprise a hyperbolic paraboloid shape. Each of the plurality of discrete segments may comprises a perimeter bumper configured to slidably within a lumen of the distal section of the catheter body.

In another embodiment, a minimally invasive implant delivery system is provided, comprising a handle comprising first, second, third and fourth controls, a tubular catheter body attached to the handle, the catheter body comprising a distal section, a middle section and proximal section, a catheter extension assembly configured adjustably extend the distal section of the catheter body relative to the middle section, a first steering assembly located proximal to the catheter extension assembly, and a second steering assembly located distal to the catheter extension assembly. The implant delivery system may further comprise a main drive shaft coupled to the first control and extending through the first steering assembly, catheter extension assembly and second steering assembly, and an extension drive shaft extending through first steering assembly and terminating at the catheter extension assembly, the extension drive shaft coupled to the second control. The first and second controls may comprise rotary dials. The first steering assembly may be coupled to the third control and the second steering assembly is coupled to the fourth control. The third control comprise a pivot handle. The fourth control may comprise a joystick. The first steering assembly may be attached to a proximal end of the catheter extension assembly and the second steering assembly is attached to a distal end of the catheter extension assembly. The first steering assembly may be located within the middle section of the catheter body and wherein the second steering assembly may be located within the distal section of the catheter body.

In still another embodiment, a method of delivering an expandable implant is provided, comprising navigating an expandable implant to a target location using a delivery catheter, using at least one of a steering assembly and a catheter extension assembly of the delivery catheter to set the expandable implant in a target pose, withdrawing a catheter sheath to expose the expandable implant, and actuating at least one rotor of the delivery catheter to unwind and extend at least one tensioning member from the delivery catheter to permit expansion of the expandable implant, the at least one tensioning member attached to the expandable implant. The method may further comprise further actuating the at least one rotor of the delivery catheter after expansion of the expandable implant to permit separation of the at least one tensioning member from the deliver catheter. The method may further comprise unlocking a rotor lock before or during the actuation of the at least one rotor. Unlocking a rotor lock may comprise squeezing a rotor lock release of a delivery catheter handle and wherein actuating the at least one rotor comprises rotating a rotor dial of the delivery catheter handle. The squeezing of the rotor lock release and rotating the rotor dial may be performed with a single hand.

In another embodiment, a method of loading an expandable stent structure onto a delivery catheter is provided, comprising providing an expanded stent structure attached to a plurality of tensioning members at different locations of the expanded stent structure, inserting a delivery catheter through the expanded stent structure, attaching the plurality of tensioning members to a plurality of rotors located at a distal section of a delivery catheter, collapsing the stent structure onto the delivery catheter, rotating the plurality of rotors to wind the plurality of tensioning members onto the plurality of rotors, and extending a catheter sheath over the collapsed stent structure. Collapsing the stent structure may be performed by tensioning the tensioning members by rotating of the plurality of rotors, or by collapsing the stent structure by pushing or pulling the expanded stent structure through a tapered structure, for example.

In still another variation, a method for performing mitral valve replacement is provided, comprising positioning a delivery device containing a collapsed heart valve assembly in an orthogonal, centered pose across the native mitral valve, wherein the heart valve assembly comprises a self-expandable stent and attached valve leaflets, retracting a sheath of the delivery device to expose the collapsed heart valve, rotating a first rotor to unwind and extend a first tensioning member to permit expansion of a first end of the stent located in a left atrium, and rotating a second rotor to unwind extend a second tensioning member to permit expansion of a second end of the stent located in a left ventricle. Rotating the first and second rotors are attached to a common drive shaft but unwind the first and second tensioning members at different lengths per rotation. The method may further comprise accessing a femoral vein, inserting a transseptal puncture device through the femoral vein and to the right atrium, puncturing the intraatrial septum, and inserting the delivery device with a collapsed heart valve assembly through the femoral vein and into the left atrium. Expanding the first end of the stent and expanding the second end of the stent may occur simultaneously but wherein the diameters of the first and second rotors are different. The method may further comprise dilating the intraatrial septum. The method may also further comprise accessing the left thoracic cavity through the chest wall, puncturing the cardiac tissue at an apex of the left ventricle, and inserting the delivery device with a collapsed heart valve assembly though the chest wall and transapically into the left ventricle, or may further comprise accessing a femoral artery, and inserting the delivery device with a collapsed heart valve assembly through the femoral artery and aortic arch and into the left ventricle.

BRIEF DESCRIPTION OF THE DRAWINGS

FIGS. 2A to 2D schematically depict one configuration of a delivery system which simultaneously extends tensioning members at three rotors of the delivery system.

FIGS. 3A to 3D schematically depict another configuration of an exemplary delivery system where a middle rotor is actuated first or to a greater degree than a proximal and distal rotor.

FIGS. 9A and 9B are front and rear perspective views of the rotor shaft. FIGS. 9C and 9D are side elevational and side cross-sectional views of the rotor shaft in FIGS. 9A and 9B. FIGS. 9E and 9F are front and rear elevational views of the rotor shaft in FIGS. 9A and 9B.

FIGS. 16I to 16L are top plan, top cross-sectional, side elevational and side cross-sectional views, respectively, of the combined proximal steering and extension assembly of FIG. 16B in an extended configuration.

DETAILED DESCRIPTION

Figure 1A:
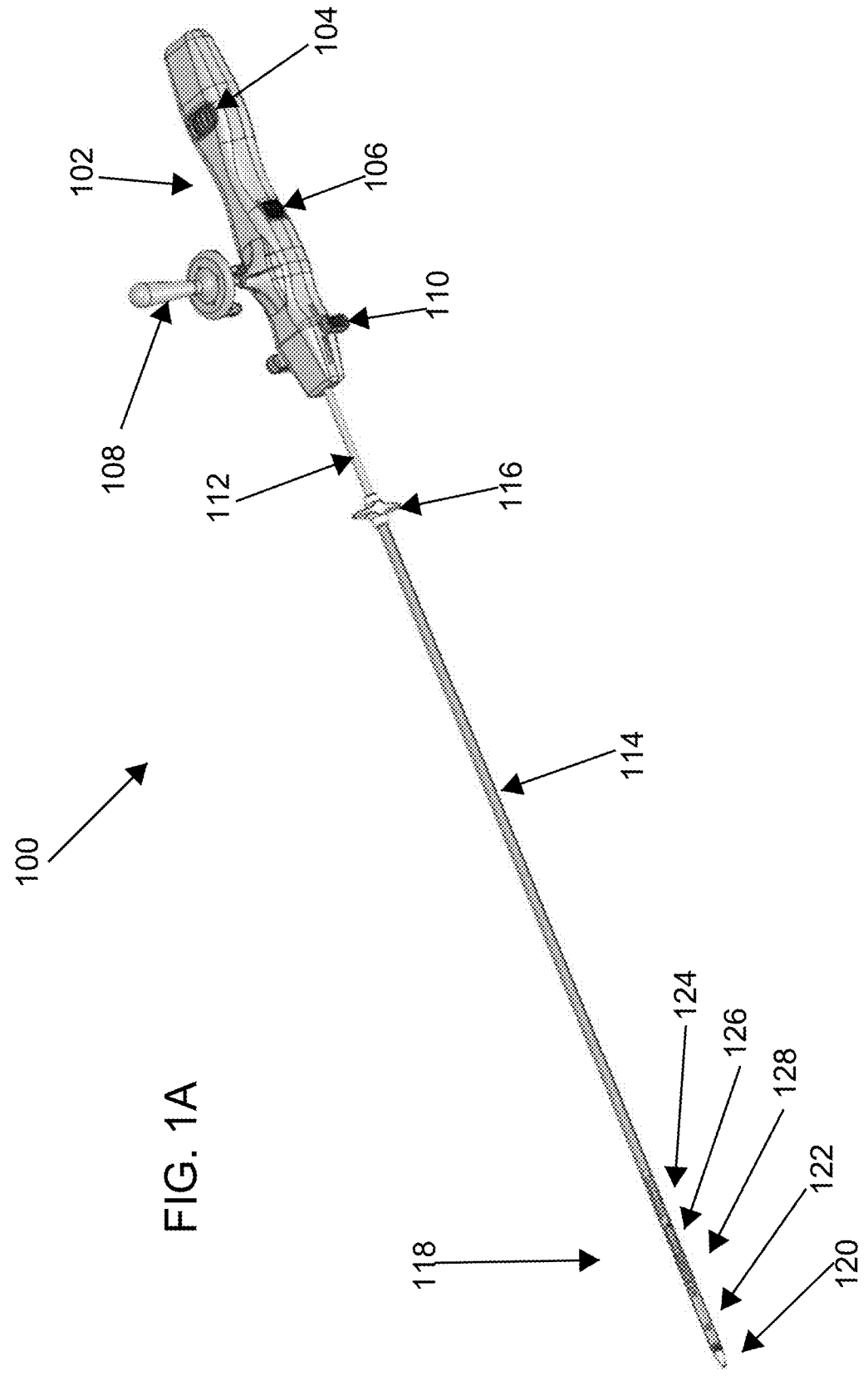
FIGS. 1A, 1B and 1C are top perspective, top plan and side elevational views, respectively of one exemplary embodiment of delivery system for an expandable implant.

FIG. 1 depicts one exemplary embodiment of a delivery system for a transcatheter heart valve replacement or other self-expanding stent structure. The delivery system 100 comprises a handle 102 with one or more actuators or user controls 104, 106, 108, 110, 130 and a catheter body 112 extending distally. The catheter body 112 is located inside an outer sheath 114 which can be moved by the user via a sheath handle 116 to sheath or expose a distal catheter section 118 with an atraumatic tip or nosecone 120 located at the distal end of the distal catheter section 118.

The distal catheter section 118 comprises an implant deployment section 122 that is configured to releasably retain a self-expanding implant (not shown) for delivery. The implant deployment section 122 includes a rotor/stator assembly, described in greater detail below, that is used to maintain the implant in a contracted or compressed configuration, and that can be adjusted to incrementally permit implant expansion toward its expanded configuration. The length of the catheter body 112 exposed between the sheath handle 116 and the main handle 102 will correspond generally to the length of the implant deployment section 122. In some further variations, depending on the physical characteristics of the implant and/or the delivery system, the rotor/stator assembly may also be used to contract or compress the implant back toward to the contracted or compressed configuration. One or more tensioning members that are attached to the implant and wound around the rotors are used to control the expansion and/or contraction of the implant. To facilitate the positioning and/or orientation of the implant deployment section 122 during the procedure, one or more steering or positioning mechanisms 124, 126, 128 may be provided along the catheter body 112, and are described in greater detail below.

Once the implant is expanded to the desired size and location, the delivery system may be separated from the implant in any of a variety of ways. For example, the one end or a middle portion of a tensioning member may be adhered, knotted or coupled by a friction fit to a rotor, while the other end or both ends of the tensioning member may be releasably attached to a clamp or other retention member located in the distal catheter section or in the handle of the delivery system. In other examples, the end(s) of the tensioning member may be severed by a cutting mechanism to separate the tension line from the implant or from the delivery system, e.g. where the tension line is retained on the implant after separation. In still other examples, the tensioning member may be transiently coupled to the rotor via one or more windings of the tensioning member that hold the tensioning member against the rotor. Upon further unwinding of the tensioning member, the end(s) of the tensioning member may be released, to allow the tensioning member to be pulled out of the implant for removal along with the delivery system.

Figures 1B, 1C:
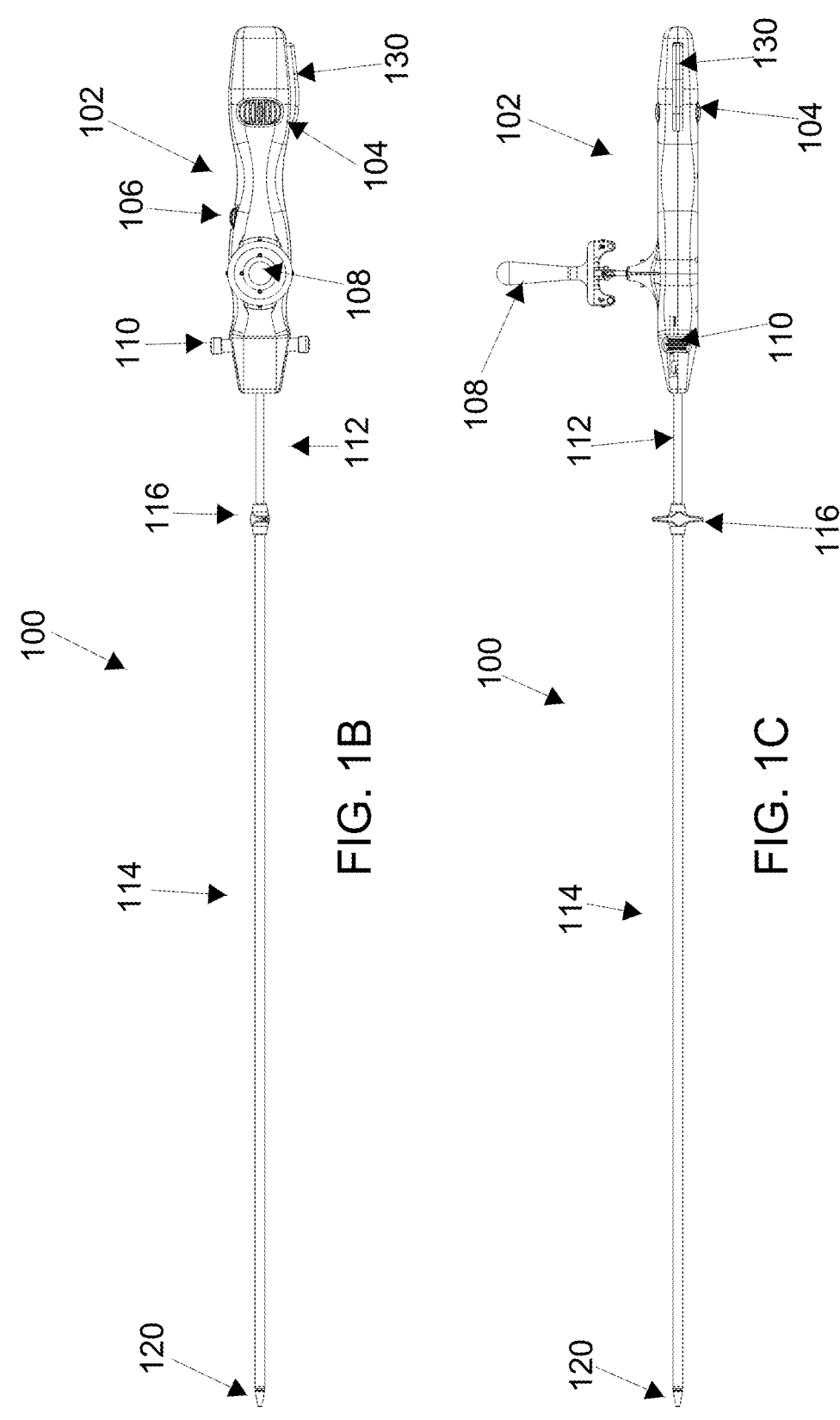

The rotor/stator assembly may comprise any of a variety of configurations. In one embodiment, depicted in FIGS. 2A to 2D, the implant deployment section 200 of the delivery system includes distal elongate body 202 from which the implant or stent 216 is released. The distal elongate body 202 includes multiple rotors/stators 204, 206, 208 spaced along the longitudinal length of the implant deployment region 202. As a drive shaft inside distal elongate body 202 is rotated, the tension lines 210, 212, 214 are unwound from the rotors/stators 204, 206, 208 in generally equal tension line lengths/rotation. The rotation of the drive shaft may be manipulated by the user at a control or knob 104 located in handle 102, as depicted in FIGS. 1A to 1C. The handle may also include a user releasable lock 130 that is holds the control of knob 104 in place, to avoid inadvertent release or expansion of the implant. In other examples, the knob 104 may comprise an auto-locking mechanism, e.g. a knob that is biased to the lock position by a spring that and must be pushed longitudinally to disengage and rotate the knob. Description of the exemplary knob 104 and the lock 130 are provided in greater detail below. This results in the stent implant 216 expansion in FIGS. 2B and 2C occurring equally along the length of the implant 216. Once expanded against the surrounding anatomical structure, the tension lines 210, 212, 214 may be separated from the implant 216 by further unwinding of the tension lines 210, 212, 214 until the tensioning members 210, 212, 214 are freed from self-binding to the rotors/stators 204, 206, 208, as schematically depicted in FIG. 2D. Although the depicted embodiment in FIGS. 2A to 2D includes three equally spaced apart rotors/stator 204, 206, 208, in other variations, a different number of rotors/stators may be provided and the spacing may be different between them, depending the implant configuration and the target location. In other variations, number of rotors/stators may be in the range of 2 to 4, 1 to 3 or 2 to 3, for example.

FIGS. 3A to 3D depict another variation of the delivery system, wherein the implant deployment region 300 comprises a distal includes multiple rotors/stators 302, 304, 306, which may be configured to either unwind the tensioning members 308, 310, 312 at different rates per unit rotation, or in a sequential manner. In the depicted embodiment, the middle rotor/stator 304 on the implant deployment region 300 is configured to unwind a greater length of tensioning member 310 than either proximal or distal rotors/stators 302, 306, to allow the middle section 316 of the implant 314 to expand first or to a greater degree than the ends 318, 320 of the implant 314. This may facilitate positioning of the implant 314 in some procedures at the target location by aligning the expansion of the middle section 316 implant 314 rather than the ends 318, 320, which may be more difficult to align due to foreshortening of the implant 314. This may be provided by configuring the middle rotor/stator 304 with a larger diameter for wrapping around the tensioning members compared to the proximal or distal rotors/stators 302, 206, which increases the length of tensioning member per rotation of the rotor. The length per rotation may also be altered by providing a different number of tensioning members at each rotor/stator. A greater number of tensioning members as they are wrapped around the rotor will result in a larger diameter from all of the coiled tensioning members, which will provide an increased initial length per rotation during deployment. In other examples, multiple drive shafts (not shown) may be provided to independently drive one or more rotors/stators with different amount of rotation relative to one or more other rotors/stators. The multiple drive shafts may comprise a concentric configuration with a solid inner drive shaft for one or more distal rotors/stators, a tubular drive shaft for one or more proximal rotors/stators, for example, or multiple parallel drive shafts, each terminating at a different rotor/stator, for example.

FIGS. 4A to 4D depict still another embodiment of a delivery system 400, wherein the implant deployment region 420 of the catheter includes multiple rotors/stators 422, 424, 426 used to deliver a double-wall stented structure, such as the unibody folded stent heart valve implant 804 as described in U.S. application Ser. No. 17/083,266, which is hereby incorporated by reference in its entirety. In this configuration, the distal rotor/stator 426 is actuated first, before the middle and proximal rotors/stators 422, 424.

Figures 4A, 4B, 4C:
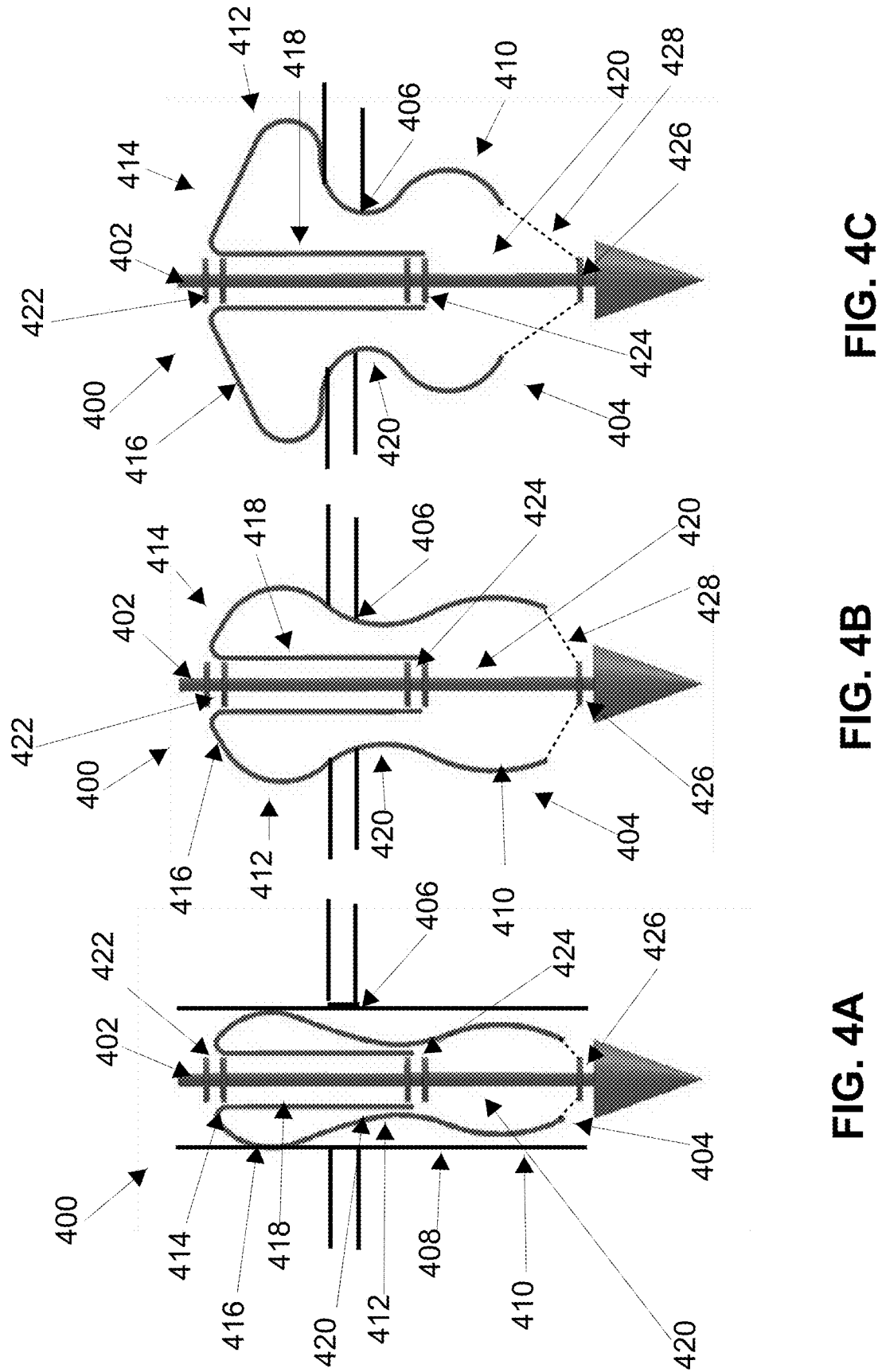
FIGS. 4A to 4E schematically depict another configuration of an exemplary delivery system for a double-wall stent in which the outer wall is expanded before the inner wall.

Referring to FIG. 4A, the delivery system 400 with the delivery catheter 402 and valve 404 is positioned across the mitral valve opening 406. The delivery system 400 may also be further manipulated to adjust the angle of entry through the mitral valve opening 406 to be roughly orthogonal to the native valve opening and/or to be centered with the mitral valve opening 406. Once the desired catheter pose is achieved, the delivery sheath 408 is withdrawn proximally, to expose the collapsed valve 404.

In FIG. 4B, the first set of tension lines 428 controlling the release of the downstream or ventricular end 410 of the outer wall 412 of the valve 404 is partially released, while the tension lines 430, 432 controlling the inner wall 416 remain tensioned. Next, in FIG. 4C, ventricular end 410 of the outer wall 412 of the valve 404 is further released, allowing the ventricular end, the middle region and more of the atrial end 414 of the outer wall 412 to expand further, thereby allowing the transition wall 416 of the valve 402 to at least partially expand outward. The partial expansion of the atrial end 414 and the ventricular end 410 of the valve 402 helps to further center and orient the middle region 422 of the valve 402 orthogonally prior to complete release. While the initial expansion of the atrial end 414 of the outer wall 412 in this embodiment is a secondary effect from the partial release of the ventricular end 410 of the valve 402 as longitudinal tension is released, in other examples, independent tension line control of the atrial end 414 may be provided.

Figures 4D, 4E:
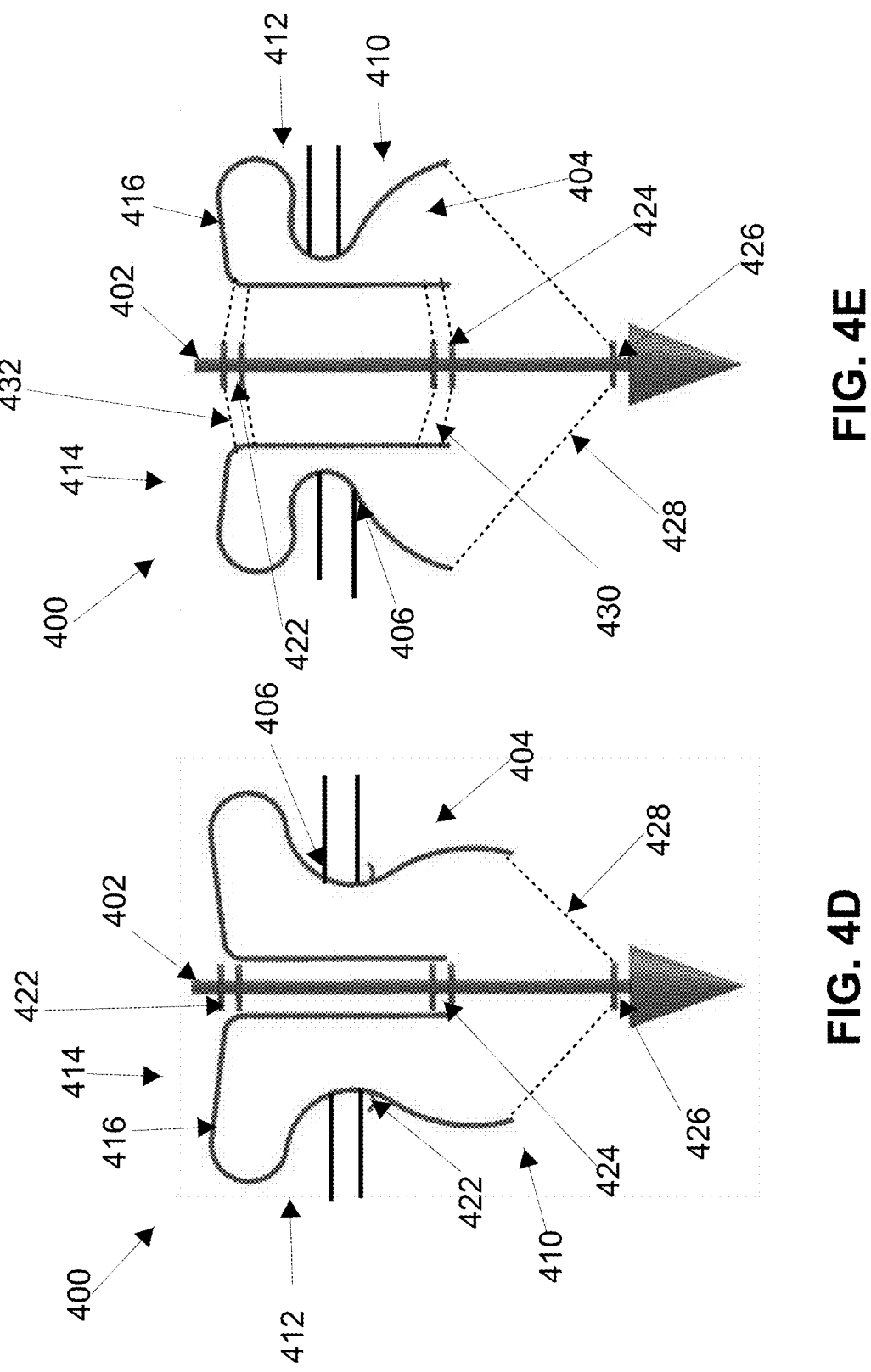

In FIG. 4D, the tension lines of the ventricular end 410 and atrial end 414 are further released, either simultaneously or singly in a stepwise fashion, further engaging the middle region 420 of the outer wall 412 against the valve opening 406. This further expansion of the outer wall 412 also exposes the retention barbs or projections 422 on the outer wall 412. Proper centering and orientation of the valve is reconfirmed, to make sure the valve has not been deployed in a skewed or partially disengaged pose with respect to the mitral valve annulus. In some variations, the tension lines may be re-tensioned to re-collapse the valve 404, to facilitate re-positioning and/or re-orienting of the valve 404. Once confirmed, the tension lines 430, 432 of the inner wall 418 may be released, as shown in FIG. 4E, which also allows the outer wall 412 to achieve its untethered expansion against the mitral valve opening 806. The outer wall 412 may also be expanded first against the valve opening 806, with the tension lines 430, 432 released afterwards. The tension lines 428, 430, 432 can then be cut or otherwise released or separated from the valve implant as described herein and the tension lines 428, 430, 432 may be withdrawn into the catheter and optionally out of the proximal end of the catheter. The delivery catheter and guidewire can then be withdrawn from the patient and hemostasis is achieved at the femoral vein site.

FIGS. 5A to 5D depict still another embodiment of a delivery system 500, wherein the implant deployment region 520 of the catheter includes multiple rotors/stators 522, 524, 526 that are located on the same drive shaft (not shown) and used to deliver a double-wall stented heart valve structure. In this configuration, all three rotors/stators 522, 524, 526 are configured to rotate simultaneously and with equal degrees of rotation, though the length of the tensioning member 428, 430, 432 that is extended or retracted per unit of rotation may be different, depending on the diameter of the rotor and/or the number of tensioning members.

Figures 5A, 5B, 5C:
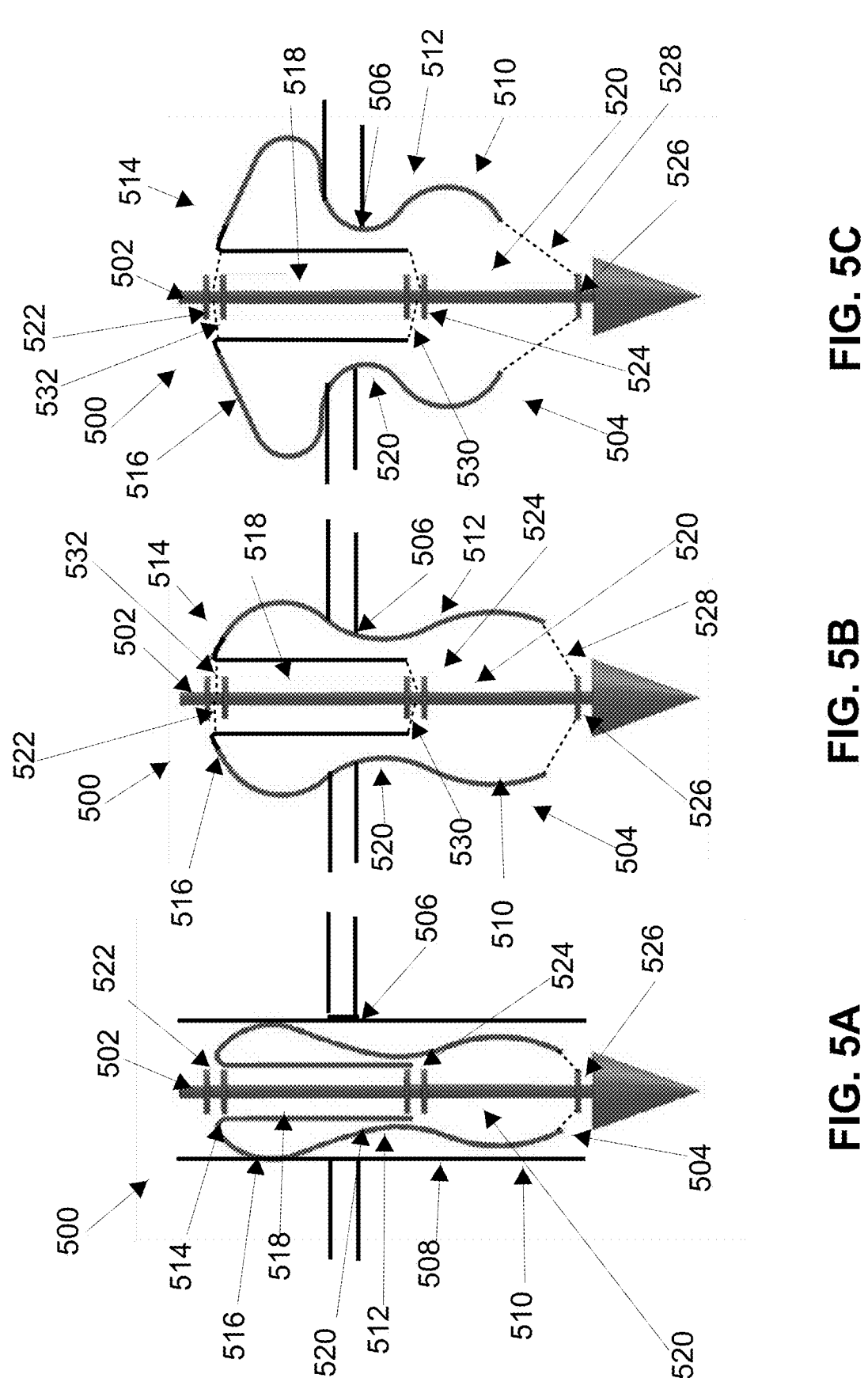
FIGS. 5A to 5E schematically depict another configuration of an exemplary delivery system for a double-wall stent in which the inner and outer walls are expanded simultaneously but at different rates.

Referring to FIG. 5A, the delivery system 500 with the delivery catheter 502 and valve 504 is positioned across the mitral valve opening 506. The delivery system 500 may also be further manipulated to adjust the angle of entry through the mitral valve opening 506 to be roughly orthogonal to the native valve opening and/or to be centered with the mitral valve opening 506. Once the desired catheter pose is achieved, the delivery sheath 508 is withdrawn proximally, to expose the collapsed valve 504.

Figures 5D, 5E:
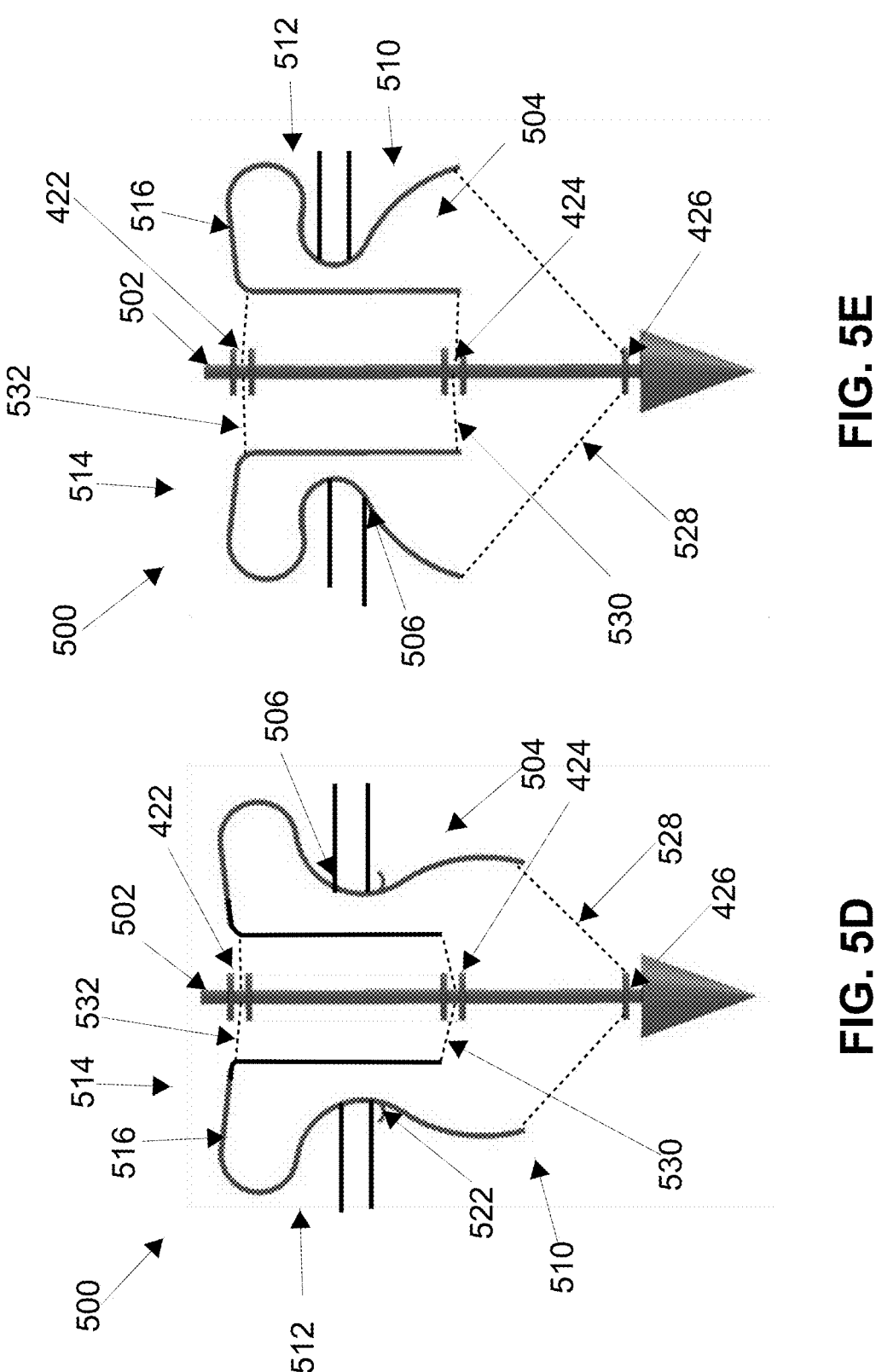

In FIGS. 5B to 5D, all three sets of tension lines 528, 530, 532 controlling the release of the downstream or ventricular end 510 of the outer wall 512 and the inner wall 518 of the valve 504 are simultaneously incrementally released, although tension lines 528 may be configured to release at a greater rate than tension lines 530, 532 due to the greater amount of travel of the ventricular end 510 of the outer wall 512 exhibited during expansion compared the inner wall 518. Next, in FIG. 5C, ventricular end 510 of the outer wall 512 of the valve 504 is further released, allowing the ventricular end, the middle region and more of the atrial end 514 of the outer wall 512 to expand further, thereby allowing the transition wall 516 of the valve 504 to at least partially expand outward. The partial expansion of the atrial end 514 and the ventricular end 510 of the valve 504 in conjunction with the partial expansion of the inner wall 518 helps to further center and orient the middle region 520 of the valve 504 orthogonally prior to complete release. While the initial expansion of the atrial end 514 of the outer wall 512 in this embodiment is a secondary effect from the partial release of the ventricular end 510 of the valve 504 as longitudinal tension is released, in other examples, independent tension line control of the atrial end 514 may be provided.

In FIG. 5D, the tension lines 528, 530, 532 of the ventricular end 510 and inner wall 518 are further released simultaneously, further engaging the middle region 520 of the outer wall 512 against the valve opening 506. This further expansion of the outer wall 512 also exposes the retention barbs or projections 522 on the outer wall 512. Proper centering and orientation of the valve is reconfirmed, to make sure the valve has not been deployed in a skewed or partially disengaged pose with respect to the mitral valve annulus. In some variations, the tension lines may be re-tensioned to re-collapse the valve 504 may be performed, to facilitate re-positioning and/or re-orienting of the valve 504. Once confirmed that the outer wall 512 has achieved its desired expansion against the mitral valve opening 506, as shown in FIG. 5E, the tension lines 528, 530, 532 can then be cut or otherwise released or separated from the valve implant as described herein and the tension lines 528, 530, 532 may be withdrawn into the catheter and optionally out of the proximal end of the catheter. The delivery catheter and guidewire can then be withdrawn from the patient and hemostasis is achieved at the femoral vein site.

Figures 6, 7:
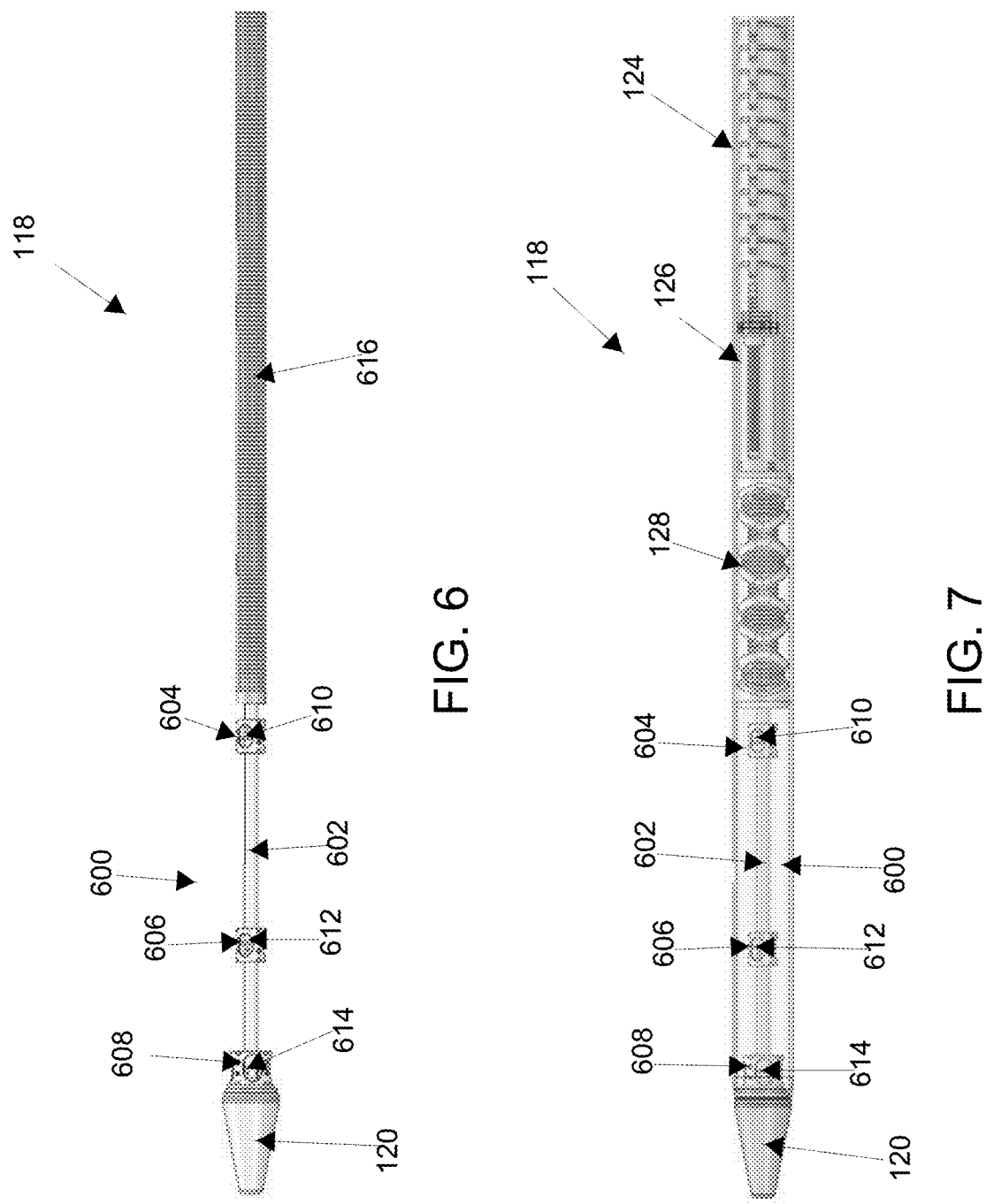
FIG. 6 is a side view of the distal region of the delivery system in FIG. 6, without the sheath or the combination steering and extension assembly.
FIG. 7 is a side cross sectional view of the distal region of the delivery system in FIG. 1.

FIGS. 6 and 7 depict an exemplary detailed configuration of the distal catheter section 118 of the distal delivery system 100 in FIGS. 1A to 1C. As noted previously, the distal catheter section 118 includes a nose cone 120 to facilitate insertion and navigation of the delivery system 100 along the anatomical pathway. The nose cone 120 may include a guidewire lumen and distal opening (not shown) and may comprise a soft atraumatic material such as nylon, polyurethane, or silicone, for example. The nose cone 120 is attached to the stator assembly 600 with at least one stator housing 604, 606, 608 spaced along the stator body 602. Inside the tubular stator body 602 and the stator housings 604, 606, 608 is a rotor body (not shown) with a rotors 610, 612, 614, upon which the elongate tension lines are attached and wound around. Openings in the stator housings 604, 606, 608 permit the tension lines to extend and optionally retract as the rotor body is rotated.

The proximal end of the tubular stator body 602 is attached to a flexible tubular drive shaft casing 616 in which a flexible drive shaft resides. The drive shaft casing 616 may be located within one or more steering and/or positioning assemblies 124, 126, 128 that may be provided in the delivery system 100. In this particular embodiment, a proximal steering assembly 124 is directly coupled at its distal end to a proximal end of a catheter extension assembly 126. In turn, the distal end of the catheter extension assembly 126 is directly coupled to a distal steering assembly 128. Examples of the steering and extension assemblies are described in greater detail below.

Figures 8A, 8B:
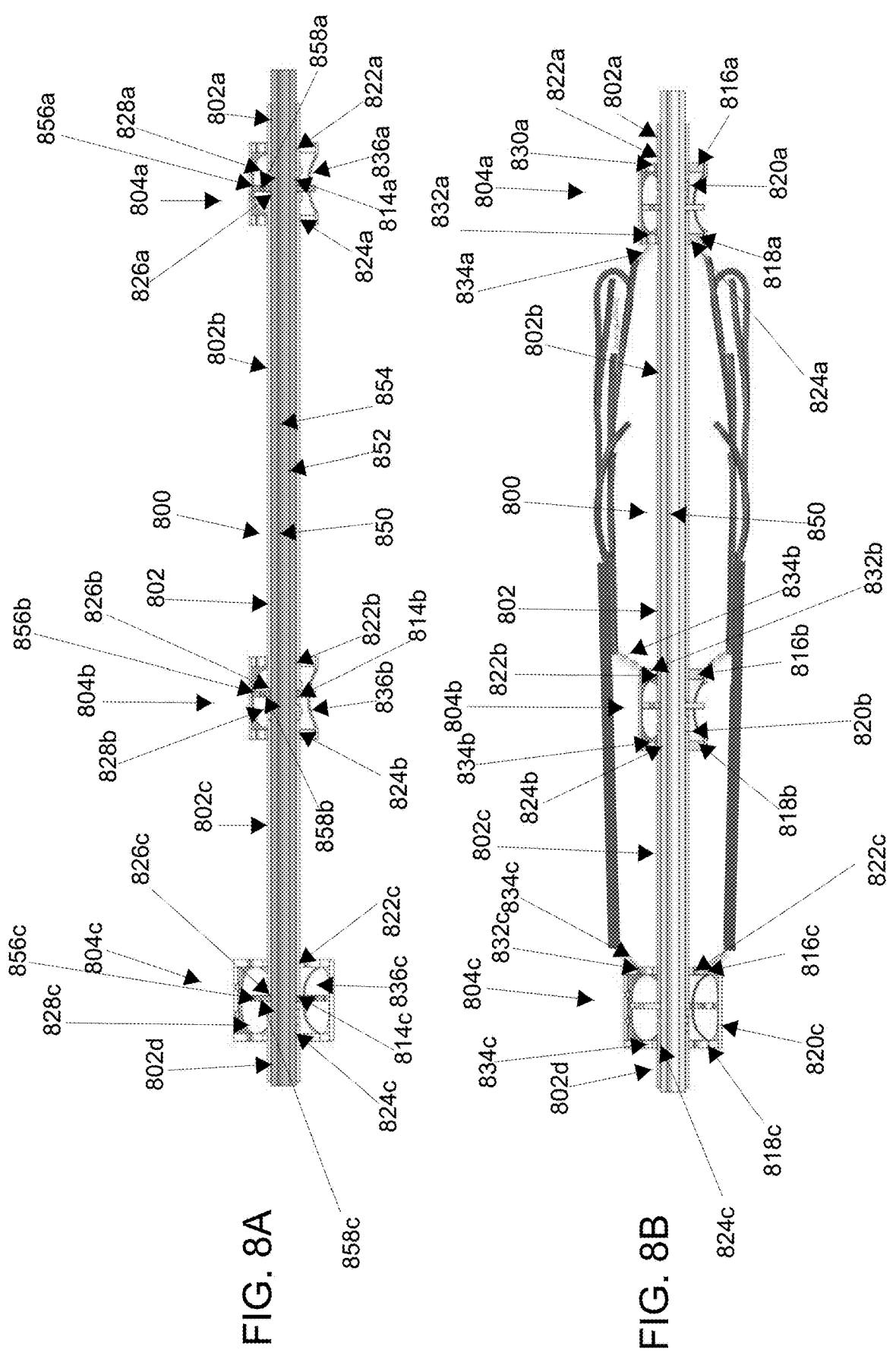
FIGS. 8A and 8B are a side cross sectional views of the rotor and stator region of the delivery system, without and with an exemplary stent structure, respectively.

Referring now to FIGS. 8A and 8B, exemplary embodiments of a stator assembly 800 and a rotor assembly 850 are depicted in greater detail. The stator assembly 800 comprises a tubular stator body 802, comprising a plurality of tubular body segments 802a-d that are connected by stators 804a-c. The lengths of the segments 802a-d may be the same or different. In this particular embodiment, the end segments 802a, 802d have a similar length, while the middle segments 802b, 802c are each longer than the end segments 802a, 802*d* and with the proximal middle segment 802*b* having a greater length than the distal middle segment 802*c*. The segments 802*a-d* form a longitudinal lumen 812 along the length of the stator assembly 800 in which the rotor assembly 850 resides.

Each of the stators 804*a-c* comprises a housing that is generally cylindrical in shape, but may also be configured with other three-dimensional shape shapes, e.g. frustoconical, square box, rectangular box, trapezoidal box, etc. Each stator 804*a-c* comprises a proximal end wall 816*a-c*, a distal end wall 818*a-c*, and a lateral wall 820*a-c*. The proximal end walls 816*a-c* and distal end walls 818*a-c* may include a central opening 822*a-c*, 824*a-c*, respectively, configured to receive a stator body segment 802*a-d*, and an inner opening 826*a-c* through which the rotors of the rotor assembly may project from and into the stator cavities 828*a-c*. As depicted in FIG. 8B, the proximal and distal end walls 816*a-c*, 818*a-c* may also comprise peripheral openings 830*a-c*, 832*a-c* through which the tension lines 834*a-c* may be routed through. The lateral walls 820*a-c* may also comprise one or more lateral openings 836*a-c*.

The rotor assembly 850 comprises a rotor shaft 852 with a longitudinal lumen 854 through which a guidewire may be inserted. Spaced apart on the rotor shaft 852 are rotors 856*a-c* that extend out radially from the rotor shaft 852 at the stator body gaps 814*a-c* located between the stator body segments 802*a-d*. The rotors 856*a-c* may comprise a circular shape as depicted herein, but in other variations, may comprise an oval shape or polygonal shape. Each of the rotors 856*a-c* may comprise one or more attachment structures 858*a-c* for attaching a tension line 834*a-c*. The attachment structures 858*a-c* may comprise an opening through the rotor 856*a-c* that allows the tension line 832*a-c* to be wound around or to be unwound from the rotor 856*a-c*, rotor shaft 852 or tubular body segment 802*b*, 80*c*. The radial distance from the longitudinal axis of the delivery system to the attachment structures 858*a-c* and/or to the peripheral end openings 830*a-c*, 832*a-c* may be configured, depending on the implant configuration and/or angle of the tension lines 832*a-c* as they exit the peripheral end openings 830*a-c*, 832*a-c* during implant expansion. Each of the rotors 856*a-c* and stators 804*a-c* may have more than one tension line 832*a-c* attached to it, and each of the tension lines may have a different length. For example, rotor 856*c* may have four tension lines 832*c* attached, which each tension line 832*c* exiting the stator 804*c* at a different end opening 830*c* and spaced 90 degrees apart from each other, while rotors 804*a* and 804*b* may be configured with three tension lines 832*a*, 832*b* each, spaced 120 degrees apart but wherein tension lines 832*a* and 832*b* have a different line length, which may result from different degrees of expansion along the implant. In other variations of the delivery system, the one, two or four rotors/stators may be provided, and the number of tension lines for each rotor/stator may be one, two, five, six, seven, eight, nine, twelve or any range therebetween. The lengths of each tension line or tension loop may be 10 mm to 70 mm, 15 mm to 60 mm, or 20 mm to 40 mm. The diameter of a stator body may be in the range of 2 mm to 8 mm, 3 mm to 5 mm or 6 mm to 8 mm. As noted previously, the distal stator may comprise different diameter than the other stators, in the range of 5 mm to 10 mm, 6 mm to 8 mm, or 6 mm to 7 mm. The proximal and/or middle stator may comprise a diameter in the range of 3 mm to 8 mm, 4 mm to 6 mm, or 4 mm to 5 mm. The radial distance from the longitudinal axis to the attachment structure of a rotor may be in the range of 0.7 mm to 3.75 mm, 1 mm to 2.9 mm, or 1.5 mm to 2 mm.

FIGS. 9A to 9F illustrates another variation of a rotor assembly 900, comprising a tubular shaft 902, a proximal rotor 904*a*, a middle rotor 904*b* and a distal rotor 904*c*. Each rotor 904*a-c* comprises a mount, ring or tubular body 906*a-c* to couple to the shaft 902, with a disc-like flange 908*a-c*. Each mounting ring 906*a-c* includes a central opening 910*a-c* to receive the shaft 902 and may include one or more optional sidewall openings 912*a-c* which may be used to facilitate the bonding of the rotors 904-*ac*. The distal rotor 904*c* has a larger flange 908*c* than the flanges 908*a*, 908*b* of the proximal and middle rotors 904*a-b*. The larger size allows a greater number of tension lines to be attached. Each flange 908*a-c* comprises one or more attachment structures for the attachment of the tension lines. The attachment structures may comprise projections or openings on the flange 908*a-c*. In the particular embodiment depicted in FIGS. 9A to 9F, the distal flange 904*c* comprises four sets of apertures 914*a-d*, with each set comprising a larger oblong opening 916*a* along the outer diameter of the flange 908*c*, and along with three smaller openings 916*b-d* along the inner diameter of the flange 908*c*, with the larger opening 916*a* symmetrically radially aligned with the smaller openings 916*b-d*. Each of the aperture sets 914*a-d* is equally spaced 90 degrees apart around the flange 908*c*, but in other examples may have a non-uniform spacing, or spacing that is bilaterally symmetrical but not circumferentially symmetrical.

In this particular embodiment, the proximal and middle flanges 908*a*, 908*b* of the rotors 904*a*, 904*b* have the same shape but are mounted on the rotor shaft 902 with their mounting rings 906*a*, 905*b* away from the other, with the proximal rotor mounting ring 906*a* located proximal of its flange 908*a*, while the middle rotor 904*b* has a mounting ring 906*b* that is distal to its flange 908*b*. The distal mounting ring 906*c* is also distal to its flange 908*c*. In other examples, however, one or more of the rotors may have the opposite orientation. In still other variations, the rotor may comprise a different configuration, e.g. with two flanges, or two or more mounting ring sections on each side of each flange.

The length of the rotor shaft 902 may be in the range of about 10 mm to 80 mm, 20 mm to 65 mm or 35 mm to 45 mm. The distance between any two adjacent rotors may be in the range of about 5 mm to 60 mm, 10 mm to 50 mm or 20 mm to 30 mm. In embodiments with a middle rotor, the distance between the proximal rotor and middle rotor may be in the range of about 5 mm to 40 mm, 7 to 30 or 10 mm to 15. The distance between the middle rotor and the distal rotor may be in the range of about 25 mm to 30 mm, 20 mm to 40 mm or 10 mm to 60 mm. The thickness of each rotor may be in the range of about 0.35 mm to 0.40 mm, 0.3 mm to 0.5 mm or 0.2 mm to 0.6 mm.

The outer diameter of the rotor shaft 902 may be in the range of about 1 mm to 3 mm, 1.2 mm to 2 mm or 1.4 mm to 1.8 mm, while the diameter of the internal lumen 918 of the rotor shaft 902, if provided, may be in the range of about 0 mm to 1.5 mm, 0.5 mm to 1.2 mm or 0.80 mm to 1.0 mm. The diameter of the mount or ring 904*a-c* may be in the range of about 1.2 mm to 3.5 mm, 1.6 mm to 3.0 mm or 2.0 mm to 2.4 mm. The diameter of the rotor flange 908*a-c* may be in the range of about 2 mm to 9 mm, 4 mm to 7 mm or 2 mm to 5 mm, 3.5 mm to 4.5 mm, 5 mm to 6 mm, 4.5 mm to 7 mm.

Referring now to FIGS. 10A to 10F, the stator assembly 1000 may comprise a tubular stator shaft 1002, which itself may comprise one or more tubular shaft segments 1002*a-d*, which are connected in a spaced apart fashion by corresponding proximal, middle and distal stator housings 1004*a*-*c*, respectively. In this particular embodiment, the proximal and middle stator housings 1004*a*, 1004*b* have the same size and configuration, while the distal stator housing 1004*c* comprises a larger size and a different configuration. Each stator 1004*a*-*c* may comprise a generally cylindrical shape, with a proximal or first end wall 1006*a*-*c*, distal or second end wall 1008*a*-*c* and cylindrical or lateral wall 1010*a*-*c* therebetween, but in other variations may comprise a frustoconical shape, oval or oblong shape, square box shape, rectangular box shape, triangular box shape or other polygonal box shape. The end walls 1006*a*-*c*, 1008*a*-*c* each comprise three or four oval or oblong openings 1014*a*-*c*, 1016*a*-*c*, respectively, that are equally spaced around the center openings 1018*a*-*c*, 1020*a*-*c* in which the stator shaft segments 1002*a*-*d* are located. The cylindrical walls 1010*a*-*c* of the housings 1004*a*-*c* comprise three or four larger oval openings 1018*a*-*c* with two longitudinally aligned smaller circular openings 1020*a*-*c* located between each of the larger oval openings 1018*a*-*c*. The number of openings may correspond with the number tensioning members provided at each location, e.g. three tensioning members at each of the smaller stator housings with three openings, and four tensioning members at the larger stator housing with four openings. The larger oval openings 1018*c* are equally spaced apart at 90 degrees, and each of the smaller pairs of openings 1020*c* are also equally spaced apart at 90 degrees. Of course, in other variations, a different number of the end and cylindrical wall openings may be provided on each wall 1006*a*-*c*, 1008*a*-*c*, 1010*a*-*c*, e.g. one, two, three four, or five of each type of opening, and the openings may or may not equally spaced apart. Each of the stator housings 1004*a*-*c* is configured with a cavity 1022*a*-*c* that is of a sufficient size to allow receive and to permit rotation of the corresponding rotor, and manufactured with shaft segment gaps 1024*a*-*c* to also receive and to permit rotation of the corresponding rotor. The end walls 1006*a*-*c*, 1008*a*-*c* and the cylindrical walls 1010*a*-*c* may also comprise one more projections 1026*a*-*c* and/or recesses 1028*a*-*c* to provide a mechanical or friction fit to facilitate assembly of the stator housings 1004*a*-*c*.

The length of the stator shaft 1002, including the shaft segment gaps 1024*a*-*c*, may be in the range of about 25 mm to 80 mm, 40 mm to 70 mm or 55 mm to 65 mm. The stator shaft 1002 length may be longer or shorter than the rotor shaft length, and the difference in rotor/stator shaft length may be in the range of about ±0.2 mm to ±3 mm, 0.4 mm to 2 mm or 0.4 mm to 0.8 mm. The outer diameter of the stator shaft may be in the range of about 1.6 mm to 3.3 mm, 1.7 mm to 3 mm or 1.8 mm to 2.5 mm, while the diameter of the stator internal lumen may be in the range of about 1.6 mm to 3.3 mm, 1.7 mm to 3 mm or 1.8 mm to 2.5 mm. The various distances between the stators may otherwise be similar to the various distance ranges as recited above for the distances for the corresponding rotors. The outer length of the stator housings may be in the range of about 3 mm to 8 mm, 4 mm to 7 mm or 5 mm to 6 mm, and the outer diameters of the stator housings may be in the range of about 4 mm to 5 mm, ***6 mm to 7 mm, 2 mm to 8 mm, 5 mm to 9 mm, or 3 mm to 8 mm. The internal cavities of the stator housings may have a length in the range of about 3 mm to 5 mm, 3 mm to 6 mm or 4 mm to 5 mm, and a diameter in the range of about 4 mm to 6 mm, 3 mm to 5 mm, 5 mm to 7 mm, 4 mm to 7 mm, 3 mm to 8 mm, 4 mm to 9 mm. The shaft segment gaps lengths may be in the range of about 1 mm to 4 mm, 1 mm to 3 mm or 1.5 mm to 2.5 mm.

Figures 10A, 10B, 10C, 10D, 10E, 10F:
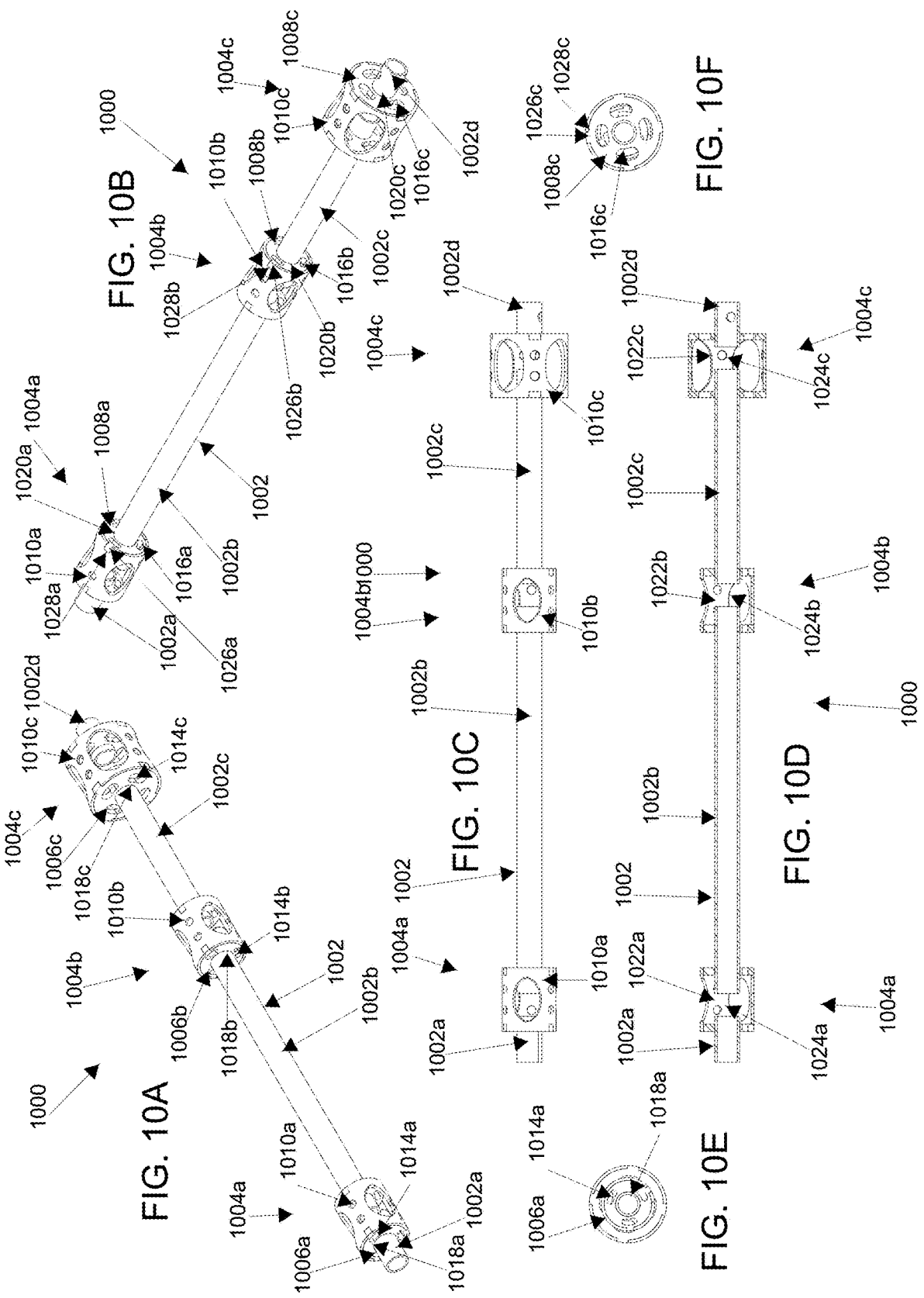
FIGS. 10A and 10B are front and rear perspective views of the stator shaft.
FIGS. 10C and 10D are side elevational and side cross-sectional views of the stator shaft in FIGS. 10A and 10B.
FIGS. 10E and 10F are front and rear elevational views of the stator shaft in FIGS. 10A and 10B.
Figure 10G:
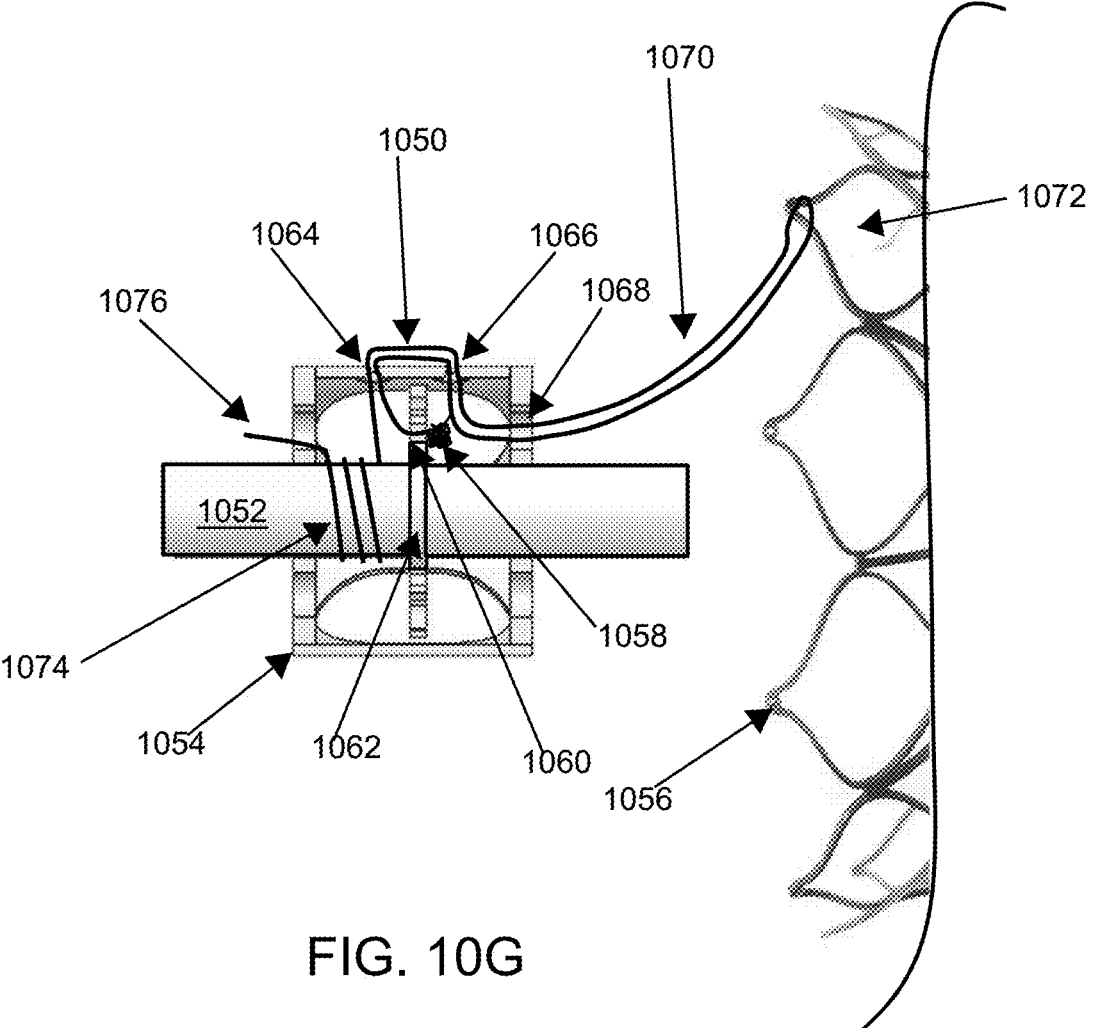
FIGS. 10G and 10H are schematic cutaway views of a rotor/stator structure depicting an exemplary configuration of the routing of a tensioning member in an engaged and released configuration to a rotor/stator and a stent structure.

FIG. 10G is a schematic illustration of the routing configuration for a tensioning member 1050 about a rotor 1052, stator housing 1054 and a stent 1056. For clarity, only one of the multiple tensioning members that would be spaced around at different angular positions of the rotor/stator location is shown. A first end 1058 of the tensioning member 1050 is knotted or otherwise attached to an opening 1060 of the rotor flange 1062 to resist separation from the rotor 1052. The tensioning member 1050 is then routed out of a first stator opening 1064 and into a second stator opening 1066 on the other side of the rotor flange 1062 and out of an end opening 1068 of the stator 1056. The tensioning member 1050 would then extend out and as a loop segment 1070 through an opening 1072 of the stent 1056, or multiple such openings and then route back into the end opening 1068, the second stator opening 1066 and the first stator opening 1064. The tensioning member 1050 would then be wrapped around the rotor 1052 two, three, four, five or more times forming coils 1074, along with the other tensioning members at that location, even wrapping around itself and/or other tensioning members. This number of wrapped loops or coils provides sufficient frictional resistance so to resist unwrapping or slippage from the expansion force of the stent 1056, depending on the tensioning member material. The other, free end 1076 of the tensioning member 1050 may extend out of the opposing end opening 1076 of the stator 1054.

Figure 10H:
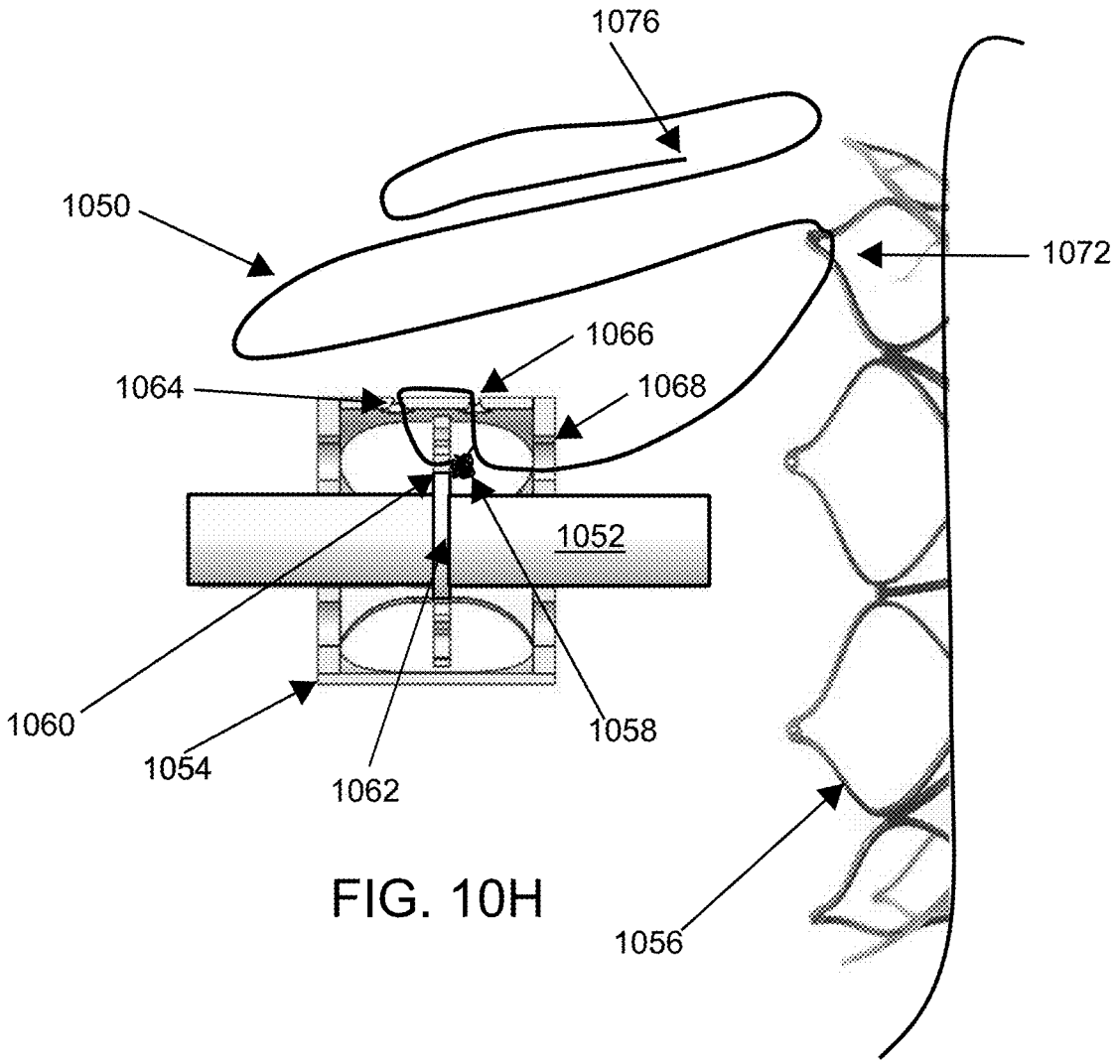

When the stent 1056 is in a collapsed state, most of the tensioning member 1050 will be within the stator 1054 or in contact with the stator 1054, wrapped around the rotor 1052. As the rotor 1052 is rotated to unwind or unwrap the tensioning member 1050 from the stator 1052, the tensioning member 1050 will slide along its routing path to extend the loop segment 1070 through the end opening 1068, which permits the stent to further expand. In FIG. 10H, as the tensioning member 1050 further unwraps from the rotor 1052, the friction between the rotor 1052 and the coils 1074 of the tensioning member 1050 will decrease to a point where the free end 1076 of the tensioning member 1050 is able to disengage and be pulled out of from the rotor 1052 and out of the stator 1054. Further rotation of the rotor 1052 will begin to recoil or rewrap the tensioning member 1050 beginning at the attached or knotted end 1058 of the tensioning member 1050 until the free end 1076 is pulled out of the stent 1056. In other variations, as long as the free end 1076 has been released from the rotor 1052 and stator 1054, the further rotation of the rotor 1052 is not performed to partially recoil or fully recoil the tensioning member 1050 before the delivery system is withdrawn. Instead, the tensioning member 1050 can be fully separated from the stent 1056 by withdrawing the delivery system with the tensioning member 1050 still extending out from the stator 1054.

Figures 10I, 10J:
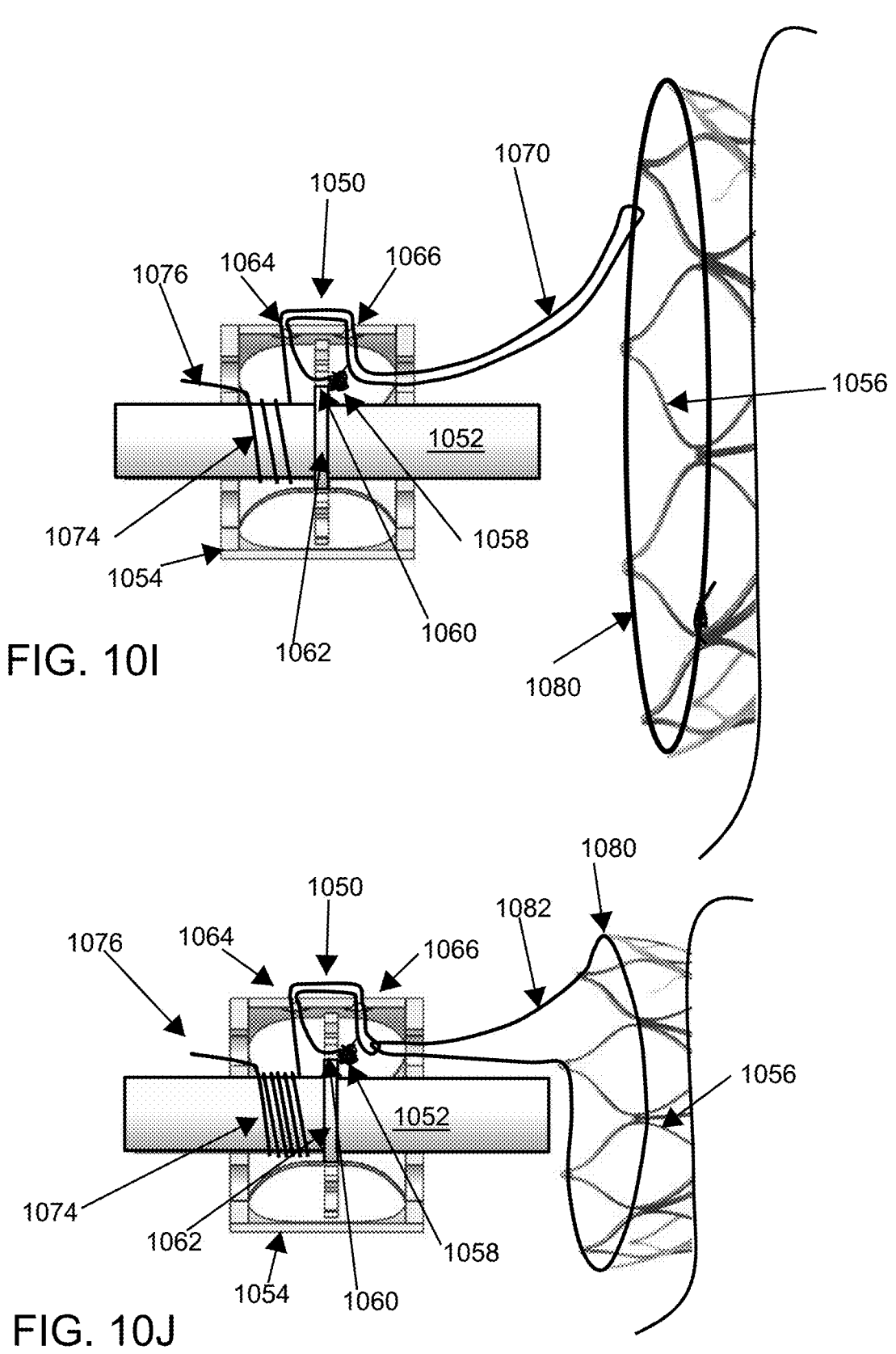
FIGS. 10I and 10J are schematic cutaway views depicting another configuration of the routing of a tensioning member to a rotor/stator structure and a suture loop attached to a stent structure, in an expanded and collapsed state.

FIGS. 10I and 10J depicts another variation of the attachment of the tensioning member 1050 to the stent 1056. This variation is similar to the prior variation in FIGS. 10G and 10H, except that instead of the tensioning member 1050 looping through an opening 1072 of the stent 1056, the stent 1056 further comprises a flexible suture or attachment loop 1080 located around one or more circumferences of the stent 1056. The attachment loop 1080 is permanently attached to the stent 1056 and is left with the stent 1056 after the delivery system is withdrawn. The attachment loop 1080 may comprise the same or different material as the tensioning member 1050. The tension members and the attachment loop may comprise a monofilament or a multifilament man ultra high molecular weight polyethylene, including but not limited to nylon, polyethylene, FORCE FIBER® suture (TELEFLEX MEDICAL, Gurnee, IL), liquid crystal polymer suture, including but not limited to VECTRAN™ (KURARAY AMERICA, Tokyo, Japan), braided aramid fiber, including but not limited to KEVLAR® (DUPONT™, Wilmington, DE), multi-strand metal wire, including but not limited to stranded stainless steel wire rope and tungsten wire rope, for example. The attachment loop 1080 may be configured with a net length that is or corresponds to the circumference of the stent 1056 when at its full expansion size, within 5%, 10%, 15%, 20% or 25% of the circumference. As shown in FIG. 10J, as the stent collapses into its delivery configuration, the a portion 1082 of the attachment loop 1080 that is attached to the loop 1070 of the tensioning member 1050 is able to be pulled away from the stent 1056 and can invaginate or be pulled into the stator housing 1056 or even coiled around the rotor 1052. In some variations, the use of an attachment loop 1080 on the stent 1056 may provide a more predictable coiling, release or other interactions with the tensioning member 1050, by allowing the tensioning member 1050 to slide along the circumference of the loop, rather than restricting its attachment at a specific location of the stent 1056. This may reduce the risk of unintended snagging or cutting or the tensioning members during loading or delivery, and/or uneven tensioning forces between different tensioning members during loading or delivery.

Figures 11, 12:
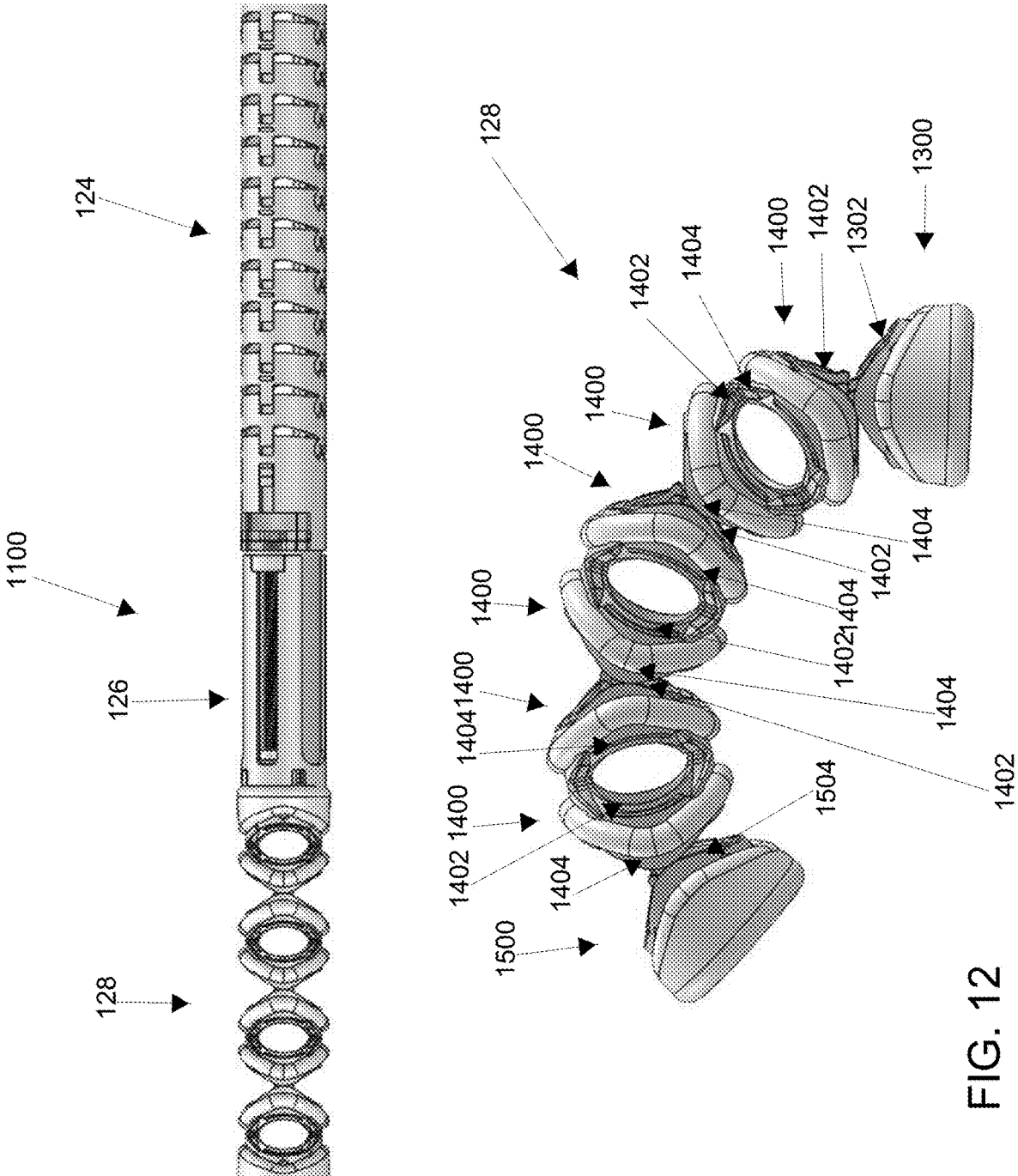
FIG. 11 is a side elevational view of the steering and extension assembly of the delivery system in FIG. 1.
FIG. 12 is a side elevational view of the distal steering assembly of FIG. 11, in a bent configuration.
Figures 13A, 13B, 13C, 13D, 13E, 13F:
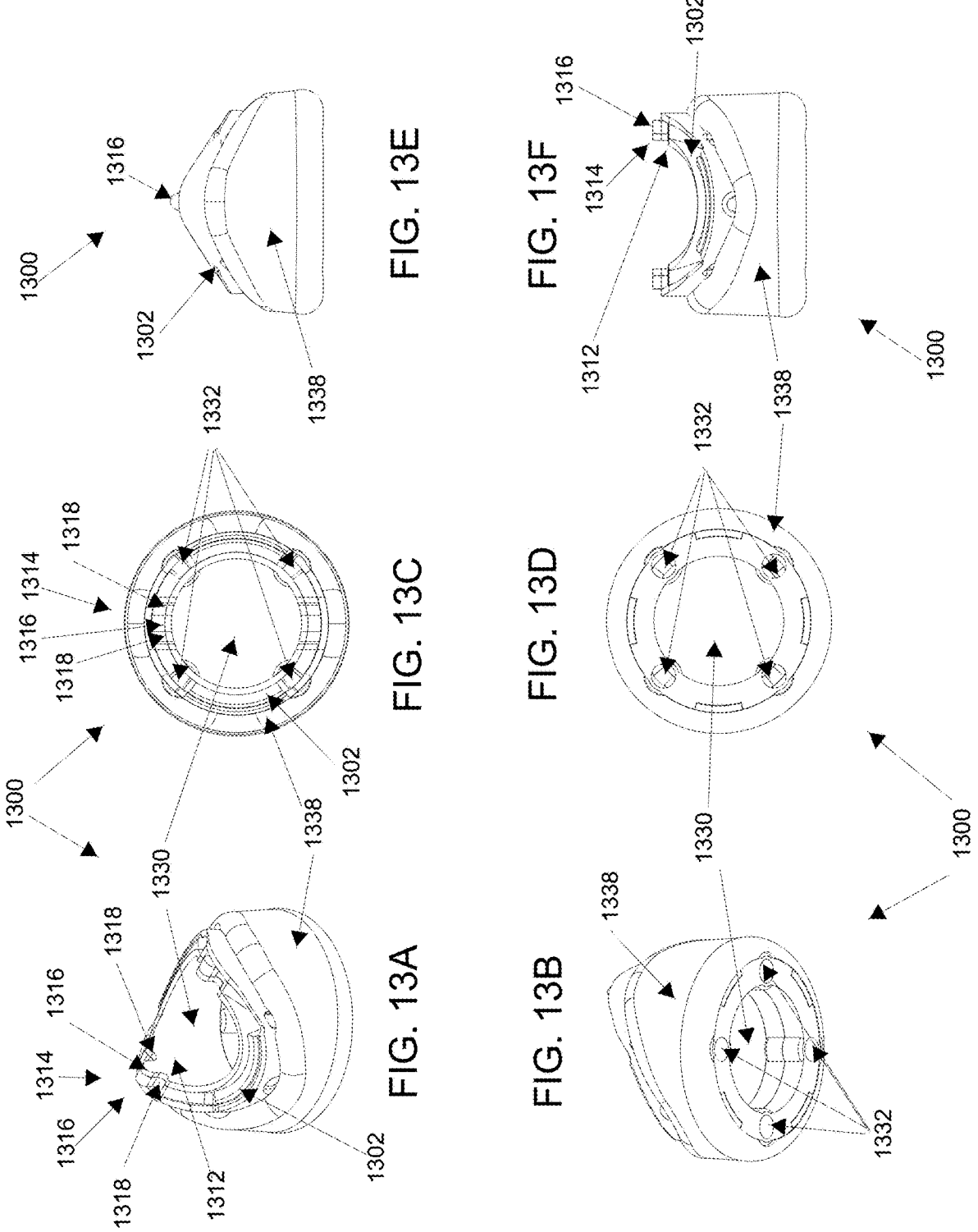
FIGS. 13A to 13F are top perspective, bottom perspective, top plan, bottom plan, side elevational and front/rear elevational views, respectively, of the proximal segment of the distal steering assembly in FIG. 12, with perimeter bumpers.
Figures 13G, 13H, 13I, 13J, 13K, 13L:
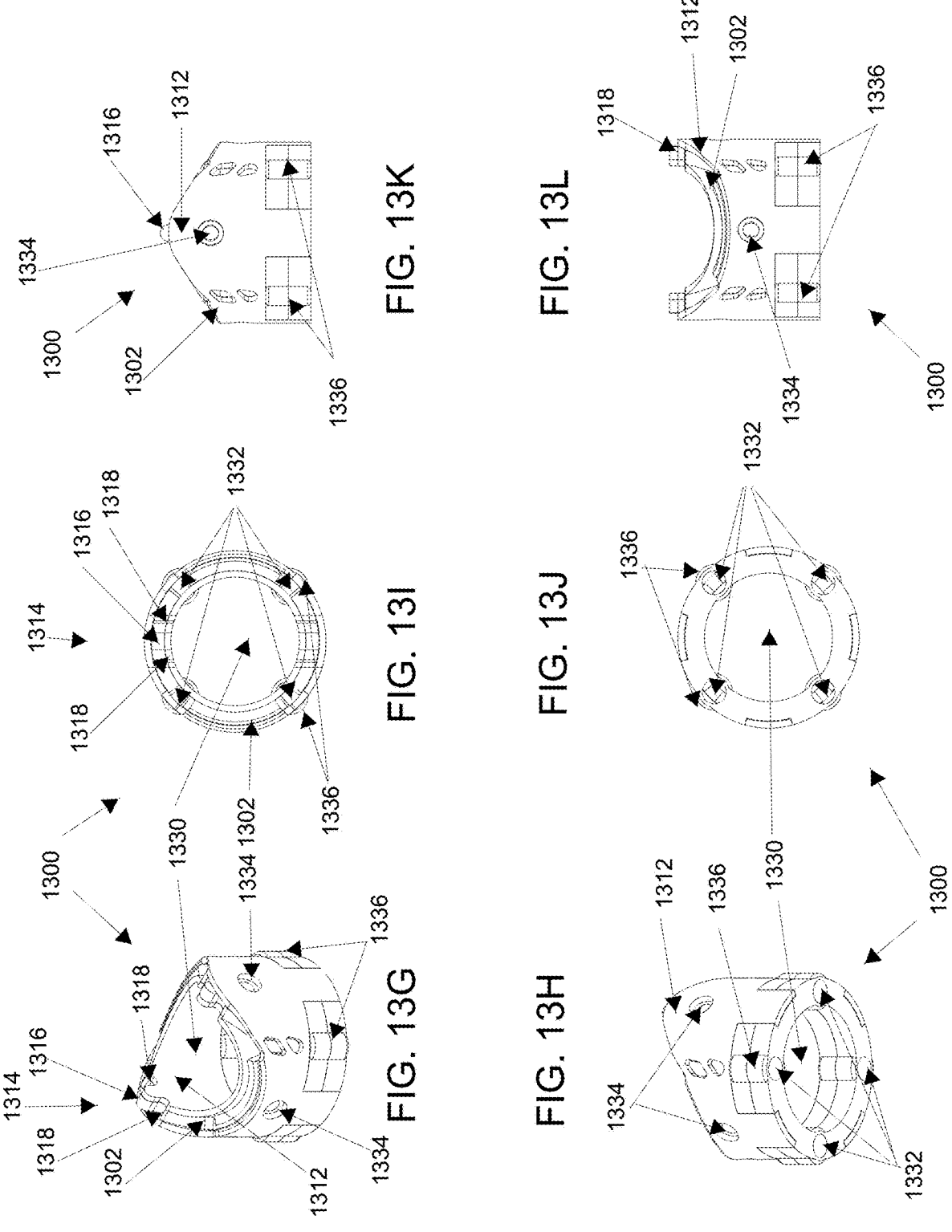
FIGS. 13G to 13L are top perspective, bottom perspective, top plan, bottom plan, side elevational and front/rear elevational views, respectively, of the proximal segment of the distal steering assembly in FIG. 12, without perimeter bumpers.
Figures 14A, 14B, 14C, 14D, 14E, 14F:
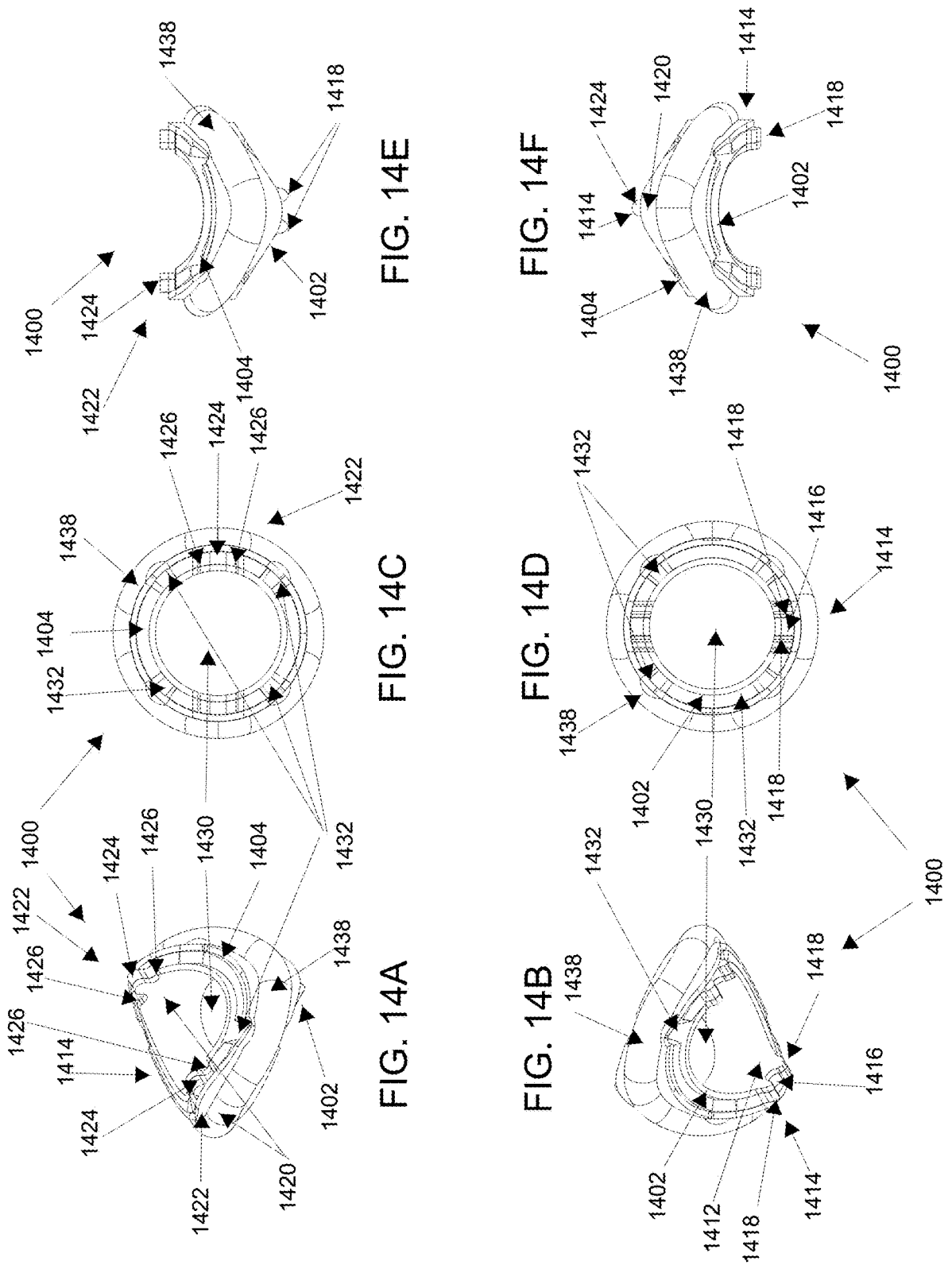
FIGS. 14A to 14F are top perspective, bottom perspective, top plan, bottom plan, side elevational and front/rear elevational views, respectively, of the middle segments of the distal steering assembly in FIG. 12, with perimeter bumpers.
Figures 14G, 14H, 14I, 14J, 14K, 14L:
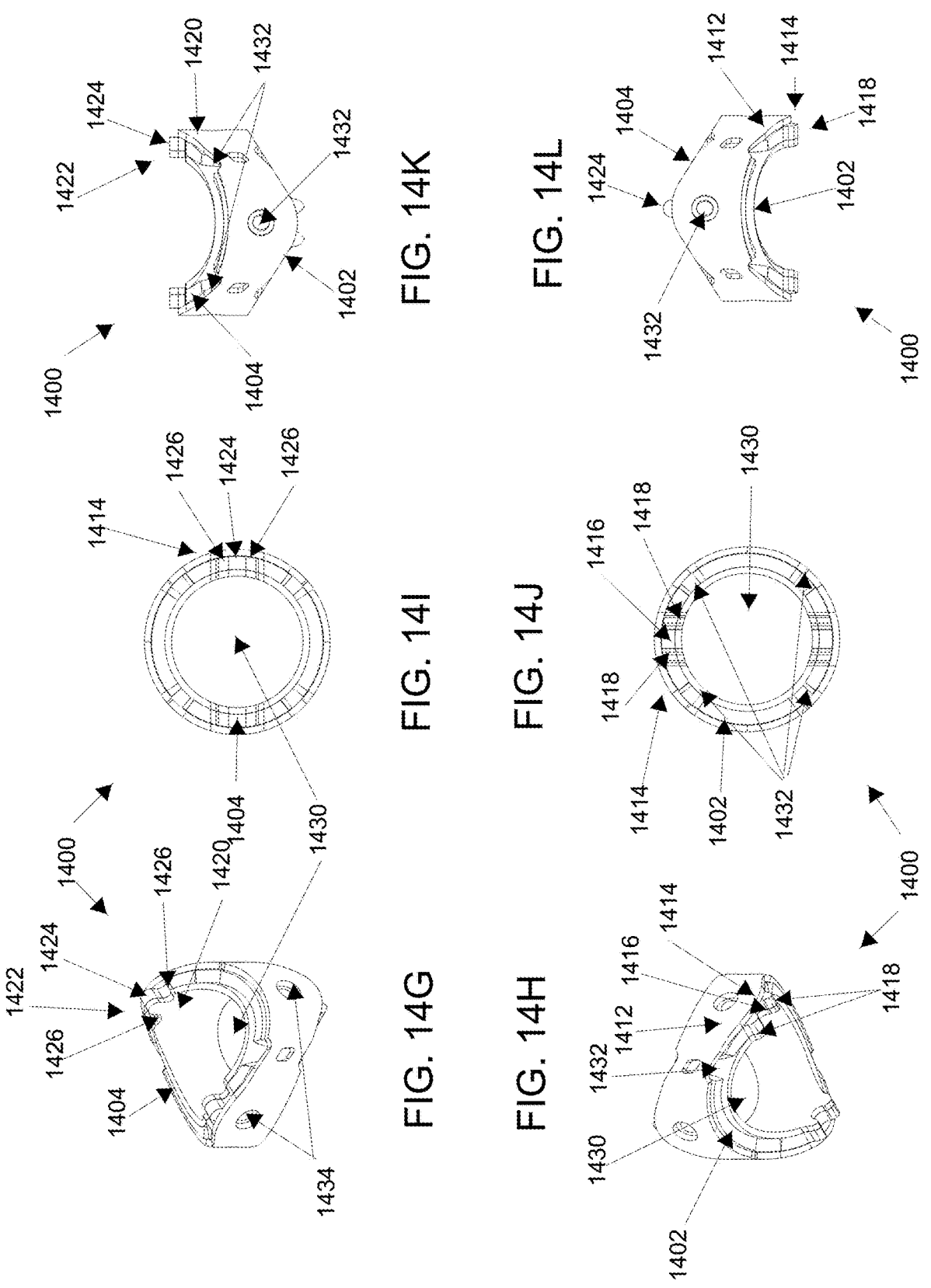
FIGS. 14G to 14L are top perspective, bottom perspective, top plan, bottom plan, side elevational and front/rear elevational views, respectively, of the middle segments of the distal steering assembly in FIG. 12, without perimeter bumpers.
Figures 15A, 15B, 15C, 15D, 15E, 15F:
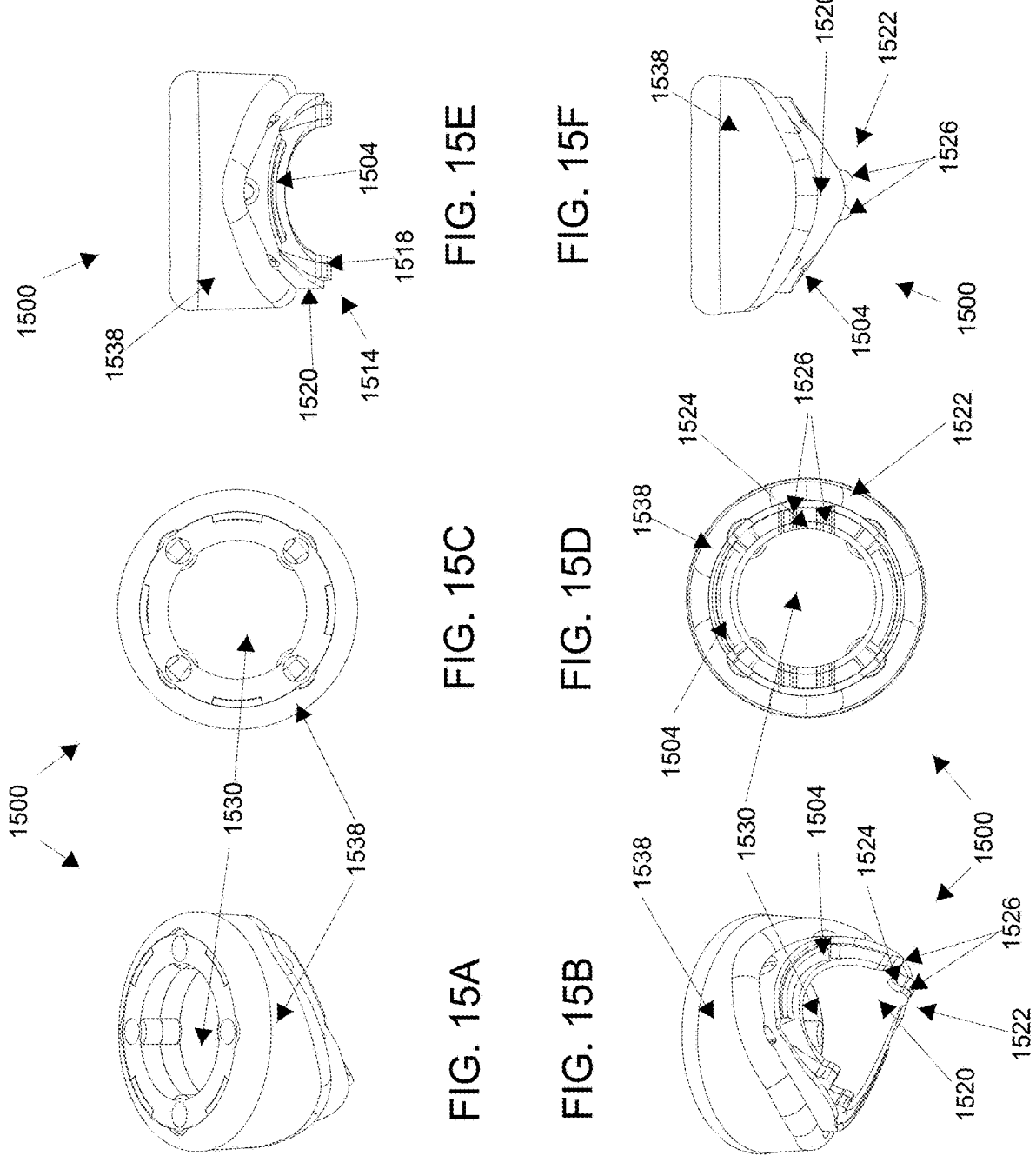
FIGS. 15A to 15F are top perspective, bottom perspective, top plan, bottom plan, side elevational and front/rear elevational views, respectively, of the distal segment of the distal steering assembly in FIG. 12, with perimeter bumpers.
Figures 15G, 15H, 15I, 15J, 15K, 15L:
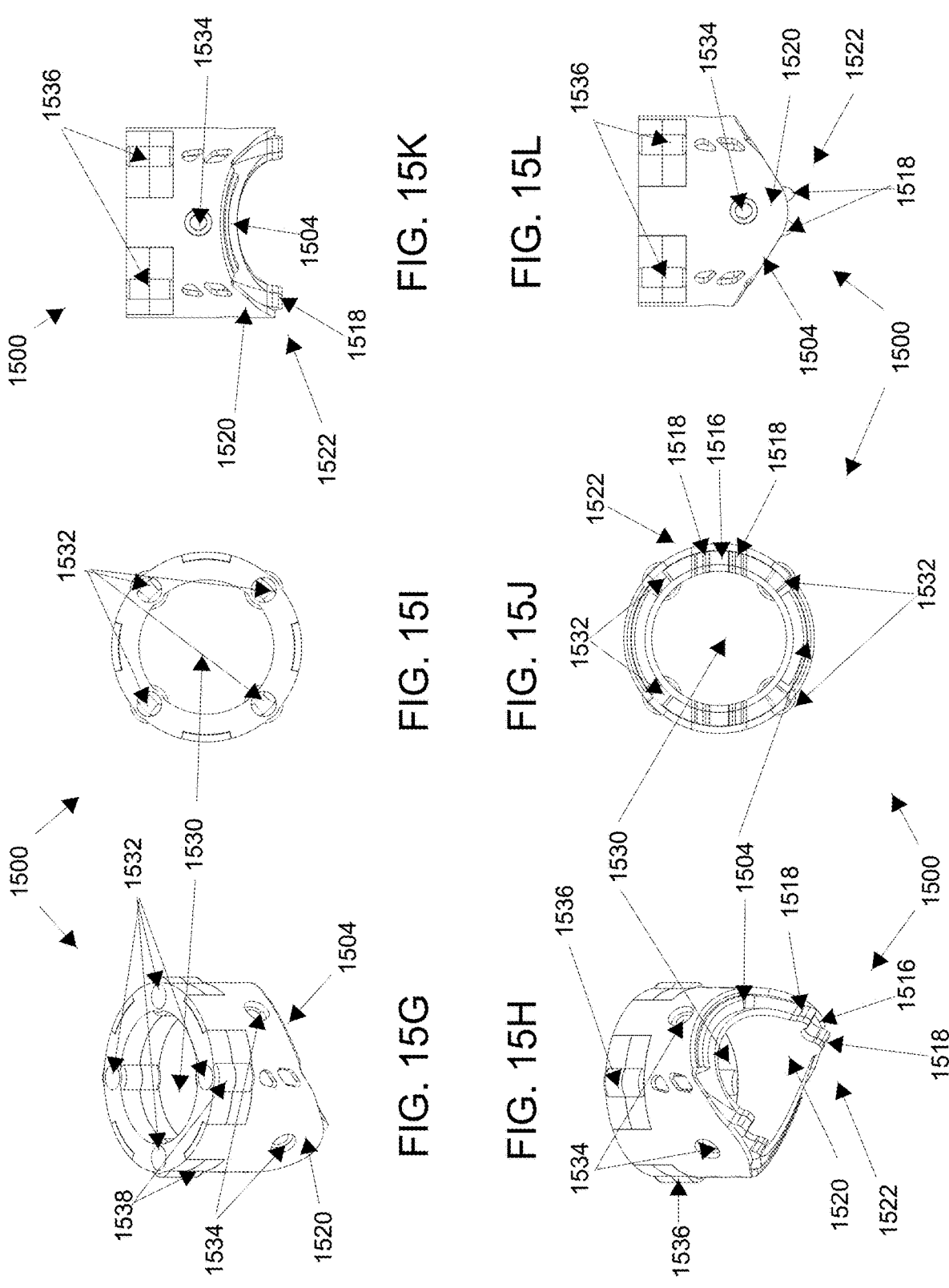
FIGS. 15G to 15L are top perspective, bottom perspective, top plan, bottom plan, side elevational and front/rear elevational views, respectively, of the distal segment of the distal steering assembly in FIG. 12, without perimeter bumpers.

As noted previously, in some variations, one or more steering or catheter extension assemblies may be provided to facilitate navigation of the delivery system and/or positioning and orienting the delivery section or implant during the procedure. In embodiments with two or more of such assemblies, the assemblies may be spaced apart along the delivery system, or as shown in FIG. 11, the assemblies 124, 126, 128 may be subassemblies that are directly attached end-to-end, as a single assembly 1100. In this particular embodiment, assemblies 124, 128 are bending or steering assemblies that are configured to bend the delivery system along one or multiple axes. In this example, the proximal bending assembly 124 is a two-way bending assembly that it is configured to bend in a single plane in two opposite directions, while the distal bending assembly 128 is a four-way bending assembly in that it is bends in at least two planes and optionally in combinations of the bends in the two planes, e.g. multi-axial steering/bending. Between the two steering assemblies 124, 128 is an extension assembly 126 that is configured to reversibly adjust its length or spacing between its proximal and distal ends. This allows the user to make incremental changes to the longitudinal positioning of the distal region of the delivery system, without requiring longitudinal displacement of the entire delivery system. Although this particular configuration comprises two different configurations of steering assemblies, in other variations, the steering assemblies may comprise the same configuration, or the order of the steering assemblies may be reversed, and/or the extension assembly may be located before or after the two steering assemblies.

Referring to FIGS. 12-15L, the distal steering assembly 128 may comprise a segmented tubular or ring configuration, with each segment 1300, 1400, 1500 comprising one or two segment interface ends, depending on the location of the segment 1300, 1400, 1500 in the assembly 128. In the depicted example of FIGS. 1A-1C, the distal steering assembly 128 may be controlled by a joystick controller 108 on the handle 102, as described in greater detail below. Referring back to FIGS. 12 to 15L, the proximal and distal segments 1300, 1500 each comprise a segment interface end 1302, 1504 which is configured to interface with a segment interface end 1402, 1404 of a middle segments 1400. The interface ends 1402, 1404 are also configured to interface with the complementary other configuration of end 1402, 1404 of another middle segment 1400. The segment interface ends 1302, 1402, 1404, 1504 are configured as a single-axis, two-way bend at each articulation between the interface ends 1302, 1402, 1404, 1504 but with the distal steering assembly 128 comprising interfaces with different orientations, e.g. one set of interfaces 1302, 1402 having an orthogonal orientation to the other set of interfaces 1404, 1504, the assembly 128 as a whole is configured as a four-way, two axis bending assembly.

Referring to FIGS. 13A-13F, 14A-14F, and 15A-15F, the proximal and distal segments 1300, 1500 comprises a non-planar end 1302, 1504 that has a hyperbolic paraboloid shape that is configured to interface with a complementary non-planar end 1402, 1404 of a middle segment 1400 that also has a hyperbolic paraboloid shape. The non-planar end 1402 of the middle segment 1400 is also configured to interface with the non-planar end 1404 of another middle segment 1400. At the upper regions 1312 of the end 1302, an alignment structure 1314 may be provided to interface with an alignment structures 1414 at the upper regions 1412 of the complementary end 1402 of the middle segment 1400. In this particular variation, the alignment structure 1314 comprises a middle protrusion 1316 flanked by indents or recesses 1318 which forms a complementary interface with the alignment structure 1416 of the middle segment 1400, which comprises a middle recess 1418 flanked by protrusions 1418. Likewise, the upper regions 1420 of the other end 1404 of the middle segment 1400 comprises an alignment structure 1422 with a middle protrusion 1424 flanked by indents or recesses 1426 that can also form a complementary interface with the alignment structure 1404 of the middle segment 1400, and also the alignment structure 1522 in the upper regions 1520 of the non-planar end 1504 of the distal segment 1500. The alignment structures 1522 on the distal segment 1500 are the same or similar to the alignment structure 1422 of the middle segment 1400, with a middle recess 1524 flanked by two protrusions 1526. The alignment structures 1314, 1414, 1422, 1522 are configured to still provide a limited amount of pivoting between the segments 1300, 1400, but do not lock the two segments 1300, 1400 together. In other variations, however, the alignments structures 1314, 1414, 1422, 1522 may comprise complementary ball-in-socket structures or other type of complementary interference structures that does lock the segments 1300, 1400 together. Also, in other variants, instead of a hyperbolic paraboloid shape, the non-planar ends 1302, 1402, 1404, 1504 may comprise two planar sections that are non-orthogonal to the longitudinal axis of the bending assembly 128.

Referring still to FIGS. 13A-13F, 14A-14F, 15A-15F, each of the segments 1300, 1400, 1500 comprises a center or primary opening 1330, 1430, 1530 through which the drive shaft of the delivery system may reside. Segments 1300, 1400 further comprise bending openings 1332, 1432, 1532 in which a steering wire or element may reside. In other examples, however, the distal segment 1500, may comprise attachment structures to which the steering wires or elements attach, rather than pass through to attach to structures distal to the distal segment. The bending openings 1332, 1432, 1532 may be orientated such that they are spaced 90 degrees apart, and spaced 45 degrees apart from an adjacent alignment structure 1314, 1414, 1514.

As depicted in FIGS. 13G-13L, 14G-14L, 15G-15L, each of the segments 1300, 1400, 1500 may also comprise one or more openings 1334, 1434, 1534 and protrusions 1336, 1436, 1536. In some examples, the protrusions 1436, 1536 may reinforce the segments 1300, 1400, 1500 where the bend openings 1332, 1432, 1532 are located, and/or may facilitate the coupling or attachment of the segment 1300, 1400, 1500 to the other components of the delivery system. In the variants depicted in FIGS. 13A-13F, 14A-14F, 15A-15F, polymeric jackets or bumpers 1338, 1438, 1538 are provided around the segments 1300, 1400, 1500. These jackets or bumpers 1338, 1438, 1538 may help to disperse or redistribute the bending forces acting on the catheter body 112. This may reduce the risk of tearing and/or kinking of the catheter body 112, as well as the sheath 114. The bumper 1438 may have an overall hyperbolic paraboloid shape as depicted in FIGS. 14A-14F, or a hyperbolic paraboloid end configuration on their interface ends as depicted in FIGS. 13A-13F and 15A-15F. The jackets or bumpers 1338, 1438, 1538.

The proximal and distal segments 1300, 1500 may comprise a planar end 1340, 1540 to attach or interface with other components of the delivery system. The jackets or bumpers 1338, 1538 may comprise a non-planar end and a planar or circular end, corresponding their ends 1302, 1402, 1404, 1504. The jackets or bumpers 1338, 1438, 1538 may comprise any of a variety of materials, including silicone, polyurethane, styrenic co-block polymers, PEEK, nylon, PTFE, HDPE, and the like.

Figures 16A, 16B, 16C, 16D:
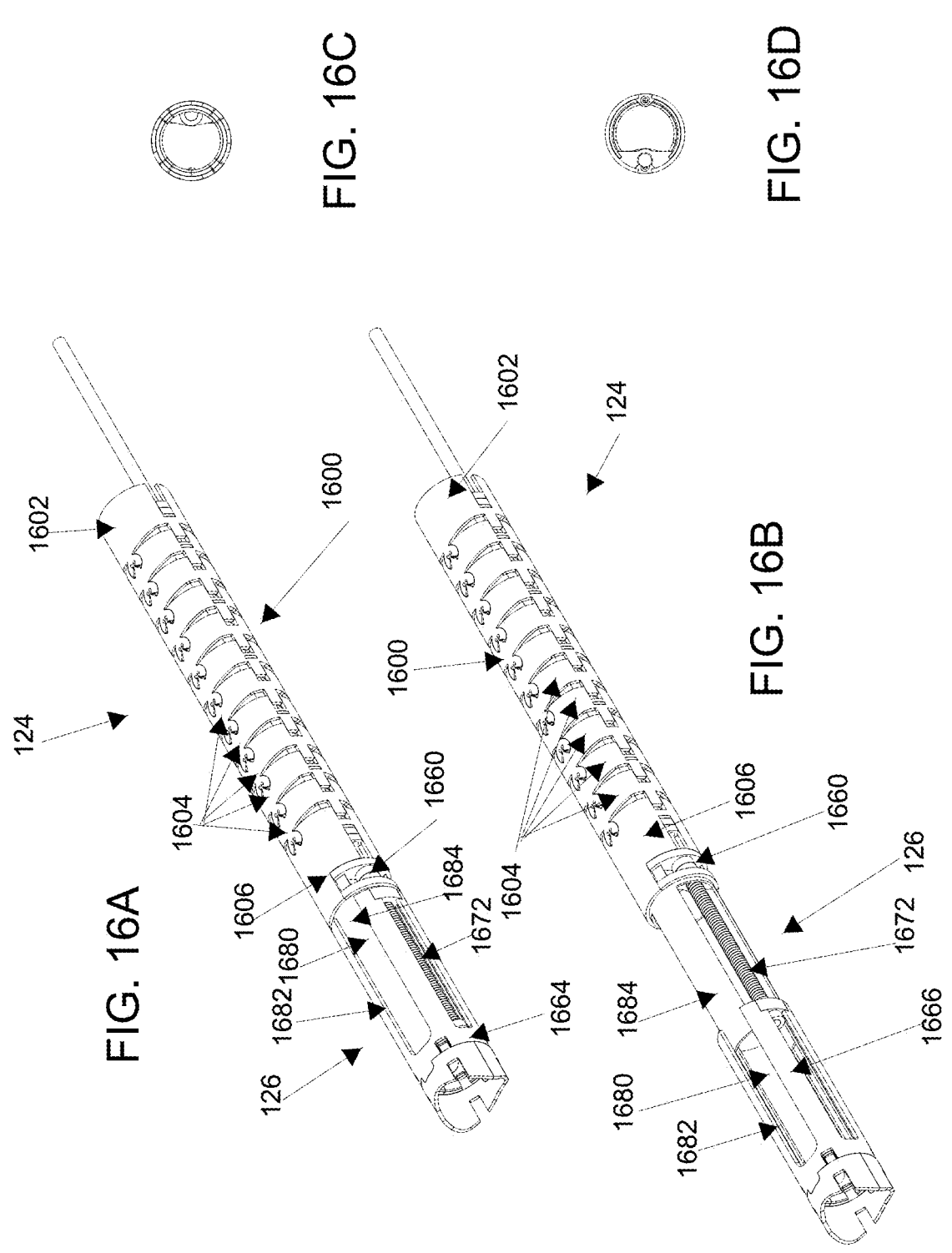
FIGS. 16A and 16B are top perspective views of the combined proximal steering and extension assembly, in a retracted and extended configuration, respectively.
FIG. 16C is a front elevational view of the extension assembly in FIGS. 16A and 16B.
FIG. 16D is a rear elevational view of the proximal steering assembly in FIGS. 16A and 16B.
Figures 16E, 16F, 16G, 16H:
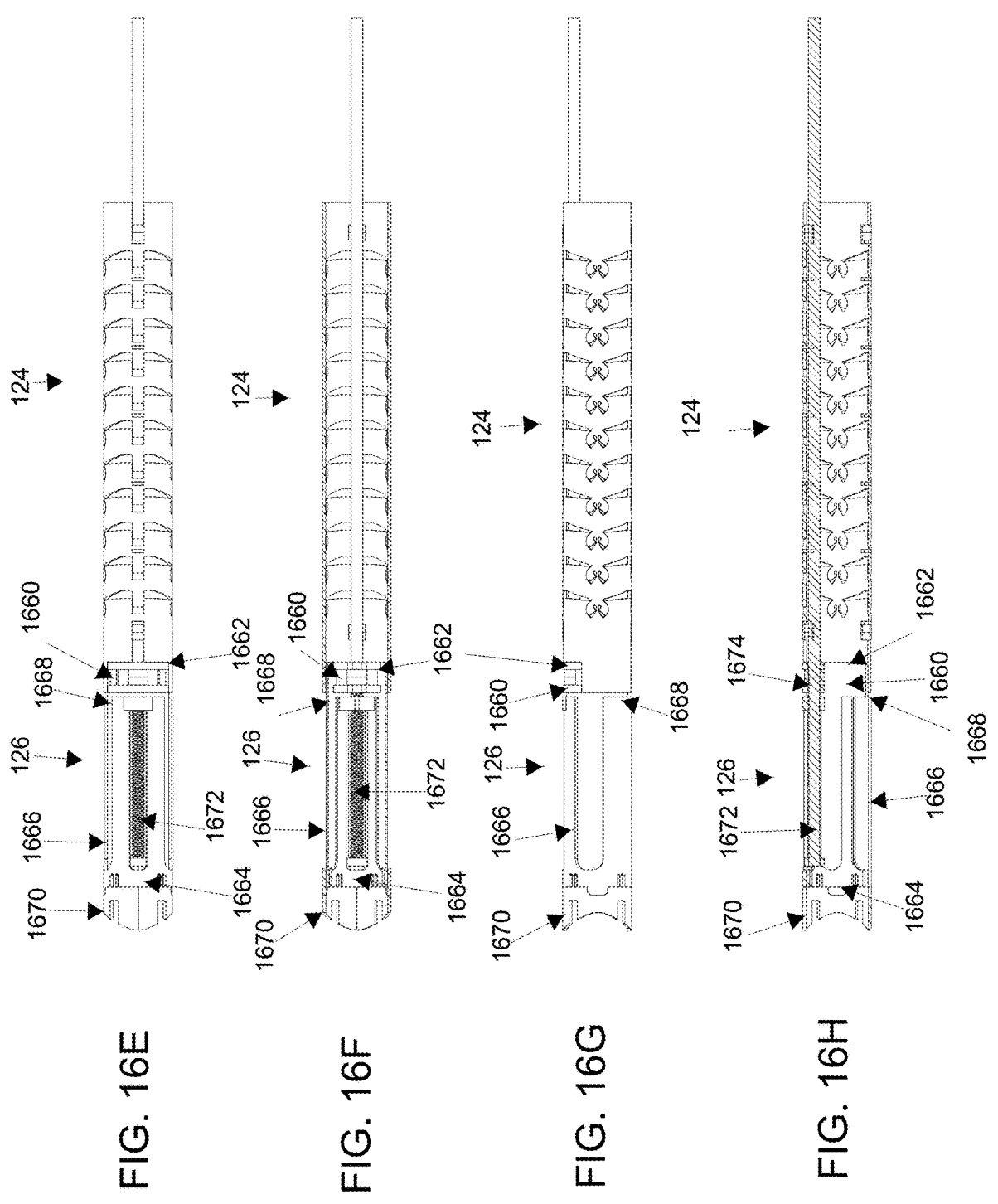
FIGS. 16E to 16H are top plan, top cross-sectional, side elevational and side cross-sectional views, respectively, of the combined proximal steering and extension assembly of FIG. 16A in a retracted configuration.

FIGS. 16A to 16L depicts an exemplary embodiment of the proximal steering and extension assemblies 124, 126 as shown in FIG. 1A. In this particular embodiment, the proximal steering assembly 124 comprises a flexible segmented tubular body 1600, but instead of discrete segments as in the distal steering assembly 128, the flexible segmented tubular body 1600 is a lasercut, unibody flexible segmented tubular body 1600 comprising segments 1602, 1604, 1606. Referring to FIG. 16M, the segments 1602, 1604, 1606 are interconnected by a pair of living hinge struts 1608 and a pair of neck regions 1610 on opposite sides of the tubular body 1600. To each side of neck region 1610 is a wedge opening 1614, which is configured to allow limited flexion between the segments 1602, 1604, 1606. The wedge opening 1614 is formed by a tapered or angular gap between the proximal ends 1616 and distal ends 1618 of the segments 1602, 1604, 1606. The maximum longitudinal separation along the opening 1614 may be in the range of 0.6 mm to 0.9 mm, 0.4 mm to 1 mm, or 0.2 mm to 1.2 mm. The angle formed by the proximal and distal ends 1616 and 1618 may be in the range of 5 degrees to 30 degrees, 8 degrees to 20 degrees, or 10 degrees to 15 degrees. The wedge openings 1614 may be in continuity with narrower arcuate slits 1620 from the apex 1622 of the wedge openings 1614 to the wide end 1624 of the strut 1608. A smaller wedge opening 1626 is provided between the wide end 1624 and the middle of strut 1608 and is also in communication with a smaller opening 1630 at the narrow end 1632 of the interconnect 1608. The smaller opening 1630 may comprise a teardrop shape, wherein the tip of the teardrop is in continuity with the tip of the smaller wedge opening 1632. Together, the larger wedge arcuate slit 1620, smaller wedge opening 1626 and teardrop opening 1630 form a partially circular configuration with a partially circular opening 1640 of one segment attached to a bifid pivot head 1642 that is able to pivot or bend within the partially circular opening 1640. The maximum bending angle between each segment 1602, 1604, 1606 may in the range of 10 degrees to 45 degrees, 15 degrees to 35 degrees, or 20 degrees to 30 degrees, and the maximum total bending angle of the segmented tube 1600 may be 75 degrees to 150 degrees, 90 degrees to 130 degrees, or 100 degrees to 120 degrees.

Figure 16N:
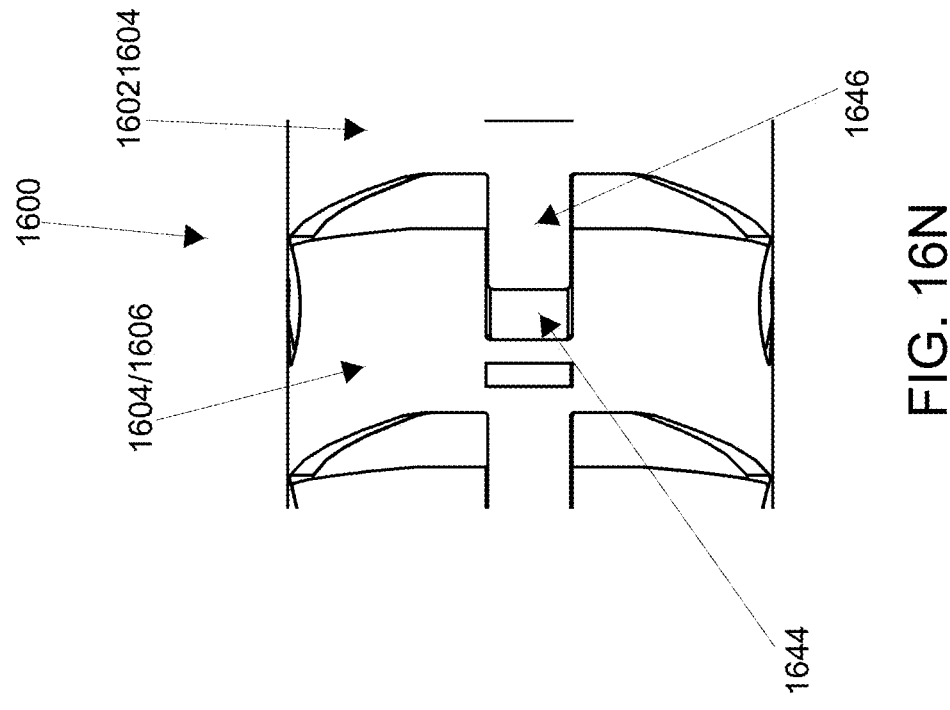
FIGS. 16M and 16N are detailed schematic views of various regions of the extension assembly.
Figure 16M:
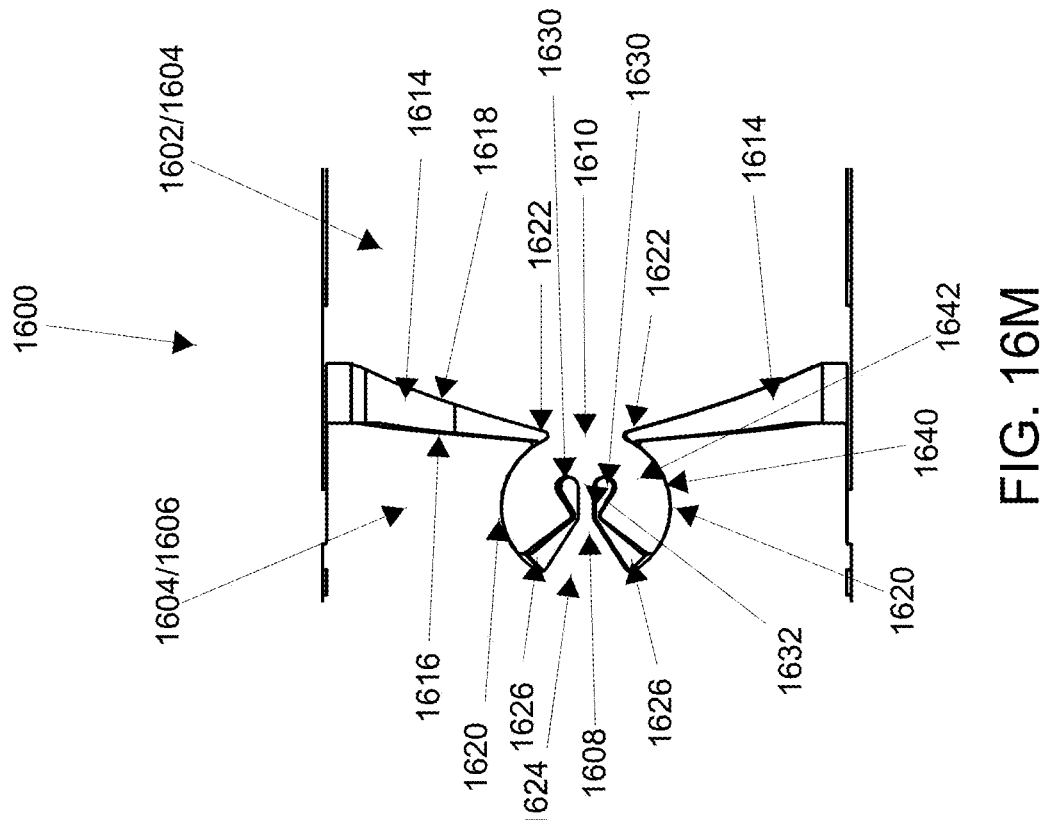

Referring to FIG. 16N, in addition the pivoting movement at each opening 1640 and complementary bifid pivot head 1642, each segment 1602, 1604, 1606 also comprises a pair of notches 1644 and/or protrusions 1646 which are slidable in the notches 1644. The notches 1644 and protrusions 1646 may resist torsional forces that are acting on the proximal steering assembly 124 and/or may also provide or support the limit on the amount of flexion between each segment 1602, 1604, 1606, based on the longitudinal length of the notches 1644 and protrusions 1646. In some variations, the lengths of the notches may be in the range of 12 mm to 25 mm, 15 mm to 22 mm, or 16 mm to 20 mm, and the lengths of the protrusions may be in the range of 1.5 mm to 2.5 mm, 1.7 mm to 2.2 mm, or 1.8 mm to 2.0 mm. The widths of the notches and protrusions may be in the range of 0.8 mm to 2 mm, 1.0 mm to 1.8 mm, or 1.1 mm to 1.4 mm. The gap length between the notches and protrusions when the proximal steering assembly is in an unbent neutral position may be in the range of 0.5 mm to 1.5 mm, 0.6 mm to 1.2 mm, or 0.7 mm to 0.9 mm. This gap length may also be the maximum gap length of the larger wedge opening 1614. The number of segments 1604 in the steering assembly in FIGS. 16A and 16B is ten, but in other examples, the number may be in the range of 1 to 20, 2 to 15, 5, to 15, or 8 to 12. The average longitudinal length of segments 1604 may be in the range of 2 mm to 10 mm, 2 mm to 6 mm, 3 mm to 5 mm, or 3.5 mm to 4.5 mm. The proximal and distal segments 1602, 1606 may be longer, e.g. in the range of 2 mm to 10 mm, 4 mm to 9 mm, 5 mm to 8 mm, 4 mm to 8 mm, 4 mm to 5 mm, 3 mm to 6 mm, or 2 mm to 8 mm.

Figures 16O, 16P:
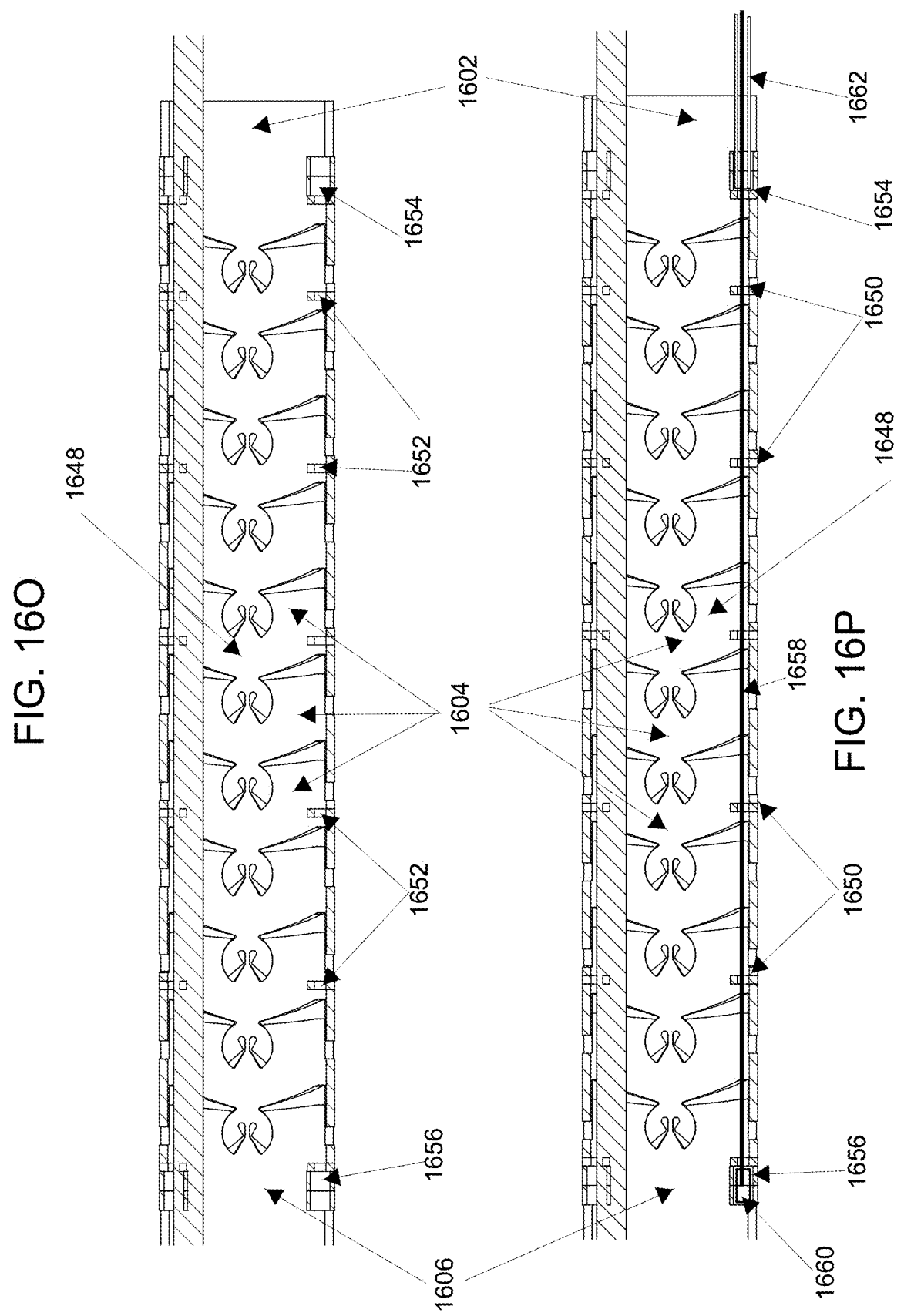
FIGS. 16O and 16P are detailed cross-sectional views of the proximal steering assembly, with and without the steering element, respectively.
Figure 17A:
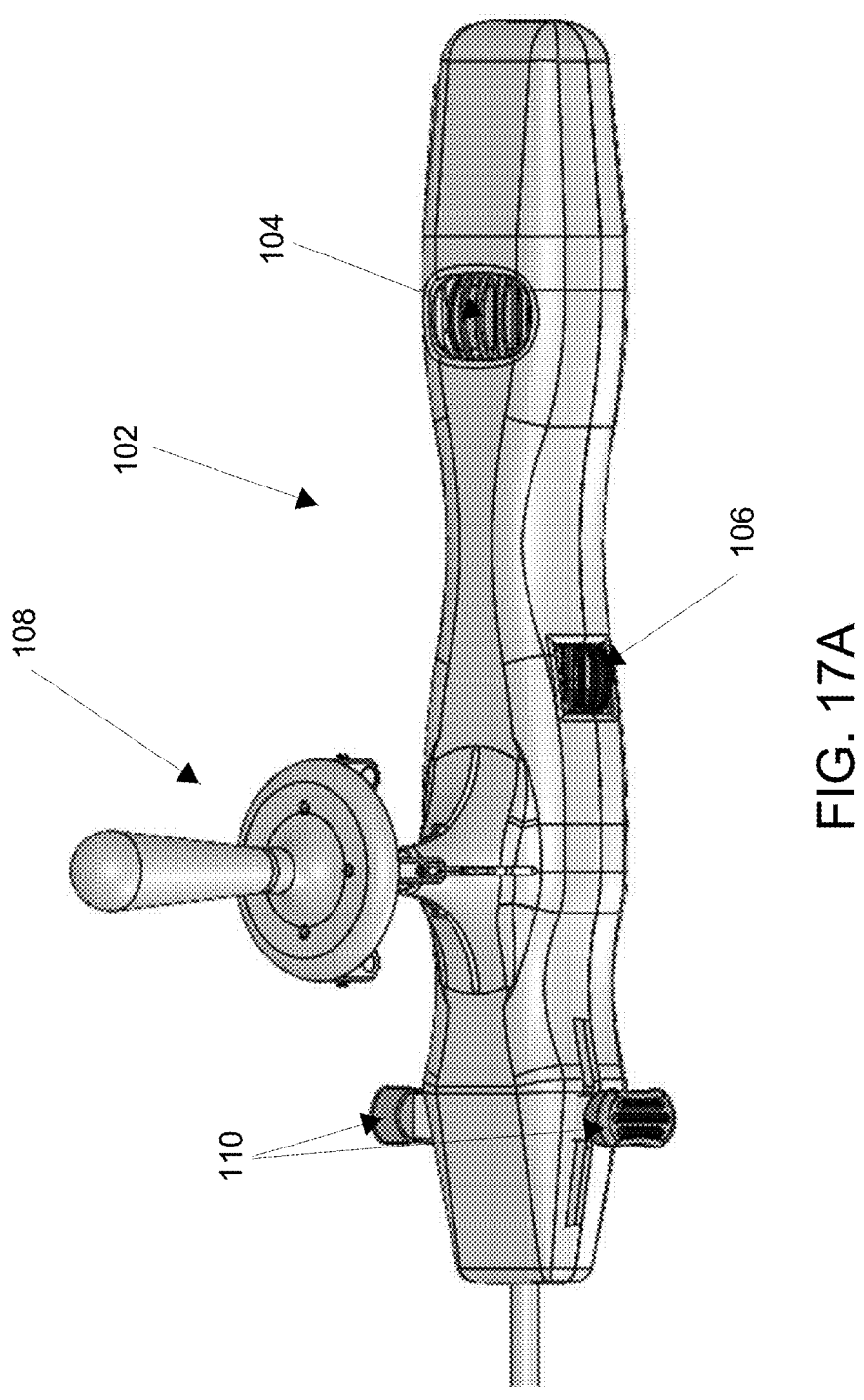
FIG. 17A is a top perspective view of the proximal handle in FIG. 1A.
Figures 17B, 17C:
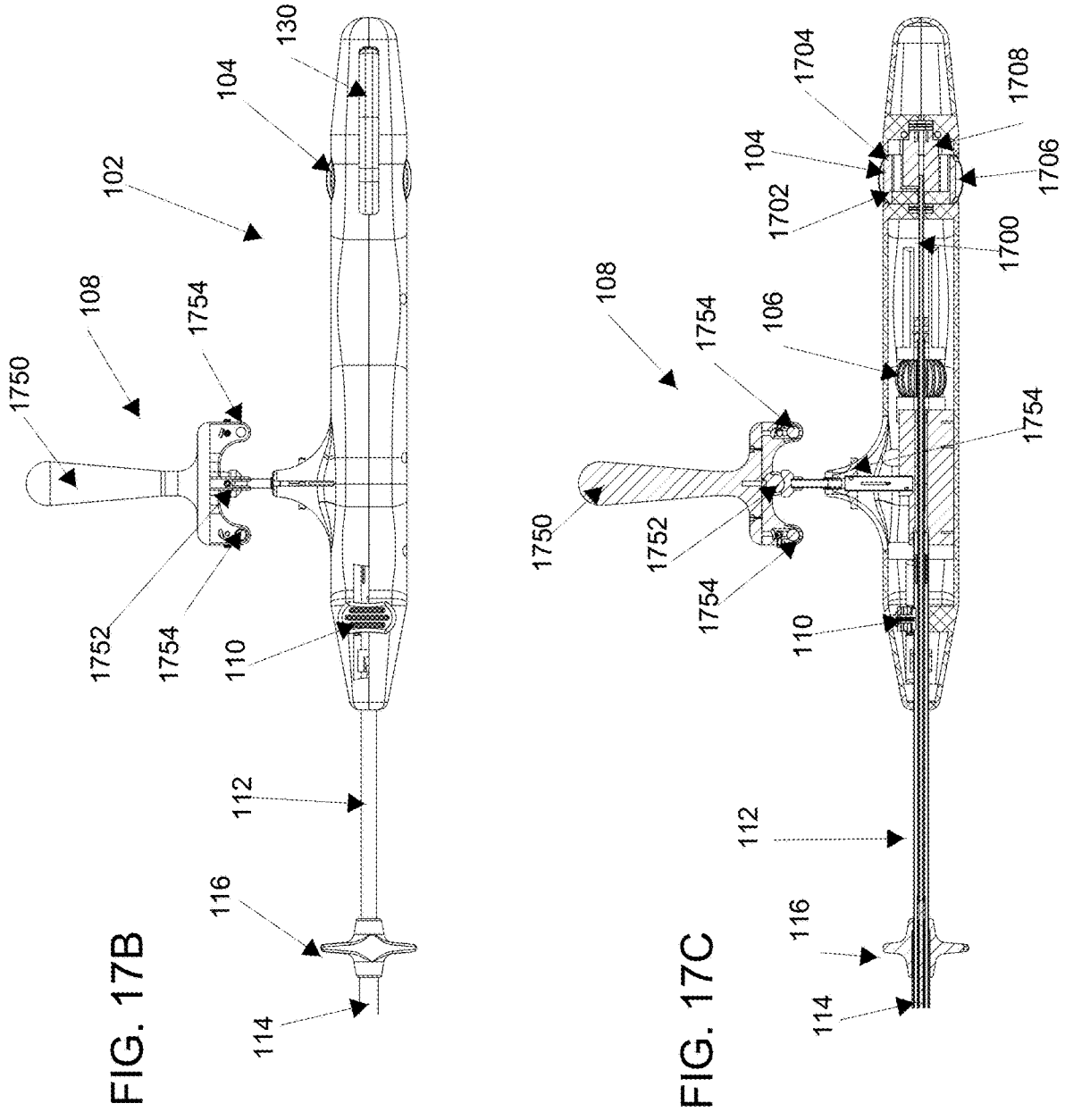
FIGS. 17B and 17C are side elevational and side cross-sectional views of the proximal handle in FIG. 17A.
Figures 17D, 17E:
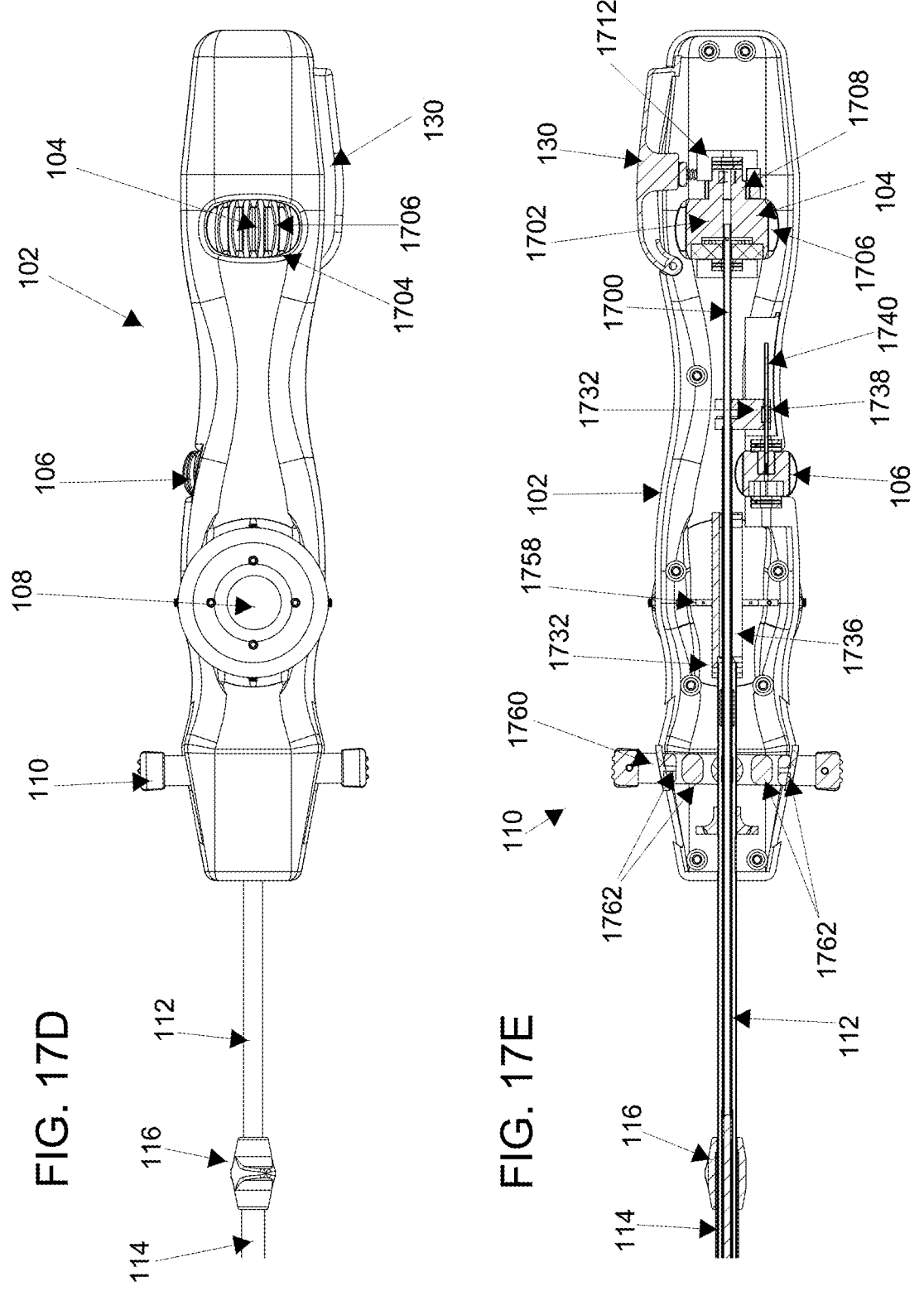
FIGS. 17D and 17E are superior plan and superior cross-sectional views of the proximal handle in FIG. 17A.
Figure 18A:
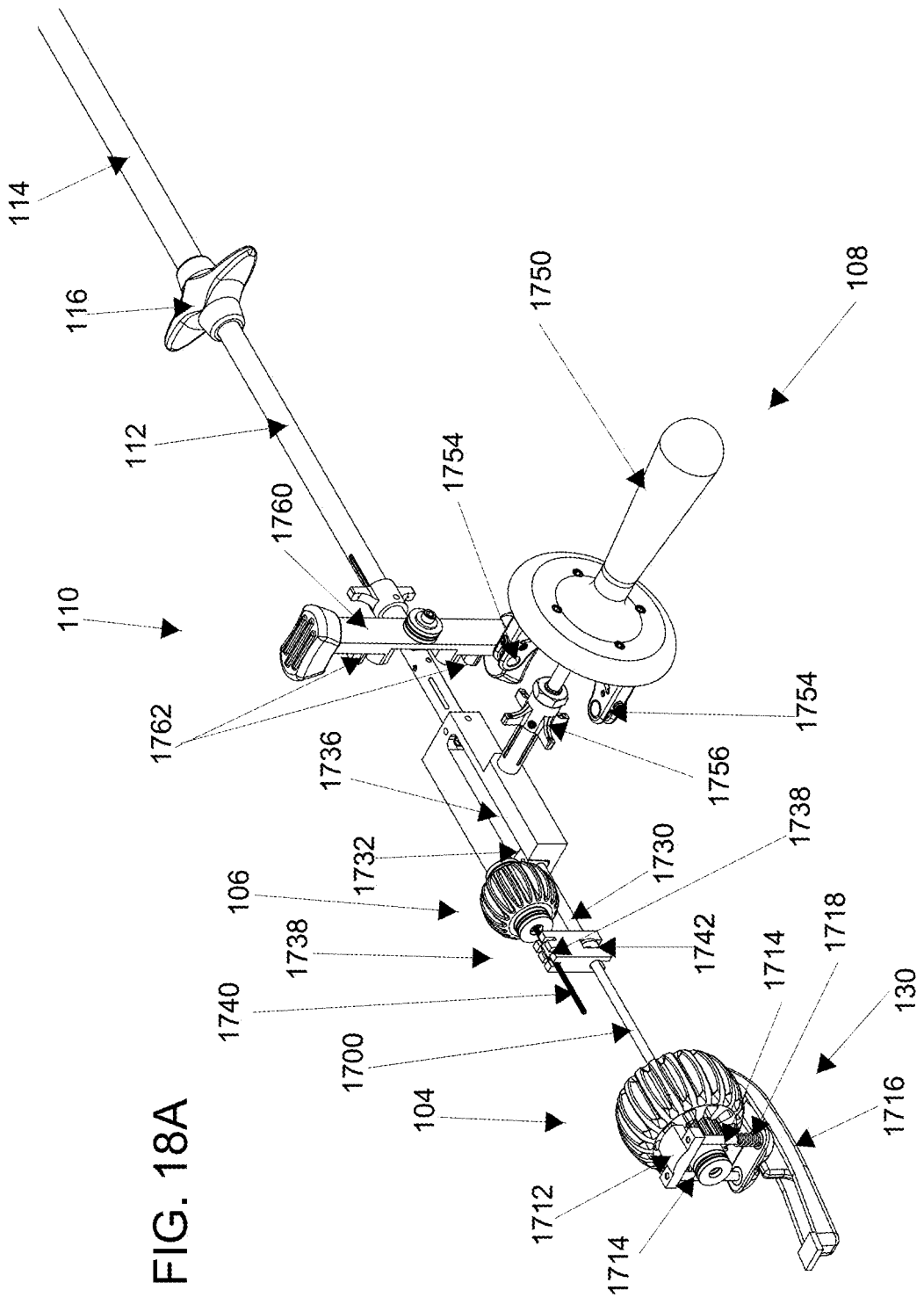
FIGS. 18A to 18C are perspective, top plan and side elevational views of the proximal handle in FIG. 17A, without the handle housing.
Figures 18B, 18C:
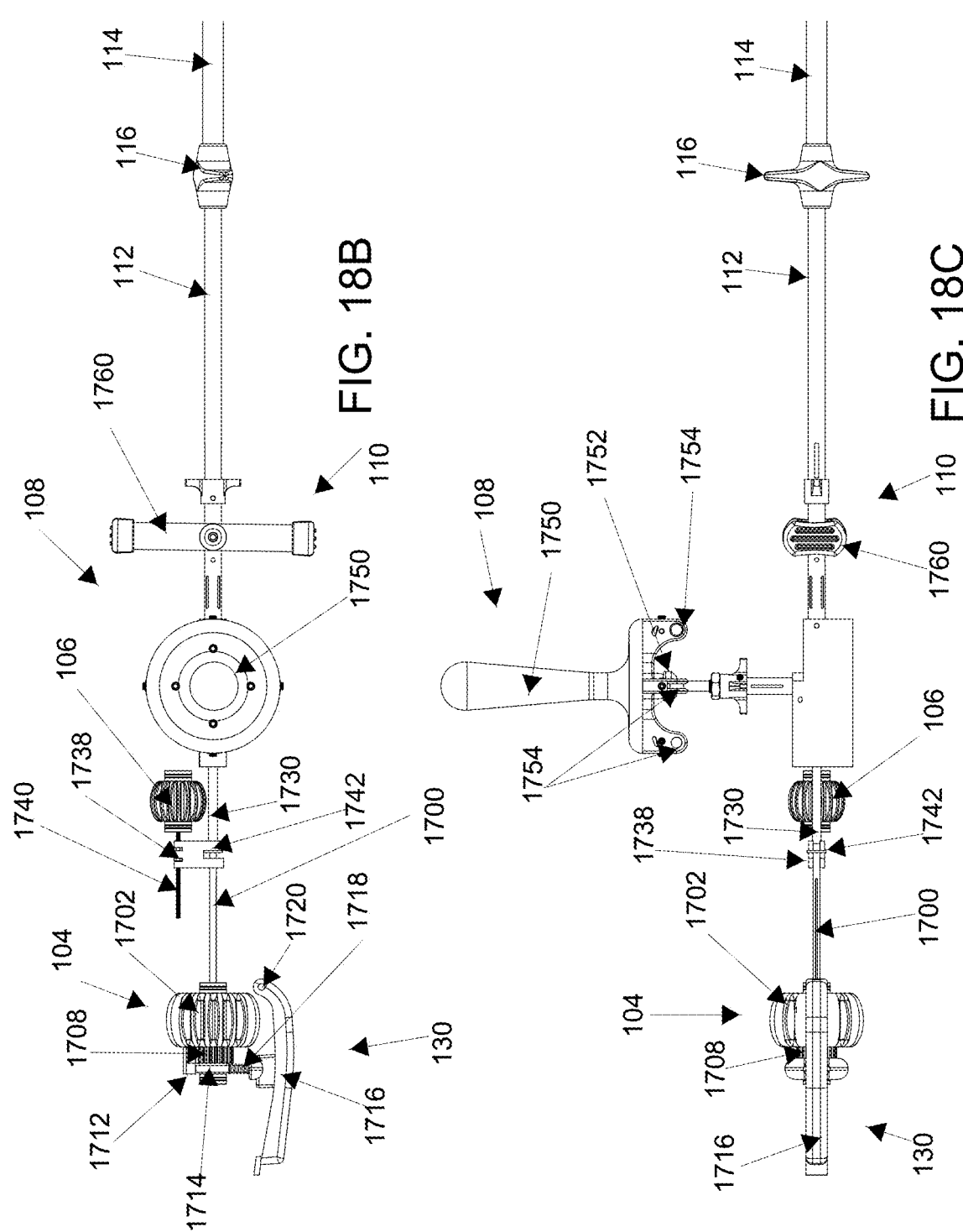

Referring to FIGS. 16O and 16P, each of the segments 1602, 1604, 1606 comprises a central or primary opening 1648, as well as steering flanges 1650 and steering openings 1652 located in the primary opening 1648 of at least some if not all of the segments 1602, 1604, 1606. The proximal and distal segments 1602, 1606 may comprise longer and/or larger steering cavities 1654, 1656. As depicted in FIG. 16P, the steering wires 1654 for the proximal steering assembly 124 slidably reside in the openings 1652 and the cavities 1654, 1656. The steering element 1658 may be attached to the distal cavity 1656 via weld, knot, crimp structure 1660 or other interference fit to the steering opening to affix. The steering element 1658 may be located in a coil sheath 1662 or other tubular structure that is attached to the steering cavity 1654 of the proximal segment 1602 of the proximal segment 1606. The steering wire may comprise a solid or multi-filament wire with a size in the range of 0.3 mm to 0.8 mm, 0.4 mm to 0.7 mm, or 0.4 mm to 0.6 mm. Proximally, the steering wires 1654 may be attached to lever 110 of the handle 102, as described in further detail below.

Referring now to the extension assembly 126 of the delivery system in FIGS. 16A to 16K, the extension assembly 126 comprises a proximal or first housing 1660 with a proximal end 1662 and a distal end 1664 and is in slidable arrangement with a distal or second housing 1666, with a proximal end 1668 and a distal end 1670. A worm gear 1672 or helically threaded shaft is rotatably coupled to a helical lumen 1674 of the proximal housing 1660. This worm gear or lead screw shaft 1672 is configured to extend and retract with rotation relative to the helical lumen 1674 and the proximal housing 1660. The distal end of the screw shaft 1672 is rotatably fixed to the proximal end 1668 of the second housing 1666 via a screw, bolt, rivet, crimp head or other fastener 1676 via an opening 1678 in the proximal end 1668. This attachment interface permits rotation of the screw shaft 1672 while also locking the extension and retraction of the screw shaft 1672 and the extension and retraction of the distal housing 1666 relative to the proximal housing 1660. To resist any torsional displacement that may occur between the proximal and distal housings 1660, 1666, a slot 1680 and grooves 1682 may be provided with one or more wall sections 1684 of the proximal and distal housings 1660, 1666. A mechanical stop structures may be provided on the worm gear or threaded shaft to provide a limit on the amount of extension. The proximal end of the worm gear or threaded shaft that controls this extension may be mechanically coupled to a rotatable knob 106 on the handle 102, which is described below.

As noted previously, control of implant expansion, steering and catheter extension may be performed using a number of controls 104, 106, 108, 110 provided on the handle 102, as depicted in FIGS. 17A to 17E. For rotation of the rotor assembly 850 900 depicted in FIGS. 8A to 9F, the rotor assembly 850, 900 may be coupled to a drive shaft 1700 in the handle 102 and attached to rotatable knob 104. The knob 104 may comprise a knob body 1702, which is exposed via one or more housing openings 1704 of the handle 102 to permit user rotation. The knob body 1702 may comprise one or more ridges 1706 to facilitate gripping of knob 104 and to resist slippage during use. The knob 104 may also comprise a secondary knob body 1708 comprises ridges or teeth that are releasably engageable by the lock assembly 130. When engaged, the locking head or structure 1712 of the lock assembly 130 engages the teeth to resist rotation of the knob 104. The locking head 1712 is attached to one or more struts 1714 to the lock lever 1716, and is biased to the engaged position by one of more springs 1718 provided on the struts 1714. To disengage the locking head 1712, the lock lever 1716 is depressed or squeezed, to thereby pivot at its housing joint 1720 and to overcome the resistance of the springs 1718 to disengage the locking head 1712.

The drive shaft 1700 is located in the tubular stator shaft 1730 located in the handle 102. To resist rotational movement of the stator shaft 1702 during manipulation of the delivery system, a stator key block 1732 is attached to or clamped to the stator shaft 1730 via a set screw or pin. The shape of the block 1704 forms a complementary interfit with the shape of the elongate block cavity 1736 resist rotational displacement while allowing longitudinal movement of the block 1704 in the cavity 1736. The longitudinal displacement permits the extension and retraction of the distal region of the delivery system as the extension assembly 126 is adjusted during the procedure. As noted previously the worm gear and threaded interface of the extension assembly 126 is configured to generate the longitudinal displacement force to extend and retract the second housing of the extension assembly, a similar threaded interface 1738 may be provided in the handle 102 to provide a second location at the proximal end of the worm gear shaft 1740 to help push or pull the stator shaft to help alleviate any resistance to the displacement of the stator shaft as it travels with the second housing of the extension assembly. The proximal threaded interface 1738 may comprise a keyed structure 1742 that permits extension and retraction of the stator shaft 1730 by exerting force on a proximal flange 1744 of the stator shaft 1730 at its proximal end during with use of the extension assembly 126.

Next, the control 108 of the 4-way distal steering assembly 128 may be provided with a joystick handle 1750. The joystick handle 1750 is configured with an articulation 1752 to pivot in at least four directions and/or a combination of the two the four directions, comprises steering element attachment structures 1754 to apply tension forces of varying amounts through the steering wire or elements (not shown) to bend the distal steering assembly 128. One or more steering wire or element guides 1756, 1758 may be provided to provide facilitate the bends in the steering wire or elements through which the tension is transferred. Similarly, the control 110 of the two-way proximal steering assembly 124 comprises a pivotable lever 1760 to which steering wires or elements are attached at attachment structures 1762 along the lever 1760. As the lever 1760 is rotated in one direction or the other direction from its neutral position, tension is generated in one of the steering wires or elements while relieving or reducing tension, if any, in the other steering wires or element. The lever 1760 may be maintained in a neutral position when not manipulated by the user either by one or more pairs of opposing springs acting on the lever 1760 or by setting a baseline balanced tension in the steering wires or elements.

Figure 19A:
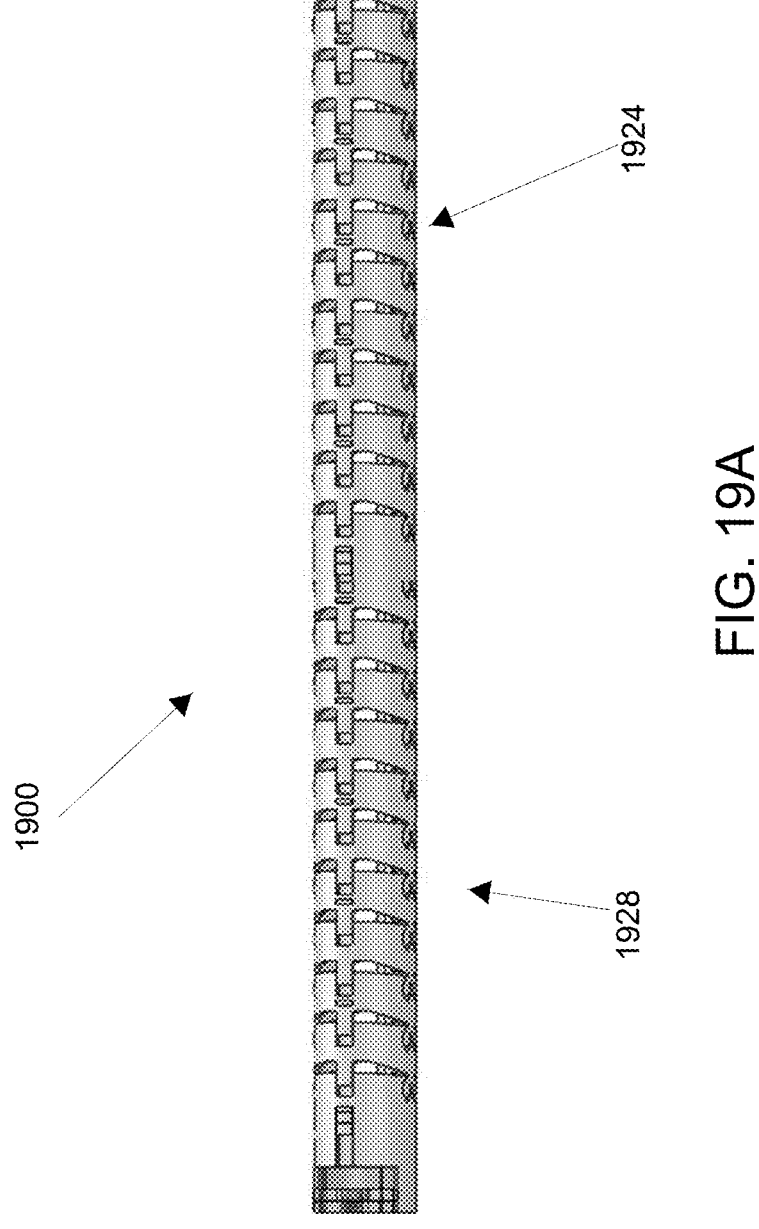
FIG. 19A depicts another embodiment of the delivery device, comprising two two-way steering assemblies.
Figures 19B, 19C:
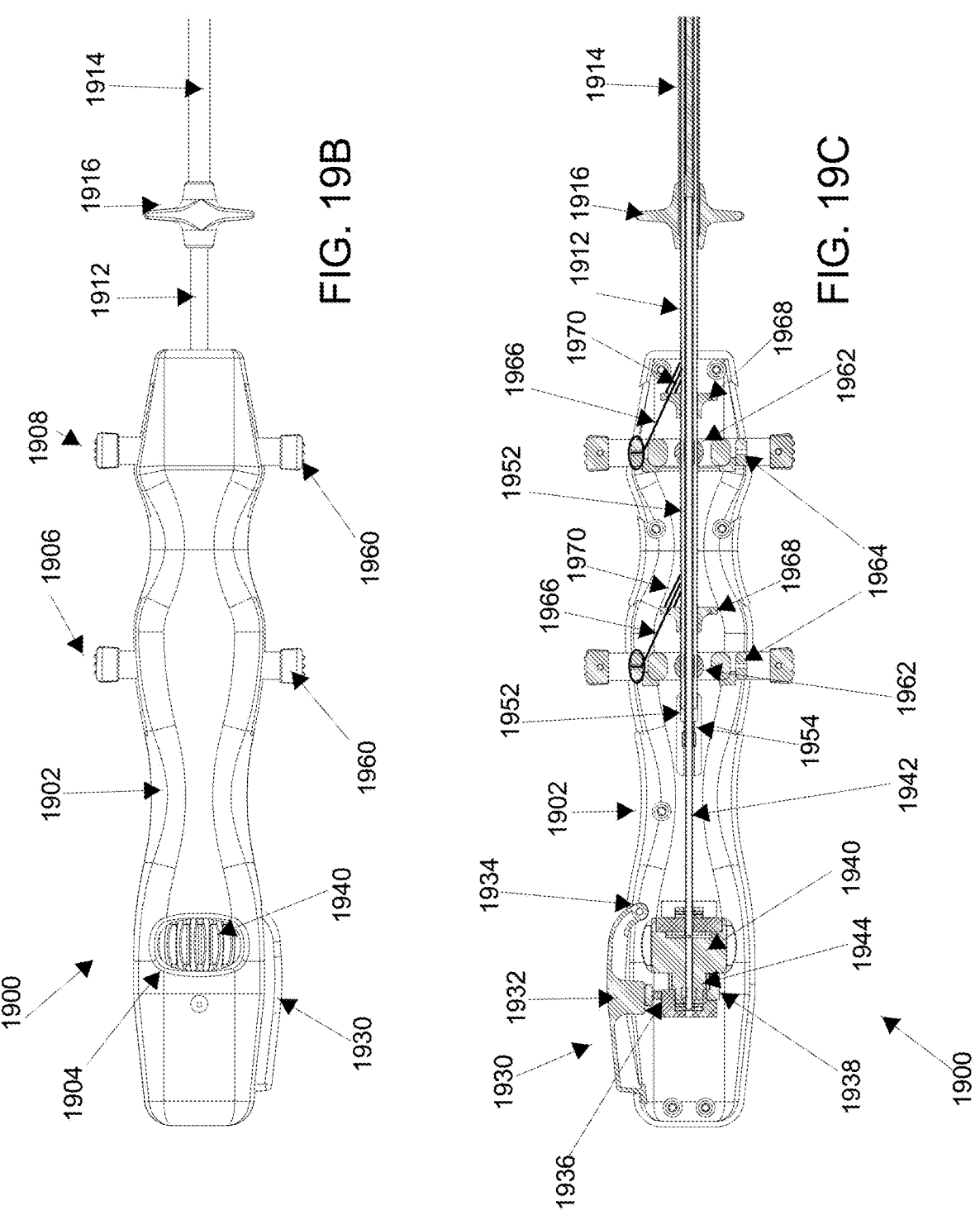
FIGS. 19B to 19E depict the handle of the delivery device of FIG. 19A.
Figures 19D, 19E:
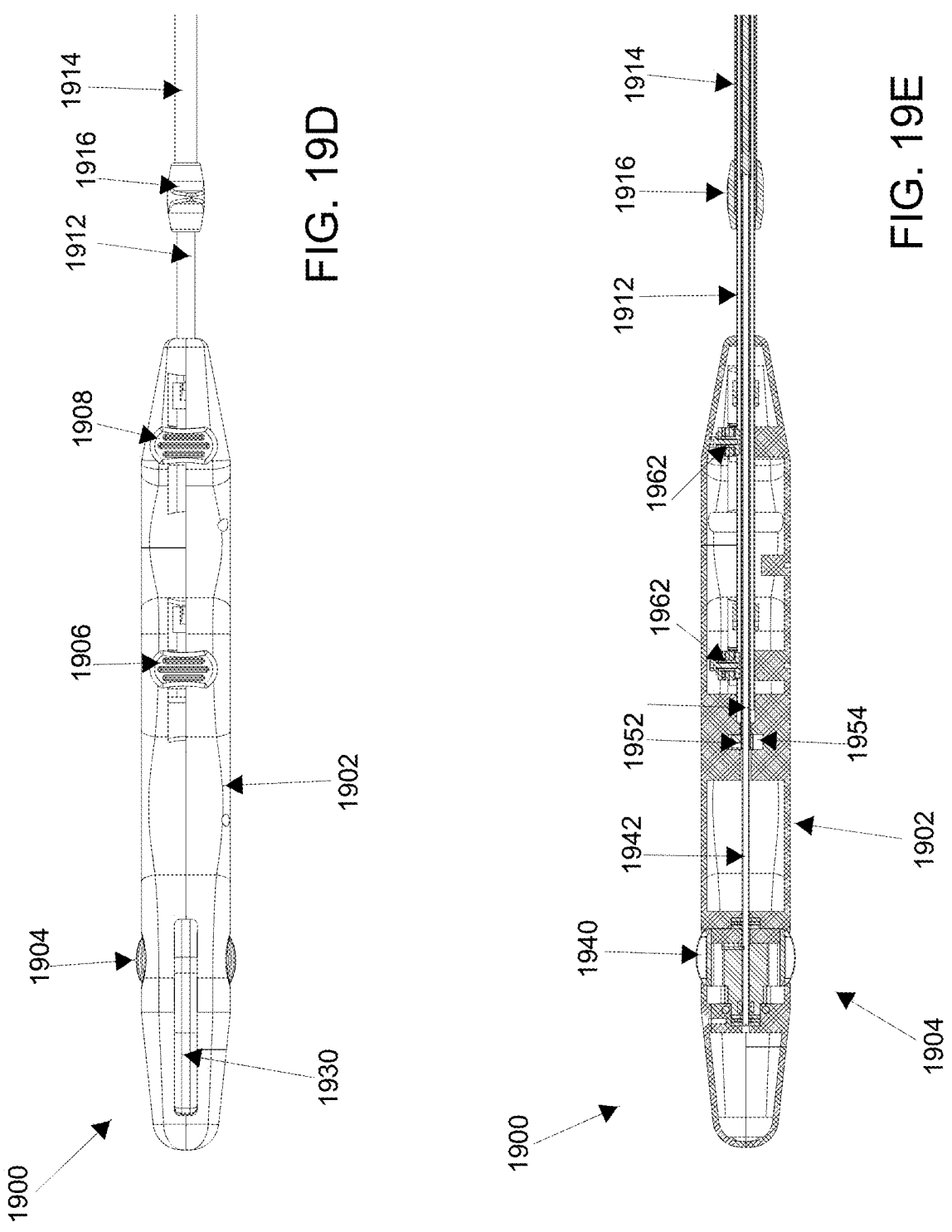

In another embodiment of a delivery device, depicted in FIG. 19A, the delivery device 1900 comprises two two-way steering assemblies 1924, 1928, without an extension assembly. In some configurations, both assemblies 1924, 1928 are configured to bend in the same bending plane, both in other configurations, the assemblies bend in different bending planes, e.g. bending planes that are orthogonal to each other. These and other components are otherwise similar to the delivery device 100 described earlier, including the rotor, stator, sheath, and adapted for this particular delivery device 1900. For example, the proximal end of the delivery device 1900 includes a handle 1902 with controls 1904, 1906, 1908 that are coupled to the catheter body 1912, along with a slidable sheath 1914 and sheath handle 1916. The control of the rotor shaft via the rotary knob 1940 of control 1904 and releasable lock 1930 are otherwise similar to the mechanism for the control 104 and releasable lock 130 of delivery device 100. The knob 1940 is fixedly attached to the rotor shaft 1942 to control the unwinding and release of the tension members in the implant delivery section of the delivery device 1900. The releasable lock 1930 comprises a lock lever 1932 that is attached to the handle 1902 via a pin joint 1934 or other articulation. The lever 1932 is maintained in a biased lock configuration via a spring 1936 that pulls the locking head 1938 into engagement with the secondary body 1944 of the knob 1940 to resist rotation. Upon depression or squeezing of the lever 1932 to overcome the spring force and to separate the locking head 1938 away from the secondary body 1944, the knob 1940 may be rotated by the user. In contrast to delivery device 100, the stator shaft 1950 of delivery device 1900 does not longitudinally displace due to the lack of an extension assembly, but may be coupled to the handle 1902 via an adhesive bond and/or a mechanical interfit or interference interface. In FIGS. 19B to 19E, for example, the stator shaft 1950 is coupled to a stator key block 1952 via a set screw or other mechanical fastener. The block 1952 is located in a block cavity 1954 with a complementary cavity shape to the outer surface of the stator key block 1952 to thereby resist rotational and longitudinal displacement.

The bending controls 1906 and 1908 may comprise a configuration similar to control 110 of delivery device 100. These controls 1906, 1908 each comprise a lever 1960 with a central pivot joint 1962 that with steering element attachment structures 1964 located on each side of the levers 1960. The steering wires or elements 1966 (depicted only on one side of the handle 1902) are coupled to the attachment structures 1964 and along steering guides 1968 and into the catheter body 1912, external to the stator shaft. Optional steering wire sheaths or compression coils 1970 may be provided to facilitate movement of the steering elements 1966. The steering elements 1966 may be routed in any of a variety of ways as shown in FIGS. 19B to 19E, but may also be routed radially inward closer to the central pivot 1962 and clamped in between the attachment structures 1964 on each side.

In one exemplary method of delivering the replacement valve, the patient is positioned on the procedure table, and the draped and sterilized in the usual fashion. Anesthesia or sedation is achieved. Percutaneous or cutdown access to the vascular or entry site is obtained, e.g. at the femoral vein, femoral artery, radial artery, subclavian artery, and an introducer guidewire is inserted. A guidewire is manipulated to reach the desired valve implantation site. Pre-shaped guidance catheters or balloon catheters may be used to facilitate the crossing of the valve implantation site Referring to FIG. 4A, the delivery system 400 with the delivery catheter 402 and valve 804 is positioned across the valve opening 406. The delivery system 400 may also be further manipulated to adjust the angle of entry through the valve opening 406 to be roughly orthogonal to the native valve opening and/or to be centered with the valve opening 406. Once the desired catheter pose is achieved, the delivery sheath 408 is withdrawn proximally, to expose the collapsed valve 404.

In FIG. 4B, the set of tension lines 428 controlling the release of the downstream end 410 of the outer wall 412 of the valve 404 are partially released, while the tension lines controlling the inner wall 416 remain tensioned. Next, in FIG. 4C, downstream end 410 of the outer wall 412 of the valve 404 is further released, allowing the downstream end, the middle region and more of the upstream end 414 of the outer wall 412 to expand further, thereby allowing the transition wall 416 of the valve 402 to at least partially expand outward. The partial expansion of the atrial end 414 and the ventricular end 410 of the valve 402 helps to further center and orient the middle region 422 of the valve 402 orthogonally prior to complete release. While the initial expansion of the atrial end 414 of the outer wall 412 in this embodiment is a secondary effect from the partial release of the ventricular end 410 of the valve 402 as longitudinal tension is released, in other examples, independent tension line control of the upstream end 414 may be provided.

In FIG. 4D, the tension lines 428 of the downstream end 410 and the tension lines 430, 432 of the upstream end 414 are further released, either simultaneously or singly in a stepwise fashion, further engaging the middle region 420 of the outer wall 412 against the valve opening 406. This further expansion of the outer wall 412 also exposes the retention barbs or projections 422 on the outer wall 412. Proper centering and orientation of the valve is reconfirmed, to make sure the valve has not been deployed in a skewed or partially disengaged pose with respect to the valve annulus. The tension lines 428, 430, 432 may be optionally re-tensioned to re-collapse the valve 404 may be performed, to facilitate re-positioning and/or re-orienting of the valve 404. Once confirmed, the tension lines of the inner wall 818 are released, as shown in FIG. 4E, which also allows the outer wall 412 to achieve its untethered expansion against the mitral valve opening 406. The tension lines 428, 430, 432 can then be separated from the valve 404 and withdrawn into the catheter and optionally out of the proximal end of the catheter 402. Alternatively, the delivery system and procedure in FIGS. 5A to 5E may be adapted for a similar delivery procedure.

In still another exemplary method of delivering the replacement valve, the patient is positioned on the procedure table, and the draped and sterilized in the usual fashion. Anesthesia or sedation is achieved, with selective ventilation of the right lung and optionally the left upper lobe of the lung to permit controlled collapse of the left lower lobe of the lung. A pursestring suture is placed at the transapical or other cardiac entry site. A trocar is inserted through a cannula or introducer with a proximal hemostasis valve, and the trocar assembly is inserted through the pursestring suture to access the cardiac chamber and the target valve.

Referring to FIG. 4A, the delivery system 400 with the delivery rigid tool 402 and valve 404 is positioned across the valve opening 406. The delivery system 400 may also be further manipulated to adjust the angle of entry through the valve opening 406 to be roughly orthogonal to the native valve opening and/or to be centered with the valve opening 406. Once the desired tool pose is achieved, the delivery sheath 408, if any, is withdrawn proximally, to expose the collapsed valve 404.

In FIG. 4B, the tension lines 438 controlling the release of the downstream end 410 of the outer wall 412 of the valve 804 are partially released, while the tension lines 430, 432 controlling the inner wall 416 remains tensioned. Next, in FIG. 4C, downstream end 410 of the outer wall 412 of the valve 404 is further released, allowing the downstream end, the middle region and more of the upstream end 414 of the outer wall 412 to expand further, thereby allowing the transition wall 416 of the valve 402 to at least partially expand outward. The partial expansion of the atrial end 414 and the ventricular end 410 of the valve 402 helps to further center and orient the middle region 422 of the valve 402 orthogonally prior to complete release. While the initial expansion of the atrial end 414 of the outer wall 412 in this embodiment is a secondary effect from the partial release of the ventricular end 410 of the valve 402 as longitudinal tension is released, in other examples, independent control of each tension line may be provided.

In FIG. 4D, the tension lines of the downstream end 410 and upstream end 414 are further released, either simultaneously or singly in a stepwise fashion, further engaging the middle region 420 of the outer wall 412 against the valve opening 406. This further expansion of the outer wall 412 also exposes the retention barbs or projections 422 on the outer wall 412. The tension lines may be optionally re-tensioned to re-collapse the valve 404 may be performed, to facilitate re-positioning and/or re-orienting of the valve 404. Proper centering and orientation of the valve is reconfirmed, to make sure the valve has not been deployed in a skewed or partially disengaged pose with respect to the valve annulus. Once confirmed, the tension lines of the inner wall 418 are released, as shown in FIG. 4E, which also allows the outer wall 412 to achieve its untethered expansion against the mitral valve opening 406. The tension lines 428, 430, 432 can then be released as shown and described for FIGS. 10G and 10H, or cut with the cut ends withdrawn into the catheter and optionally out of the proximal end of the delivery tool 402. Alternatively, the delivery system and procedure in FIGS. 5A to 5E may be adapted for a similar delivery procedure.

In some embodiments, the delivery system may be configured with an attachment interface proximal to the implant delivery section. This allows the attachment of the implant delivery section to the rest of the delivery system at the point of manufacture or at the point of use, during the assembly process or final step of the assembly procedure or preparation procedure. The attachment interface may facilitate the attachment of different handles, steering assemblies and/or different size implants during the manufacturing process or during clinical use. The attachment interface may also facilitate the separate packaging and sterilization of different components delivery system, which may have different packaging or sterilization requirements, thereby simplifying the manufacturing process, e.g. different sterilization and packaging of a pre-attached valve and/or pre-routed tension members to the stator/rotor assembly, vs. the handle and catheter body of the delivery system.

The location of the attachment interface of the delivery system may vary, depending on the features provided for the delivery system. For example, the attachment interface may be located within the distal catheter section, between a distal steering mechanism and the implant delivery section, or may be located at the proximal end of the distal catheter section, between the catheter body and the proximal end of the distal catheter section or implant delivery section, depending on whether any steering or extension assembly is provided.

Figures 20A, 20B, 20C, 20D:
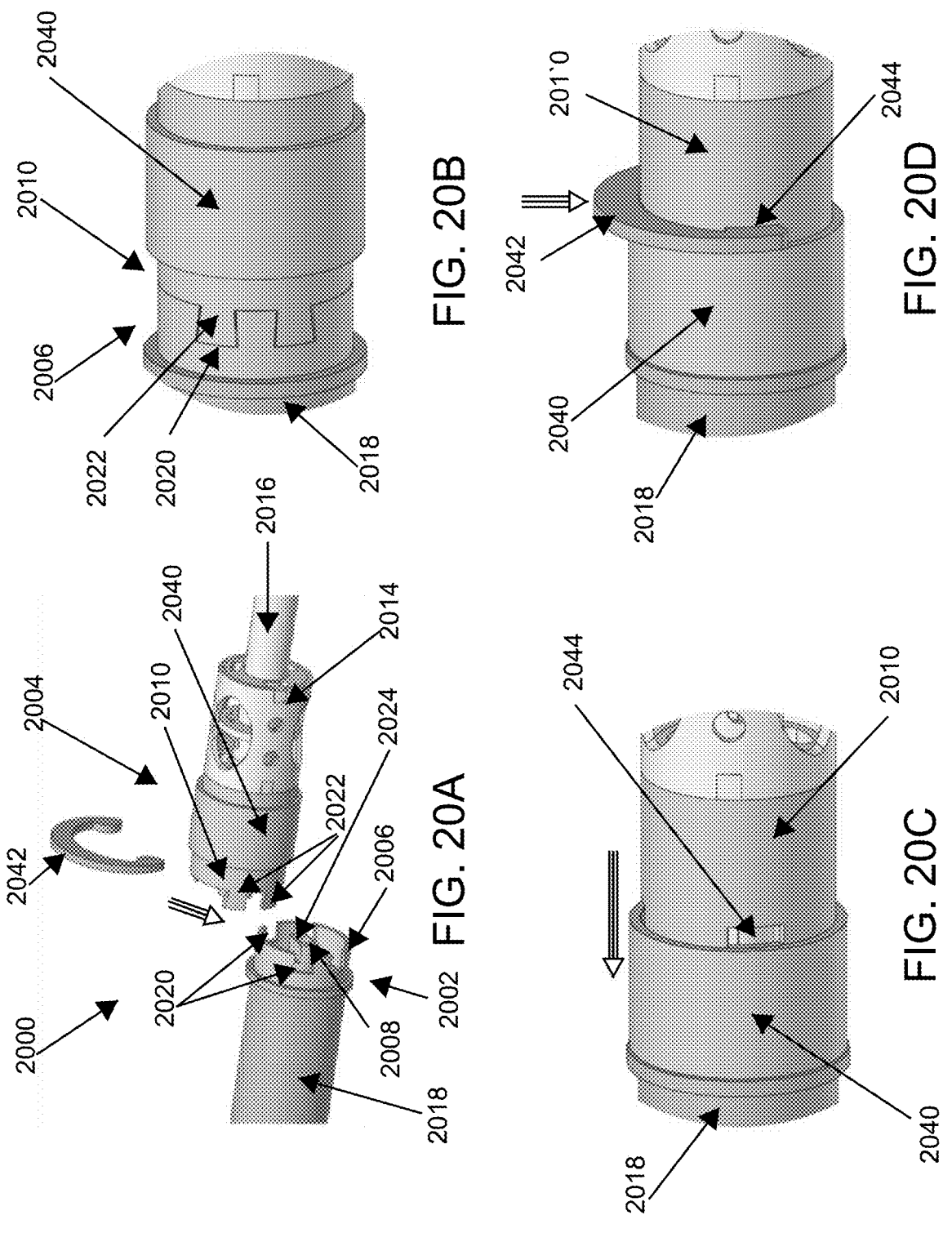
FIG. 20A is a schematic component view of another embodiment of the delivery device, comprising an attachment interface in the distal catheter section to provide attachment of the implant delivery section.
FIG. 20B is a perspective view of the engagement of the implant delivery section.
FIG. 20C is a perspective view of the locking collar in the locked position.
FIG. 20D is a perspective view of the securement device in the secured position.

FIGS. 20A to 20D and 21A to 21B, for example, depicts an exemplary embodiment of the attachment interface 2000 of a delivery system that, for simplification, does not depict a steering or extension mechanism, that may be included. The attachment interface 2000 comprises a proximal attachment interface 2002 and distal attachment interface 2004. The proximal attachment interface 2002 comprises a proximal outer tube interface 2006, a drive shaft interface 2008, and the distal attachment interface 2004 comprises a stator tube interface 2010 and a rotor shaft interface 2012 (depicted in FIG. 21A), coupled to the stator housing 2014 and the rotor shaft 2016, respectively. The proximal outer tube 2006 and the stator tube interface 2010, and the drive shaft interface 2008 and the rotor shaft interface 2012, are configured to be engaged to form a mechanical interfit that resists longitudinal detachment and/or rotational separation when engaged. As illustrated in FIGS. 20A and 20B, the proximal outer tube 2006 may be attached or bonded to the end of the catheter body 2018, or steering/extension assemblies if provided. The proximal outer tube 2006 comprises a plurality of cut-outs or recesses 2020 located along the rim of the opening of the proximal outer tube 2006. These recesses 2020 form a complementary mechanical interfit with a plurality of projections 2022 of the stator tube interface 2010. Similarly, the drive shaft interface 2008 may comprise a plurality of recesses 2024, which in turn is configured to form a mechanical interfit with a plurality of projections 2026 of the rotor shaft interface 2012. Once the proximal and distal attachment interfaces 2002, 2004 are engaged, torque from the handle of the delivery system may be transmitted through the drive shaft interface 2008 and rotor shaft interface 2012 to the rotor shaft 2016, to adjust the tension members.

Once engaged, the attachment interface 2000 may be maintained in the engaged configuration with one or more locking structures or a locking assembly. For example, in FIGS. 20A to 21B, the locking interface may comprise a locking collar 2040 and a securing component 2042, where the locking collar 2040 resists transverse movement of the attachment interface 2000 when engaged and wherein the securing component 2042, which may be a pin or a resilient C-ring, resists the longitudinal displacement or disengagement of the locking collar 2040, when the securing component is engaged to one or more securing recesses 2044 located on the stator tube interface 2010.

Figures 21A, 21B:
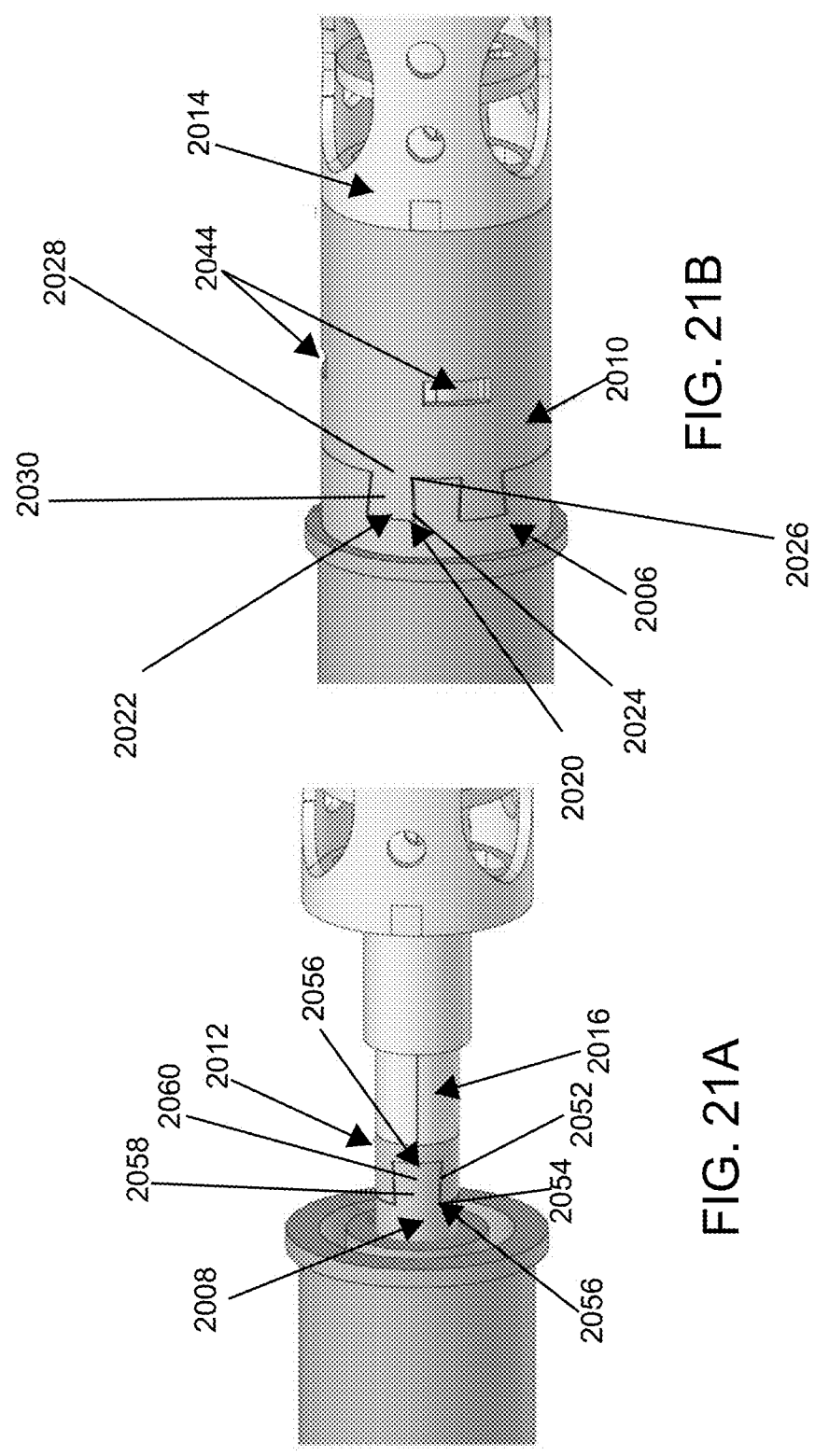
FIG. 21A depicts the engagement of the attachment interface of the drive shaft, without the stator interface.
FIG. 21B depicts the engagement of the attachment interface of the stator interface.

In this particular example, as depicted best in FIG. 21B, the recesses 2020 each configured with a neck region 2024 that has a narrower width than a head region 2026, and the projections 2022 are each similarly configured with a neck region 2028 that is narrower in width than its head region 2030. The neck regions 2024 of the recesses 2020 form a complementary interfit with the head regions 2030 of the projections 2022, and the head regions 2026 of the recesses 2020 for a complementary interfit with the neck regions 2028 of the projections 2022. This configuration allows the engagement of the recesses 2018 and the projections 2024 by permitting transversely translating the recesses 2018 and 2024 into engagement, but resisting longitudinal translation once engaged, as the wider head regions 2030 of the projections 2022 resist longitudinal displacement through the narrower neck regions 2024 of the recesses 2020. When engaged, the locking collar 2040 may then be longitudinally displaced proximally from an unlock position where the attachment interface 2000 is uncovered or exposed, to a locked position where the locking collar 2040 covers the attachment interface 2000 so that transverse translation to separate the recesses 2020 and projections 2022 is resisted. In the particular example in FIGS. 20A to 21B, the head/neck configuration is a slightly angled keystone or trapezoidal shape which correspond to the larger head and narrower neck regions, with an angle in the range of 1 to 10 degrees or 2 to 5 degrees, but in other variations, a greater angle up to 20 degrees, 30 degrees or 45 degrees may be provided.

Similarly, referring to FIG. 21A, the plurality of recesses 2050 of the drive shaft interface 2008 may comprise head and neck regions 2052, 2054, respectively, that form a complementary mechanical interfit with the neck and head regions 2058, 2060, respectively of the projections 2056 of the rotor shaft interface 2012. The head and neck regions 2052, 2054, 2058, 2066 may also have angled sides so that the recesses 2032 and the projections 2038 may be engaged by transverse translation, but resist longitudinal separation once engaged.

Referring still to FIGS. 20A to 21B, to facilitate the transverse engagement of the attachment interface components, certain configurational features may be provided. Referring to the example in FIG. 22, the attachment interface 2200 comprise a proximal attachment interface 2202 on a distal end of a proximal structure of the delivery system, and a distal attachment interface 2204 on a proximal end of the corresponding distal structure of the delivery system. The proximal attachment interface 2202 comprise an outer tube interface 2206, and a drive shaft interface 2208 with a guidewire or central lumen 2210. The outer tube interface 2206 comprises four recesses 2212a-b, 2214a-b, and the drive shaft interface 2208 comprises two drive shaft engagement surfaces or recesses 2216a-b. The complementary distal attachment interface 2204 comprises a stator tube or housing 2218 with four projections 2220a-b, 2222a-b, and a rotor shaft interface 2224 with two projections 2226a-b or yoke arms. To facilitate the transverse engagement, the sides of recesses 2212a and 2212b are aligned on each side with each other along with the sides of corresponding projections 2220a and 2220b. In addition, the sides of the recesses 2212a, 2212b and projections 2220a and 2220b that are closer to the center of the delivery system are also aligned with the recess 2216a of the drive shaft 2208 and the engagement surface of the corresponding arm or projection 2226a of the rotor shaft interface 2224. The drive shaft recess 2216a and the arm or projection 2226a are also aligned with each other. Likewise, the sides of recesses 2214a and 2214b are aligned on each side with each other along with the sides of corresponding projections 2222a and 2222b, and the sides of the recesses 2214a, 2214b and projections 2222a and 2222b that are closer to the center of the delivery system are also aligned with the recess 2216*b* of the drive shaft 2208 and the corresponding arm or projection 2226*b* of the rotor shaft 2224, and where the drive shaft recess 2216*b* and the arm or projection 2226*b* are also aligned with each other. Together, the described alignments of these structures allow the transverse engagement of the proximal and distal attachment interfaces 2202, 2204 while the wider/narrower regions of the recesses and projections described earlier provide resistance to longitudinal separation once engaged.

The total gap or difference between the inner diameter of the locking collar and the outer diameter of the outer tubing interface may be in the range of 10 μm to 1000 μm, or 100 μm to 800 μm, or 200 μm to 500 μm. The gap may be selected to reduce the movement friction of the locking collar movement while limiting any play between the proximal and distal interfaces of the attachment interface that may result in partial disengagement at the attachment interface. The gap may be smaller than the radial thickness of the proximal and/or distal interfaces of the outer tubing and stator structures.

Although the embodiment depicted in FIGS. 20A to 22 is configured at both the outer tubing/stator housing and the drive shaft/rotor shaft to resist longitudinal separation, in other variations, only the outer tubing/stator housing interface may be configured to resist longitudinal separation, while the drive shaft/rotor shaft interface may not be configured to resist longitudinal separation, or where only the drive shaft/rotor shaft interface may be configured to resist longitudinal separation, but the outer tubing/stator housing interface may not be configured to resist longitudinal separation. These variations may provide greater tolerances and ease of use during transverse engagement of the attachment interface. In still other variations, the locking collar may be configured to resist longitudinal separation via barbs and recesses, such that neither the outer tubing/stator housing interface nor the drive shaft/rotor shaft interface are configured to resist longitudinal separation. In still other variations, one or more of the complementary features on the proximal attachment interface and the distal attachment interface may be reversed in their locations.

Referring back to FIG. 22, the alignments of the various structures allow the transverse engagement to be performed bi-directionally, e.g. starting with recesses 2212*a*, 2214*a* with projections 2220*b*, 2222*b*, or starting with recesses 2212*b*, 2214*b* and projections 2220*a*, 2222*a*. In other variations, as shown in FIGS. 23 and 24, the alignments and sizes of the various structures may be configured to only allow transverse engagement to performed in one direction only. A unidirectional interface may make it easier for the user or assembler to seat the projections into the recesses by providing or one or more stop surfaces to facilitate alignment during the engagement at the attachment interface, which may make alignment of the proximal and distal attachment interfaces easier and reduce the potential risk of jamming during engagement.

Referring to FIG. 23, the attachment interface 2300 comprises a proximal attachment interface 2302 on a distal end of a proximal structure of the delivery system, and a distal attachment interface 2304 on a proximal end of the corresponding distal structure of the delivery system. The proximal attachment interface 2302 comprise an outer tube interface 2306, and a drive shaft interface 2308 with a guidewire or central lumen 2310. The outer tube interface 2306 comprises four recesses 2312*a-b*, 2314*a-b* and the drive shaft interface 2308 comprises two drive shaft engagement surfaces or recesses 2316*a-b*. The complementary distal attachment interface 2304 comprises a stator tube or housing interface 2318 with four projections 2320*a-b*, 2322*a-b*, and a rotor shaft interface 2324 with two projections 2326*a-b* or yoke arms. In this embodiment, recess 2312*a* is smaller than recess 2312*b* and projection 2320*b*, with respect to their widths along the transverse translation axis, and projection 2320*a* is smaller than recess 2312*b* and projection 2320*b*, but recess 2312*a* is aligned with projection 2320*a*, and recess 2312*b* is aligned with projection 2322*b*. Recess 2316*a* of the drive shaft interface 2308 and the corresponding arm or projection 2326*a* of the rotor shaft interface 2324 remain aligned, with arm or projection 2326*a* configured by size and location to clear recess 2312*b*. Likewise, recess 2314*a* is smaller than recess 2314*b* and projection 2322*b* with respect to their widths along the transverse translation axis, and projection 2322*a* is smaller than recess 2314*b* and projection 2322*b*, but recess 2314*a* is aligned with projection 2322*a*, and recess 2314*b* is aligned with projection 2322*b*. Recess 2316*b* of the drive shaft 2308 and the corresponding arm or projection 2326*b* of the rotor shaft 2324 remain aligned with each other, with arm or projection 2326*b* configured to clear recess 2314*b*.

Figure 22:
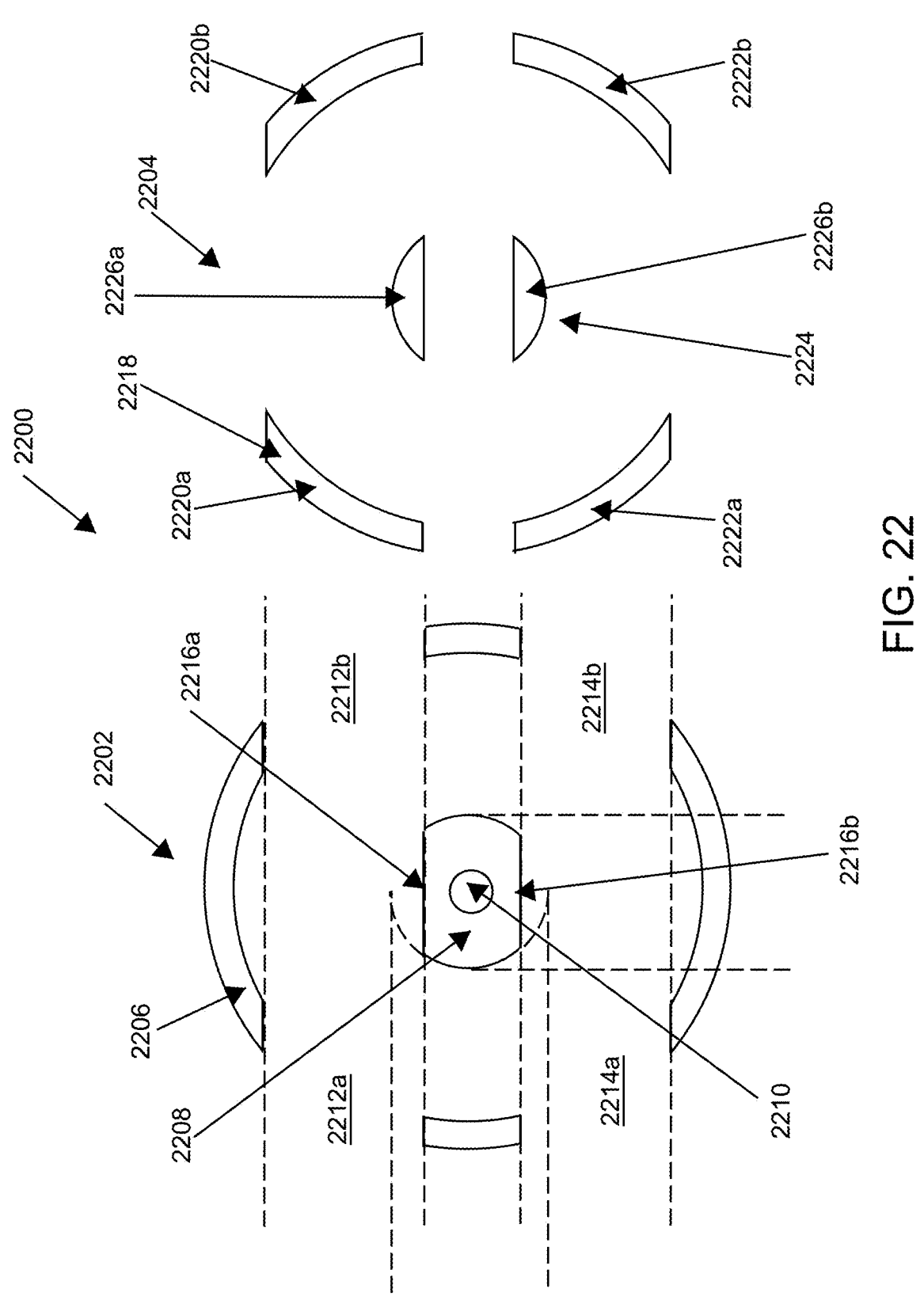
FIGS. 22 to 25 depict various exemplary configurations of the attachment interface to facilitate engagement of delivery system components.
Figure 23:
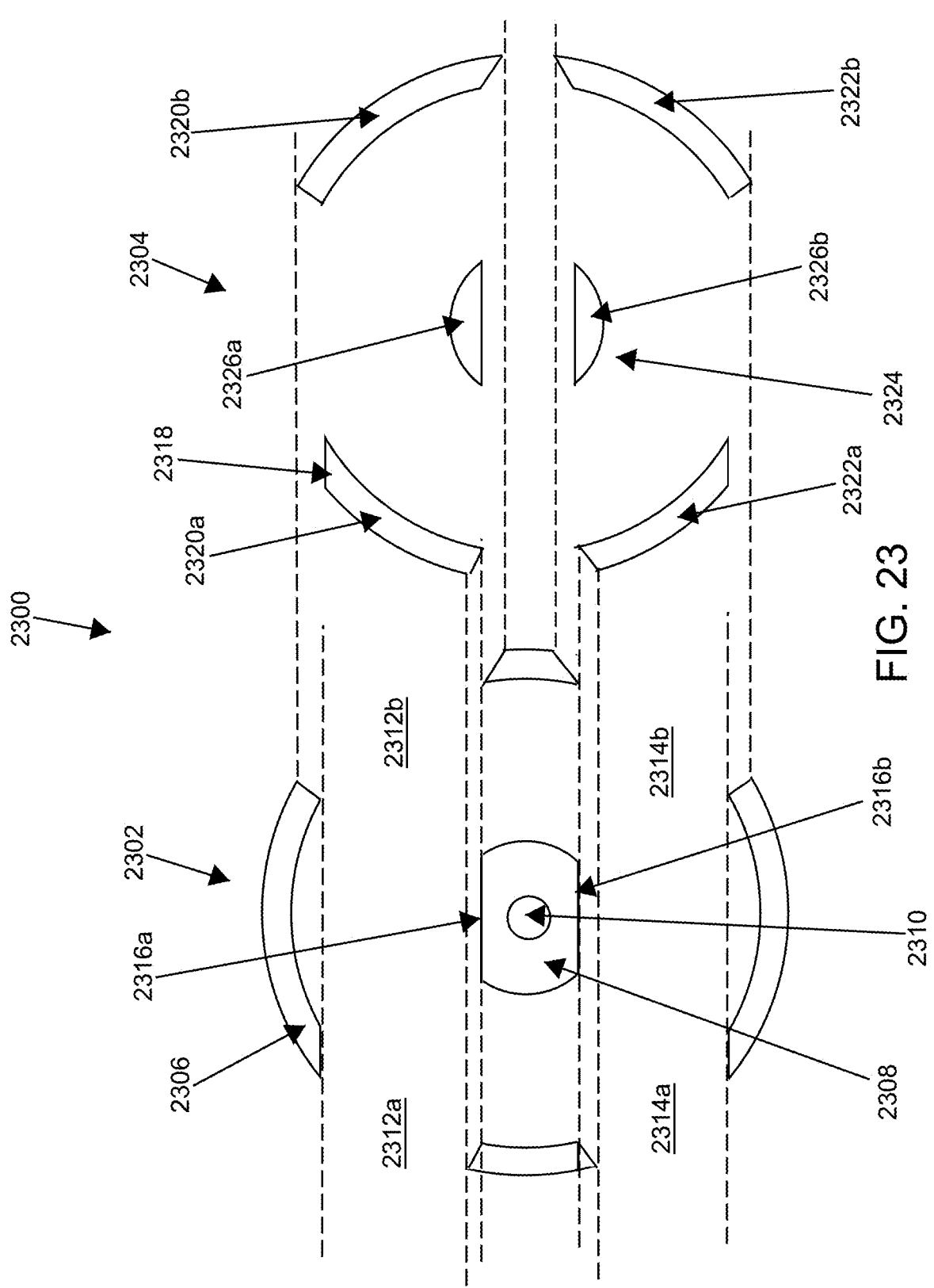
Figure 24:
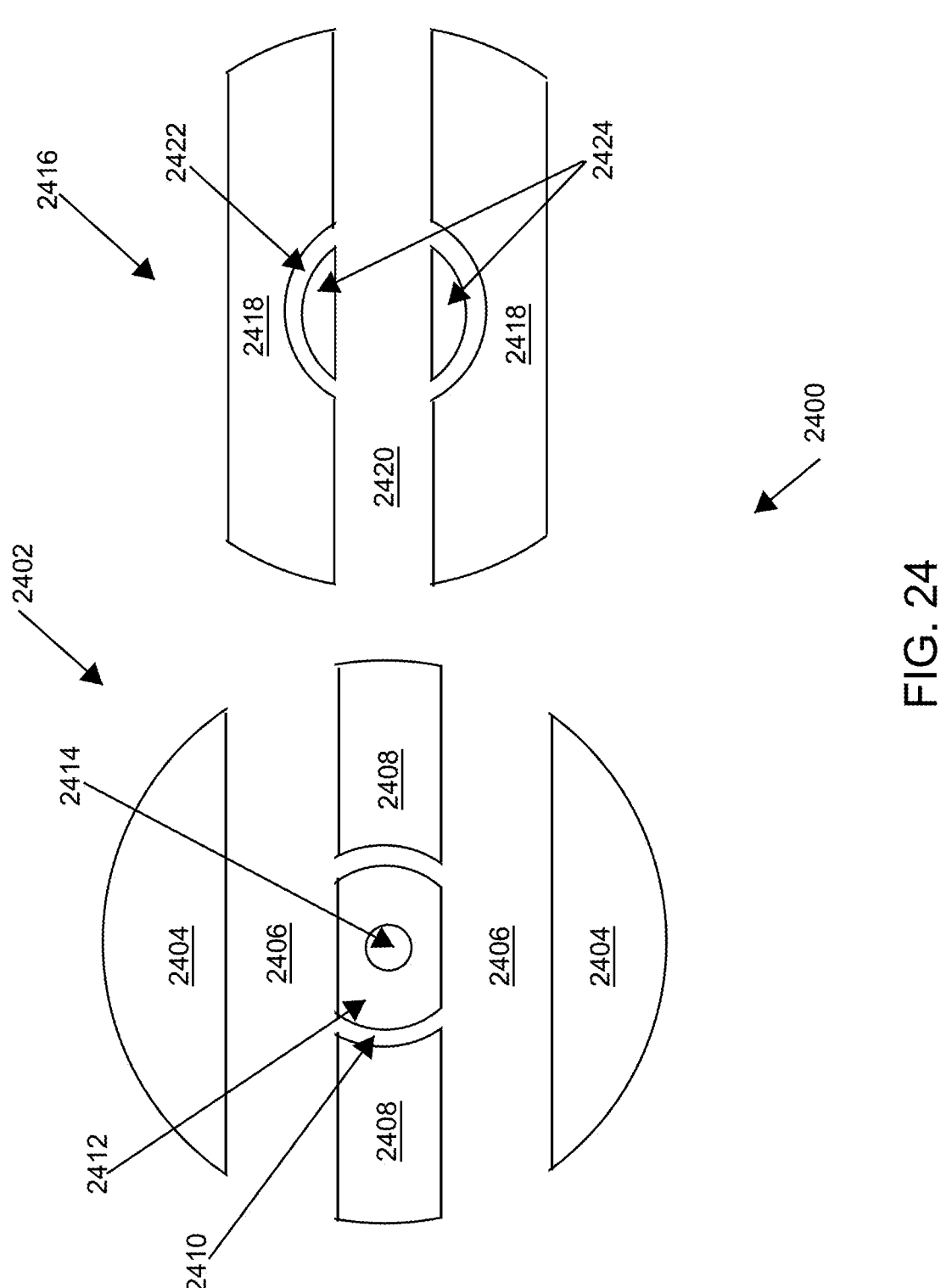

FIG. 23 depicts multiple partial alignments and size differences to facilitate the seating of the distal attachment interface 2304 into the proximal attachment interface 2302, but some of the angular and size changes between the bi-directional embodiment in FIG. 22 and the unidirectional embodiment in FIG. 23 may cause, during torqueing of the delivery system, some mechanical bias or forces that may cause the proximal and distal attachment interfaces 2302, 2304 to twist apart or out of full alignment. In other variations of the attachment interface, a subset of the alignment/seating features described in FIG. 23 may be implement, to achieve a different balance of between ease of seating, mechanical integrity and other factors.

Figure 25:
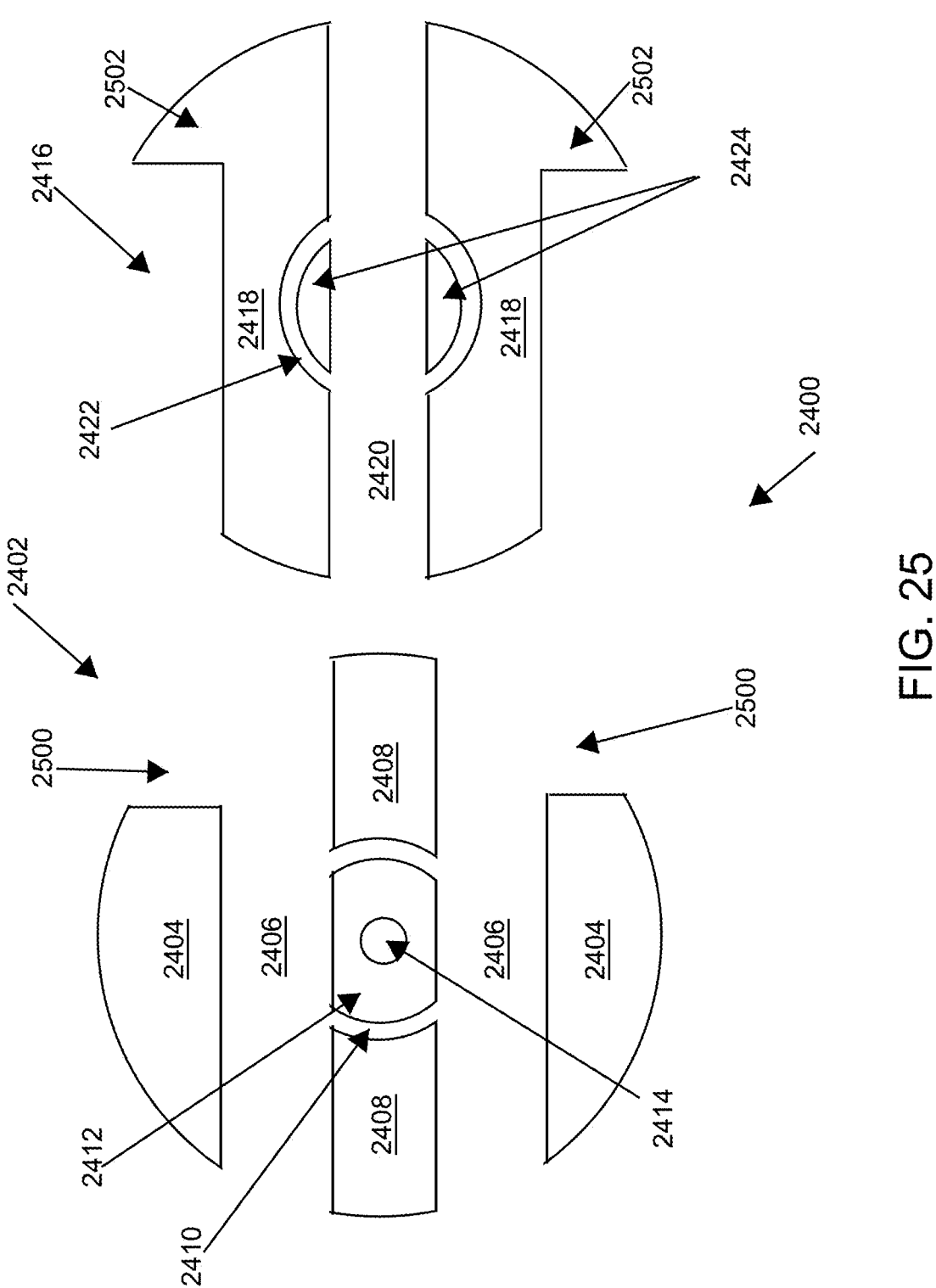

FIGS. 24 and 25 depict additional schematic variations of an attachment interface 2400 wherein the proximal attachment interface 2402 comprises two lateral alignment bodies 2404, two channels 2406, two central alignment bodies 2408 with a drive shaft cavity 2410 there between and an oblong drive shaft head 2412 and central lumen 2414. The distal attachment interface 2416 comprises two paramedial alignment bodies 2418 configured to be inserted into the channels 2406, a central channel 2420 configured to receive the two central alignment bodies 2408 and the drive shaft head 2412 a central rotor shaft cavity 2422 in which two rotor shaft arms or projections 2424 are configured to receive and engage the oblong drive shaft head 2412. Although all of the structures and surfaces of this embodiment of the engagement interface are parallel, in other variations, one or more surfaces may be angled, and or comprise additional recesses/cutouts 2500 and flanges/projections 2502, as depicted in FIG. 25.

While the embodiments herein have been particularly shown and described with references to embodiments thereof, it will be understood by those skilled in the art that various changes in form and details may be made therein without departing from the scope of the embodiments. For all of the embodiments described above, the steps of the methods need not be performed sequentially.

What is claimed is:
1. A method, comprising:
navigating an expandable stent structure to a target location using a delivery catheter; and
actuating a rotor approximate the expandable stent structure at a distal section of the delivery catheter to unwind and extend a tensioning member from the delivery catheter to permit expansion of the expandable stent structure, wherein the expandable stent structure includes an attachment line located around a circumference of the expandable stent structure and the tensioning member is coupled to the attachment line.

2. The method of claim 1, wherein the tensioning member is looped around the attachment line to couple the tensioning member to the expandable stent structure.

3. The method of claim 1, wherein the attachment line is wrapped around the circumference of the expandable stent structure more than once.

4. The method of claim 1, further comprising releasing the expandable stent structure from the delivery catheter by decoupling the tensioning member from the attachment line and retracting the tensioning member.

5. The method of claim 4, wherein, after releasing the expandable stent structure, the attachment line is retained on the expandable stent structure.

6. The method of claim 1, further comprising setting the expandable stent structure in a target pose using a steering assembly of the delivery catheter.

7. The method of claim 1, further comprising setting the expandable stent structure in a target pose using a catheter extension assembly of the delivery catheter.

8. The method of claim 1, further comprising withdrawing a catheter sheath to expose the expandable stent structure prior to actuating the rotor of the delivery catheter.

9. The method of claim 1, further comprising, prior to navigating the expandable stent structure to the target location:

inserting the delivery catheter through the expandable stent structure while the expandable stent structure is in an expanded state;

looping an end of the tensioning member around the attachment line;

attaching the end of the tensioning member to the rotor;

collapsing the expandable stent structure onto the delivery catheter; and rotating the rotor to wind the tensioning member onto the rotor.

10. The method of claim 1, wherein the tensioning member is one of a plurality of tensioning members coupled to the attachment line.

11. The method of claim 10, wherein actuating the rotor unwinds and extends each of the plurality of tensioning members from the delivery catheter to permit expansion of the expandable stent structure.

12. The method of claim 1, wherein the tensioning member is one of a plurality of tensioning members and the attachment line is one of a plurality of attachment lines, and each of the plurality of tensioning member is coupled to one of the plurality of attachment lines.

13. The method of claim 1, wherein the expandable stent structure is a heart valve implant.

14. The method of claim 1, further comprising, before navigating the expandable stent structure to the target location, loading the expandable stent into the delivery catheter, wherein loading the expandable stent structure includes:

collapsing the expandable stent structure into a delivery configuration, and winding the tensioning member about the rotor.

15. The method of claim 14, wherein loading the expandable stent structure further includes pulling at least a portion of the attachment line into a stator housing surrounding the rotor.

16. The method of claim 14, wherein loading the expandable stent structure further includes winding at least a portion of the attachment line around the rotor.

17. The method of claim 1, wherein the attachment line is an attachment loop.

* * * * *